(12) United States Patent
Gentalen et al.

(10) Patent No.: US 10,514,360 B1
(45) Date of Patent: Dec. 24, 2019

(54) SOFTWARE FOR MICROFLUIDIC SYSTEMS INTERFACING WITH MASS SPECTROMETRY

(71) Applicant: Intabio, Inc., Portola Valley, CA (US)

(72) Inventors: Erik Gentalen, Fremont, CA (US); Steve Lacy, Troy, MI (US); Scott Mack, Boulder Creek, CA (US); Luc Bousse, Los Altos, CA (US); Morten Jensen, Saratoga, CA (US)

(73) Assignee: INTABIO, INC., Newark, CA (US)

(*) Notice: Subject to any disclaimer, the term of this patent is extended or adjusted under 35 U.S.C. 154(b) by 0 days.

(21) Appl. No.: 16/532,955

(22) Filed: Aug. 6, 2019

Related U.S. Application Data

(63) Continuation of application No. 16/427,767, filed on May 31, 2019.

(60) Provisional application No. 62/678,265, filed on May 31, 2018, provisional application No. 62/684,090, filed on Jun. 12, 2018.

(51) Int. Cl.
*G01N 27/44* (2006.01)
*H01J 49/14* (2006.01)
*G01N 27/447* (2006.01)
*G01N 30/60* (2006.01)
*G01N 30/72* (2006.01)

(52) U.S. Cl.
CPC . *G01N 27/44791* (2013.01); *G01N 27/44795* (2013.01); *G01N 30/6078* (2013.01); *G01N 30/7266* (2013.01); *H01J 49/147* (2013.01)

(58) Field of Classification Search
CPC ....... G01N 27/44791; G01N 27/44795; G01N 30/6078; G01N 30/7266; H01J 49/10; H01J 49/165; H01J 49/167
See application file for complete search history.

(56) References Cited

U.S. PATENT DOCUMENTS

| 5,110,434 | A |   | 5/1992  | Zhu et al.           |
|-----------|---|---|---------|----------------------|
| 5,183,489 | A |   | 2/1993  | Brehm et al.         |
| 5,259,939 | A |   | 11/1993 | Chen                 |
| 5,395,502 | A |   | 3/1995  | Pawliszyn            |
| 5,423,964 | A | * | 6/1995  | Smith ... G01N 27/44717 |
|           |   |   |         | 204/452              |
| 5,468,359 | A |   | 11/1995 | Pawliszyn            |

(Continued)

FOREIGN PATENT DOCUMENTS

| AT | 548347 T    | 3/2012 |
|----|-------------|--------|
| DE | 05705627 T1 | 5/2007 |

(Continued)

OTHER PUBLICATIONS

Baker, C. et al. Online Coupling of Digital Microfluidic Devices with Mass Spectrometry Detection Using an Eductor with Electrospray Ionization. Analytical Chemistry, vol. 84, 2012, 6 pages.

(Continued)

*Primary Examiner* — David E Smith
(74) *Attorney, Agent, or Firm* — Wilson Sonsini Goodrich & Rosati

(57) ABSTRACT

Methods, devices, and systems for improving the quality of electrospray ionization mass spectrometer (ESI-MS) data are described, as are methods, devices, and systems for achieving improved correlation between chemical separation data and mass spectrometry data.

24 Claims, 21 Drawing Sheets

(56) References Cited

U.S. PATENT DOCUMENTS

| | | | |
|---|---|---|---|
| 5,779,868 A | 7/1998 | Parce et al. |
| 5,784,154 A | 7/1998 | Pawliszyn |
| 5,800,690 A | 9/1998 | Chow et al. |
| 5,842,787 A | 12/1998 | Kopf-Sill et al. |
| 5,858,195 A | 1/1999 | Ramsey |
| 5,876,675 A | 3/1999 | Kennedy |
| 5,880,071 A | 3/1999 | Parce et al. |
| 5,957,579 A | 9/1999 | Kopf-Sill et al. |
| 5,958,203 A | 9/1999 | Parce et al. |
| 5,965,001 A | 10/1999 | Chow et al. |
| 5,972,187 A | 10/1999 | Parce et al. |
| 5,985,121 A | 11/1999 | Wu et al. |
| 6,001,229 A | 12/1999 | Ramsey |
| 6,010,607 A | 1/2000 | Ramsey |
| 6,010,608 A | 1/2000 | Ramsey |
| 6,033,546 A | 3/2000 | Ramsey |
| 6,042,709 A | 3/2000 | Parce et al. |
| 6,048,498 A | 4/2000 | Kennedy |
| 6,080,295 A | 6/2000 | Parce et al. |
| 6,110,343 A | 8/2000 | Ramsey et al. |
| 6,149,787 A | 11/2000 | Chow et al. |
| 6,167,910 B1 | 1/2001 | Chow |
| 6,186,660 B1 | 2/2001 | Kopf-Sill et al. |
| 6,231,737 B1 | 5/2001 | Ramsey et al. |
| 6,287,520 B1 | 9/2001 | Parce et al. |
| 6,321,791 B1 | 11/2001 | Chow |
| 6,413,401 B1 | 7/2002 | Chow et al. |
| 6,430,512 B1 | 8/2002 | Gallagher |
| 6,482,364 B2 | 11/2002 | Parce et al. |
| 6,494,230 B2 | 12/2002 | Chow et al. |
| 6,517,234 B1 | 2/2003 | Kopf-Sill et al. |
| 6,547,942 B1 | 4/2003 | Parce et al. |
| 6,611,768 B2 | 8/2003 | Gallagher |
| 6,632,655 B1 | 10/2003 | Mehta et al. |
| 6,744,046 B2 | 6/2004 | Valaskovic et al. |
| 6,803,568 B2 | 10/2004 | Bousse et al. |
| 6,831,274 B2 | 12/2004 | Smith et al. |
| 6,974,526 B2 | 12/2005 | Lee et al. |
| 6,974,527 B2 | 12/2005 | Liu et al. |
| 6,977,372 B2 | 12/2005 | Valaskovic et al. |
| 7,001,496 B2 | 2/2006 | Parce et al. |
| 7,022,214 B2 | 4/2006 | Olech |
| 7,166,202 B2 | 1/2007 | Bukshpan et al. |
| 7,285,411 B1 | 10/2007 | Parce et al. |
| 7,339,166 B2 | 3/2008 | Tang et al. |
| 7,381,317 B2 | 6/2008 | Liu et al. |
| 7,391,020 B2 | 6/2008 | Bousse et al. |
| 7,425,700 B2 | 9/2008 | Stults et al. |
| 7,426,442 B2 | 9/2008 | Gallagher |
| 7,655,477 B1 | 2/2010 | Schneider et al. |
| 7,825,375 B2 | 11/2010 | Sano |
| 8,076,152 B2 | 12/2011 | Robotti |
| 8,097,472 B2 | 1/2012 | Schneider et al. |
| 8,260,561 B2 | 9/2012 | Gallagher |
| 8,613,845 B2 | 12/2013 | Maxwell et al. |
| 8,859,296 B2 | 10/2014 | Schneider et al. |
| 8,940,232 B2 | 1/2015 | Roach et al. |
| 9,006,648 B2 | 4/2015 | Ramsey et al. |
| 9,159,537 B2 | 10/2015 | McGivney et al. |
| 9,255,905 B1 | 2/2016 | Mellors et al. |
| 9,347,440 B2 | 5/2016 | Lebl et al. |
| 9,362,102 B2 | 6/2016 | Dovichi et al. |
| 9,377,440 B2 | 6/2016 | Wu et al. |
| 9,465,014 B2 | 10/2016 | Dovichi et al. |
| 9,502,225 B2 | 11/2016 | Mellors et al. |
| 9,606,082 B2 | 3/2017 | Mellors et al. |
| 9,728,387 B2 | 8/2017 | Mellors et al. |
| 9,778,223 B2 | 10/2017 | Schneider et al. |
| 1,020,921 A1 | 2/2019 | Mellors |
| 2002/0079220 A1 | 6/2002 | Pawliszyn |
| 2002/0139751 A1 | 10/2002 | Zhang et al. |
| 2003/0089605 A1 | 5/2003 | Timperman |
| 2004/0091943 A1 | 5/2004 | Schneider |
| 2004/0112751 A1 | 6/2004 | Han et al. |
| 2004/0113068 A1 | 6/2004 | Bousse et al. |
| 2004/0202994 A1 | 10/2004 | Timperman |
| 2005/0021799 A1 | 1/2005 | Imamura et al. |
| 2006/0113463 A1 | 6/2006 | Rossier et al. |
| 2007/0163884 A1 | 7/2007 | Strand et al. |
| 2008/0035484 A1 | 2/2008 | Wu et al. |
| 2008/0318334 A1 | 12/2008 | Robotti |
| 2009/0035770 A1 | 2/2009 | Mathies et al. |
| 2009/0194419 A1 | 8/2009 | Huang et al. |
| 2010/0116659 A1 | 5/2010 | Liu et al. |
| 2010/0155243 A1 | 6/2010 | Schneider et al. |
| 2010/0193702 A1 | 8/2010 | Li et al. |
| 2011/0072914 A1 | 3/2011 | Lebl et al. |
| 2011/0243813 A1 | 10/2011 | Jackinsky et al. |
| 2012/0080316 A1 | 4/2012 | Schneider et al. |
| 2013/0140180 A1 | 6/2013 | Dovichi et al. |
| 2013/0190212 A1 | 7/2013 | Handique et al. |
| 2013/0280815 A1 | 10/2013 | Wu et al. |
| 2013/0319862 A1* | 12/2013 | Kotowski ........ G01N 27/44704 |
| | | 204/452 |
| 2014/0360877 A1 | 12/2014 | Ramsey et al. |
| 2015/0008130 A1 | 1/2015 | Schneider et al. |
| 2015/0093757 A1 | 4/2015 | Gavin |
| 2015/0162177 A1 | 6/2015 | McGivney et al. |
| 2015/0311056 A1* | 10/2015 | Dovichi ............ G01N 30/7266 |
| | | 250/282 |
| 2015/0340219 A1* | 11/2015 | Mellors .................. H01J 49/165 |
| | | 250/288 |
| 2015/0362460 A1 | 12/2015 | Ferguson |
| 2016/0370319 A1 | 12/2016 | Molho et al. |
| 2017/0025263 A1 | 1/2017 | Mellors et al. |
| 2017/0045527 A1 | 2/2017 | Muthusamy et al. |
| 2017/0176386 A1* | 6/2017 | Gentalen ........... B01L 3/502715 |
| 2017/0299549 A1 | 10/2017 | Schneider et al. |
| 2017/0363575 A1 | 12/2017 | Huang |
| 2018/0003674 A1 | 1/2018 | Gentalen |
| 2018/0036729 A1 | 2/2018 | Furtaw et al. |
| 2018/0036730 A1 | 2/2018 | Furtaw et al. |

FOREIGN PATENT DOCUMENTS

| | | |
|---|---|---|
| EP | 1718960 B1 | 3/2012 |
| JP | 4900245 B2 | 3/2012 |
| WO | WO-2005072121 A2 | 8/2005 |
| WO | WO-2007055293 A1 | 5/2007 |
| WO | WO-2015048458 A2 | 4/2015 |
| WO | WO-2017012397 A1 | 1/2017 |
| WO | WO-2017095813 A1 | 6/2017 |
| WO | WO-2017123970 A1 | 7/2017 |

OTHER PUBLICATIONS

Benz, C. et al. Chip-Based Free-Flow Electrophoresis with Integrated Nanospray Mass-Spectrometry. Angewandte Chemie International Edition, vol. 54, 2015, 5 pages.

CE Pharm 2016, Roundtable Discussion Notes (2016). 3 pages. Retrieved at URL: <https://www.casss.org/page/CE16111b>.

Chartogne et al. Capillary electrophoretic separations of proteins using carrier ampholytes. Journal of Chromatography A 959:289-298 (2002).

Chen, et al. Comparison of ampholytes used for slab gel and capillary isoelectric focusing of recombinant tissue-type plasminogen activator glycoforms. J Chromatogr A. Sep. 13, 1996;744(1-2):279-84.

Co-pending U.S. Appl. No. 16/427,767, filed May 31, 2019.

Cui, H. et al. Isoelectric Focusing in a Poly(dimethylsiloxane) Microfluidic Chip. Analytical Chemistry, vol. 77, 2005, 7 pages.

Dai et al. Capillary Isoelectric Focusing-Mass Spectrometry Method for the Separation and Online Characterization of Intact Monoclonal Antibody Charge Variants. Anal Chem. Feb. 6, 2018;90(3):2246-2254.

Dolník, V. Wall coating for capillary electrophoresis on microchips. Electrophoresis. Nov. 2004;25(21-22):3589-601.

Figeys, D. et al. An Integrated Microfluidics-Tandem Mass Spectrometry System for Automated Protein Analysis. Analytical Chemistry, vol. 70, No. 18, Sep. 15, 1998, 7 pages.

(56) References Cited

OTHER PUBLICATIONS

Geiser, et al. Potential of formamide and N-methylformamide in nonaqueous capillary electrophoresis coupled to electrospray ionization mass spectrometry. Application to the analysis of beta-blockers. J Chromatogr A. Dec. 6, 2002;979(1-2):389-98.
Gentalen Erik, NIH SBIR Award Abstract #4R44TR002570-02. Award Notice Date: Feb. 28, 2019. 2 pages.
Haselberg, R. et al. Performance of a Sheathless Porous Tip Sprayer for Capillary Electrophoresis-Electrospray Ionization-Mass Spectrometry of Intact Proteins. Journal of Chromatography A, vol. 1217, 2010, 7 pages.
Hühner et al. Capillary isoelectric focusing-mass spectrometry: Coupling strategies and applications. Electrophoresis 36:2670-2686 (2015). First published Aug. 24, 2015. DOI: https://doi.org/10.1002/elps.201500185.
Hjertén, Stellan. High-performance electrophoresis : Elimination of electroendosmosis and solute adsorption. Journal of Chromatography A. vol. 347, 1985, pp. 191-198.
Hu, X. et al. Fabrication of a Polystyrene Microfluidic Chip Coupled to Electrospray Ionization Mass Spectrometry for Protein Analysis. Journal of Chromatography B, vol. 990, 2015, 8 pages.
Huang. Finding a Piece of the Protein Characterization Puzzle. The Analytical Chemist, Nov. 2015, pp. 46-48.
Jiang, Y. et al. Integrated Plastic Microfluidic Devices with ESI-MS for Drug Screening and Residue Analysis. Analytical Chemistry, vol. 73, 2001, 6 pages.
Jin et al. Estimation of isoelectric points of human plasma proteins employing capillary isoelectric focusing and peptide isoelectric point markers. Electrophoresis. Sep. 2002;23(19):3385-91.
Karger, et al. High-performance capillary electrophoresis in the biological sciences. J Chromatogr. Aug. 11, 1989;492:585-614.
Lalwani et al. Isoelectric buffers, part 3: Determination of pKa and pI values of diamino sulfate carrier ampholytes by indirect UV-detection capillary electrophoresis. Electrophoresis 26(13):2503-2510 (Jul. 2005). First published Jul. 4, 2005. DOI: https://doi.org/10.1002/elps.200500002.
Li, N. et al. Evaluation of the iCE280 Analyzer as a Potential High-Throughput Tool for Formulation Development. Journal of Pharmaceutical and Biomedical Analysis, vol. 43, 2007, 11 pages.
Li, Y. et al. Integration of Isoelectric Focusing with Parallel Sodium Dodecyl Sulfate Gel Electrophoresis for Multidimensional Protein Separations in a Plastic Microfluidic Network. Analytical Chemistry, vol. 76, 2004, 7 pages.
Mack, et al. A systematic study in CIEF: defining and optimizing experimental parameters critical to method reproducibility and robustness. Electrophoresis. Dec. 2009;30(23):4049-58.
Manabe, et al. Separation of human plasma/serum proteins by capillary isoelectric focusing in the absence of denaturing agents. Electrophoresis. Jun. 1997;18(7):1159-65.
Mao, Q. et al. Demonstration of Isoelectric Focusing on an Etched Quartz Chip with UV Absorption Imaging Detection. Analyst, vol. 124, 1999, 5 pages.
Marasco, C. et al. Real-Time Cellular Exometabolome Analysis With a Microfluidic-Mass Spectrometry Platform. PLOS One, Feb. 27, 2015, 19 pages.
Mellors, J. et al. Fully Integrated Glass Microfluidic Device for Performing High-Efficiency Capillary Electrophoresis and Electrospray Ionization Mass Spectrometry. Analytical Chemistry, vol. 80, 2008, 7 pages.
Michels et al. Imaged Capillary Isoelectric Focusing for Charge-Variant Analysis of Biopharmaceuticals. BioProcess 9(10):48-54 (Nov. 2011).
Michels, et al. Separation Methods and Orthogonal Techniques. State-of-the-Art and Emerging Technologies for Therapeutic Monoclonal Antibody Characterization vol. 2. Biopharmaceutical Characterization: The NISTmAb Case Study. Oct. 15, 2015. Chapter 5, pp. 237-284.
Minarik et al. Dispersion effects accompanying pressurized zone mobilisation in capillary isoelectric focusing of proteins. Journal of Chromatography A. Jun. 1996. 738(1):123-128.
Mohan et al. On-line coupling of capillary isoelectric focusing with transient isotachophoresis-zone electrophoresis: A two-dimensional separation system for proteomics. Electrophoresis 23:3160-3167 (2002).
Mokaddem, et al. Online CIEF-ESI-MS in glycerol-water media with a view to hydrophobic protein applications. Electrophoresis. vol. 30, Issue 23, Dec. 2009. pp. 4040-4048.
Nordman et al. Interfacing Microchip Isoelectric Focusing with On-chip Electrospray: Ionization Mass Spectrometry. Journal of Chromatography A 1398:121-126 (2015). Available online Apr. 23, 2015.
Nordman, N. et al. Rapid Biomolecule Analysis Using Two-Dimensional Electrophoresis-Electrospray Ionization Microchip. 15th International Conference on Miniaturized Systems for Chemistry and Life Science, Oct. 2-6, 2011, Seattle, Washington, 3 pages.
Nordman, N. Microchip Technology in Mass Spectrometry-Based Bioanalysis: Advances in the Analysis of Peptides, Proteins, and Pharmaceuticals. Academic Dissertation, University of Helsinki, Apr. 17, 2015, 144 pages.
Poitevin, et al. Comparison of different capillary isoelectric focusing methods—use of "narrow pH cuts" of carrier ampholytes as original tools to improve resolution. J Chromatogr A. Jul. 6, 2007;1155(2):230-6.
Procházková et al. Analysis of amino acids by combination of carrier ampholyte-free IEF with ITP. Electrophoresis 28:2168-2173 (2007).
Righetti, et al. Carrier ampholytes for IEF, on their fortieth anniversary (1967-2007), brought to trial in court: the verdict. Electrophoresis. Nov. 2007;28(21):3799-810.
Roy, et al. Surface analysis, hydrophilic enhancement, ageing behavior and flow in plasma modified cyclic olefin copolymer (COC)-based microfluidic devices. Sensors and Actuators B: Chemical. vol. 150, Issue 2, Oct. 28, 2010, pp. 537-549.
Salas-Solano et al. Robustness of iCIEF Methodology for the Analysis of Monoclonal Antibodies: An Interlaboratory Study. Journal of Separation 35:3124-3129 (2012).
Salas-Solano, O. et al. Intercompany Study to Evaluate the Robustness of Capillary Isoelectric Focusing Technology for the Analysis of Monoclonal Antibodies. Chromatographia, vol. 73, 2011, 8 pages.
Scientific Considerations in Demonstrating Biosimilarity to a Reference Product: Guidance for Industry, U.S. Department of Health and Human Services Food and Drug Administration, Apr. 2015. 27 pages. Retrieved Feb. 12, 2019 from URL:< https://www.fda.gov/downloads/drugs/guidances/ucm291128.pdf>.
Shimura, K. et al. Isoelectric Focusing in a Microfluidically Defined Electrophoresis Channel. Analytical Chemistry, vol. 80, 2008, 6 pages.
Sikanen, T. et al. Intact Protein Separations With Inherently Biocompatible Ormocomp Separation Chip With Integrated Electrospray Ionization Emitter. 15th International Conference on Miniaturized Systems for Chemistry and Life Science, Oct. 2-6, 2011, Seattle, Washington, 3 pages.
Sikanen, T. et al. Microchip Capillary Electrophoresis-Electrospray Ionization-Mass Spectrometry of Intact Proteins Using Uncoated Ormocomp Microchips. Analytica Chimica Acta, vol. 711, 2012, 8 pages.
Sikanen, T. et al. Microchip Technology in Mass Spectrometry. Mass Spectrometry Reviews, vol. 29, 2010, 41 pages.
Gentalen Erik, NIH SBIR Award Abstract #1R44TR002570-01. Award Notice Date: Aug. 10, 2018. 2 pages.
Gentalen Erik, NSF SBIR Phase 1 Award Abstract #1747340 (Dec. 18, 2017). 2 pages.
Nordman et al. Interfacing Microchip Isoelectric Focusing with On-chip Electrospray: Ionization Mass Spectrometry, Supplementary Data. Journal of Chromatography A 1398:121-126 (2015). 6 pages. Available online Apr. 23, 2015.
Tentori et al. Supporting Information: Detection of Isoforms Differing by a Single Charge Unit in Individual Cells. Angew Chem Ed 55 (2016). 25 pages.
Sung, et al. Chip-based microfluidic devices coupled with electrospray ionization-mass spectrometry. Electrophoresis. vol. 26, Issue 9, No. 9, May 2005. pp. 1783-1791.

(56) References Cited

OTHER PUBLICATIONS

Suzuki, S. et al. High-speed Electrophoretic Analysis of 1-phenyl-3-methyl-5-pyrazolone Derivatives of Monosaccharides on a Quartz Microchip with Whole-Channel UV Detection. Electrophoresis, vol. 24, 2003, 6 pages.

Tan, W. et al. Miniaturized Capillary Isoelectric Focusing in Plastic Microfluidic Devices. Electrophoresis, vol. 23, 2002, 8 pages.

Tang et al. Comparison of Protein Separations in Capillary Zone Electrophoresis and Capillary Isoelectric Focusing Interfacing with Electrospray Mass Spectrometry. Journal of Mass Spectrometry. Nov. 1996. 31(11):1284-1290.

Taylor, P. Matrix Effects: The Achilles Heel of Quantitative High-Performance Liquid Chromatography-Electrospray-Tandem Mass Spectrometry. Clinical Biochemistry, vol. 38, 2005, 7 pages.

Tentori et al. Detection of Isoforms Differing by a Single Charge Unit in Individual Cells. Angew Chem Ed 55 (2016). 6 pages.

Tentori et al. Performance implications of chemical mobilization after microchannel IEF. Electrophoresis 35:1453-1460 (2014).

Thormann et al. High-resolution computer simulation of electrophoretic mobilization in isoelectric focusing. Electrophoresis 29:1676-1686 (2008).

Týčová et al. Recent advances in CE-MS coupling: Instrumentation, methodology, and applications. Electrophoresis. Jan. 2017;38(1):115-134.

Vagenende, et al. Mechanisms of protein stabilization and prevention of protein aggregation by glycerol. Biochemistry. Nov. 24, 2009;48(46):11084-96.

Vlckova, M. et al. Pharmaceutical Applications of Isoelectric Focusing on Microchip With Imaged UV Detection. Journal of Chromatography A, vol. 1181, 2008, 8 pages.

Wakankar, A. et al. Analytical Methods for Physicochemical Characterization of Antibody Drug Conjugates. mAbs, vol. 3, No. 2, Mar./Apr. 2011, 12 pages.

Wehr. Chapter 9: Capillary Isoelectric Focusing. Handbook of Isoelectric Focusing and Proteomics, D. Garfin and S. Ahuja, Eds., Elsevier Inc. pp. 181-210 (2005).

Wen, J. et al. Microfabricated Isoelectric Focusing Device for Direct Electrospray Ionization-Mass Spectrometry. Electrophoresis, vol. 21, 2000, 7 pages.

Wu, et al. Secrets of iCE Method Design for Protein Therapeutics. Protein Simple. Presentation Abstract. Tuesday Mar. 27, 2012. URL:<http://events.r20.constantcontact.com/register/event?llr=p9xbiodab&oeidk=a07e5nz3rtw6f41039b>.

Wu, J. et al. Absorption Spectra and Multicapillary Imaging Detection for Capillary Isoelectric Focusing Using a Charge Coupled Device Camera. Analyst, vol. 120, May 1995, 5 pages.

Wu, J. et al. Capillary Isoelectric Focusing with Whole Column Detection and a Membrane Sample Preparation System. Analytica Chimica Acta, vol. 383, 1999, 12 pages.

Wu, J. J et al. Protein Analysis by Isoelectric Focusing in a Capillary Array With an Absorption Imaging Detector. Journal of Chromatography B, vol. 669, 1995, 5 pages.

Yang et al. Capillary isoelectric focusing-electrospray ionization mass spectrometry for transferrin glycoforms analysis. Anal Biochem. Dec. 1, 1996;243(1):140-9.

Zhang, B. et al. Microfabricated Devices for Capillary Electrophoresis—Electrospray Mass Spectrometry. Analytical Chemistry, vol. 71, 1999, 7 pages.

Zhang et al. Stepwise Mobilization of Focused Proteins in Capillary Isoelectric Focusing Mass Spectrometry. Analytical Chemistry 72(7):1462-1468 (Apr. 1, 2000). Published online Mar. 3, 2000. DOI: https://doi.org/10.1021/ac9912653.

Zhong, X, et al. Flow-Through Microvial Facilitating Interface of Capillary Isoelectric Focusing and Electrospray Ionization Mass Spectrometry. Analytical Chemistry, vol. 83, 2011, 8 pages.

\* cited by examiner

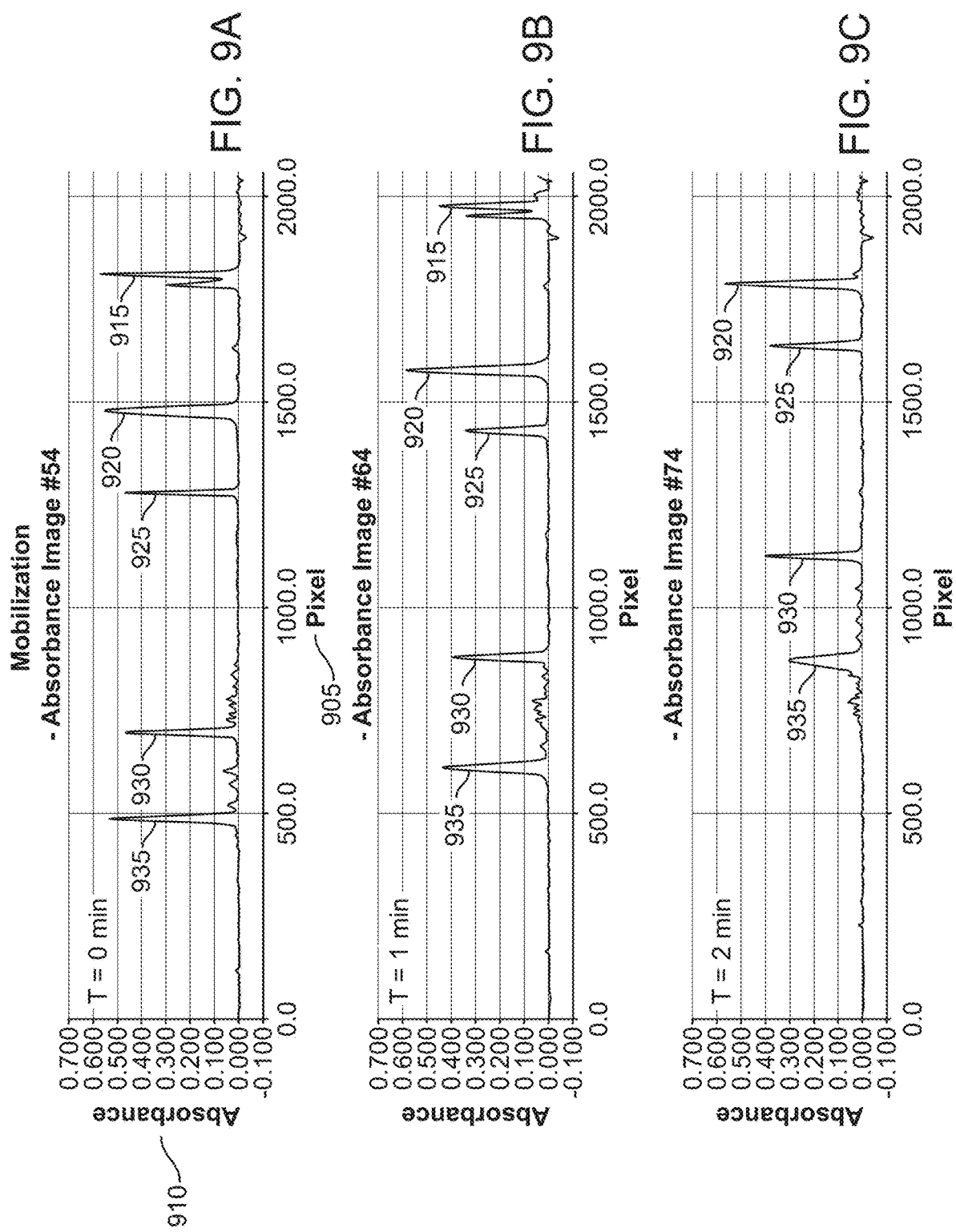

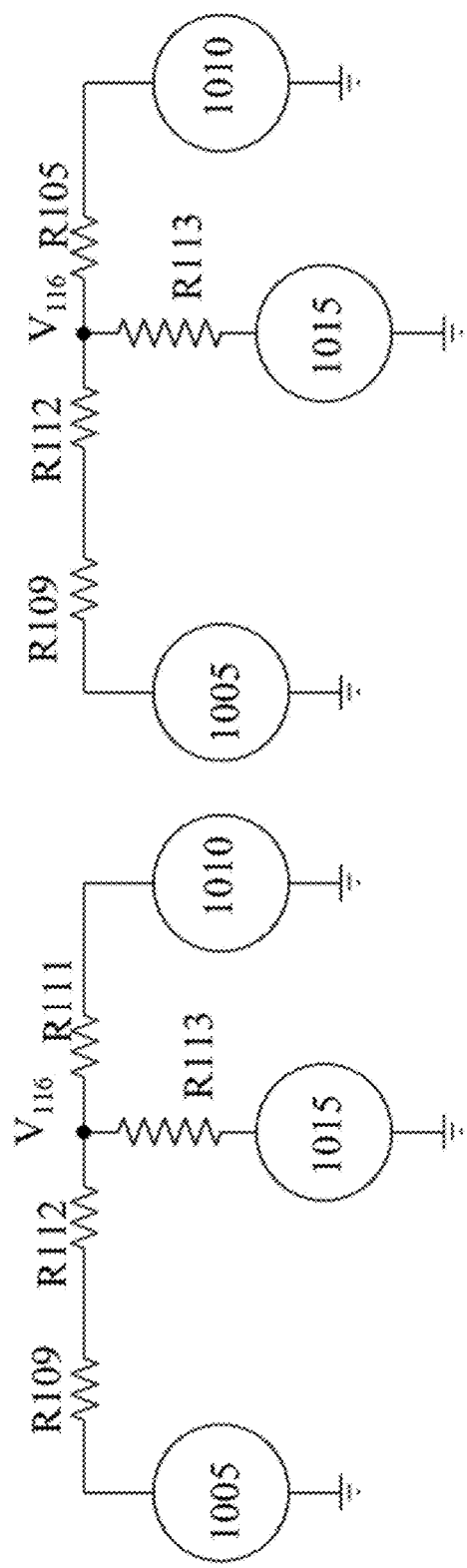

SOFTWARE FOR MICROFLUIDIC SYSTEMS INTERFACING WITH MASS SPECTROMETRY

CROSS-REFERENCE

This application is a Continuation Application which claims the benefit of U.S. application Ser. No. 16/427,767, filed May 31, 2019, which claims the benefit of U.S. Provisional Application No. 62/678,265, filed on May 31, 2018, and U.S. Provisional Application No. 62/684,090, filed on Jun. 12, 2018, each of which is incorporated herein by reference in its entirety.

BACKGROUND

The present disclosure relates to the field of chemical analysis, and in particular, to the separation of analytes in a mixture and their subsequent analysis by mass spectrometry (MS). Separation of analyte components from a more complex analyte mixture on the basis of an inherent quality of the analytes, and providing sets of fractions that are enriched for states of that quality, is a key part of analytical chemistry. Simplifying complex mixtures in this manner reduces the complexity of downstream analysis. However, complications can arise when attempting to interface known enrichment methods and/or devices with analytical equipment and/or techniques.

A variety of methods have been used, for example, to interface protein sample preparation techniques with downstream detection systems such as mass spectrometers. A common method is to prepare samples using liquid chromatography and collect fractions for mass spectrometry (LC-MS). This has the disadvantage of requiring protein samples to be digested into peptide fragments, leading to a large number of sample fractions which must be analyzed and complex data reconstruction post-run. While certain forms of liquid chromatography can be coupled to a mass spectrometer, for example peptide map reversed-phase chromatography, these known techniques are restricted to using peptide fragments, rather than intact proteins, which limits their utility.

Another method to introduce samples into a mass spectrometer is electrospray ionization (ESI). In ESI, small droplets of sample and solution are emitted from a distal end of a capillary or microfluidic device comprising an electrospray feature, such as an emitter tip or orifice, by the application of an electric field between the capillary tip or emitter tip and the mass spectrometer source plate. The droplet stretches and expands in this induced electric field to form a cone shaped emission (i.e., a "Taylor cone") which comprises increasingly small droplets that evaporate and produce the gas phase ions that are introduced into the mass spectrometer for further separation and detection. Typically, emitter tips are formed from a capillary, which provides a convenient droplet volume for ESI. Capillaries, however, are limited to a linear flow path that does not allow for multi-step sample processing. ESI also depends on the voltage at the ESI tip to remain constant throughout the analysis, which can be a challenge in many assays, where internal fluid resistances can change over time, altering the voltage drop in different parts of the electrical circuit and thereby changing the voltage at the ESI tip.

Other work has been pursued with microfluidic devices. Microfluidic devices may be produced by various known techniques and provide fluidic channels of defined dimensions that can make up a channel network designed to perform different fluid manipulations. These devices offer an additional level of control and complexity than capillaries, making them a better choice for sample prep. However, like capillaries, these tools often provide limited characterization of separated analyte fractions prior to introduction to a mass spectrometer, if any. Also, systems with capillaries or microfluidic devices generally provide no tools for calibrating the system to reestablish a Taylor cone during operation.

Methods, devices, systems, and software for improving the quality of electrospray ionization mass spectrometry (ESI-MS) data are described, as are methods, devices, systems, and software for achieving more quantitative characterization of and improved correlation between chemical separation data and mass spectrometry data.

SUMMARY

Disclosed herein are methods for maintaining an electrospray ionization (ESI) tip at a constant voltage relative to ground while performing a separation reaction, the method comprising: a) applying a first voltage to a proximal end of a separation channel, wherein a distal end of the separation channel is in fluid and electrical communication with the ESI tip; b) applying a second voltage to a proximal end of an auxiliary fluid channel, wherein a distal end of the auxiliary fluid channel is in fluid and electrical communication with the distal end of the separation channel; c) performing the separation reaction to separate a mixture of analytes, wherein the separation reaction takes place within the separation channel; and d) monitoring a change in resistance of the separation channel or a change in voltage at the ESI tip in a feedback loop that adjusts the first and second voltages to maintain a constant voltage drop across the separation channel and a constant voltage at the ESI tip. In some embodiments, the separation channel is a lumen of a capillary. In some embodiments, the capillary comprises a microvial spray tip. In some embodiments, the separation channel is a fluid channel within a microfluidic device. In some embodiments, the separation reaction comprises an isoelectric focusing reaction. In some embodiments, the separation reaction comprises an electrophoretic separation reaction. In some embodiments, the first voltage is applied at a cathode and the second voltage is applied at an anode. In some embodiments, the voltage at the ESI tip is held at ground. In some embodiments, the voltage at the ESI tip is held at the second voltage. In some embodiments, the adjustment to the first and second voltages comprises subtracting a transient voltage change measured at the ESI tip from the first voltage and second voltage. In some embodiments, the voltage at the ESI tip is measured using a power supply that provides the first or second voltage. In some embodiments, the feedback loop operates at a frequency of at least 0.1 Hz. In some embodiments, the feedback loop operates at a frequency of at least 10 Hz. In some embodiments, the feedback loop maintains the voltage at the ESI tip to within ±10% of a pre-set value. In some embodiments, the feedback loop maintains the voltage at the ESI tip to within ±1% of a pre-set value. In some embodiments, the feedback loop maintains the voltage drop across the separation channel to within ±10% of a pre-set value. In some embodiments, the feedback loop maintains the voltage drop across the separation channel to within ±1% of a pre-set value.

Also disclosed herein are methods comprising: a) providing a sample comprising a mixture of two or more analytes; b) performing a separation within a fluid channel containing the sample to resolve individual analyte peaks from the mixture of two or more analytes; c) calculating a velocity of an analyte peak upon mobilization of the fluid channel's contents towards a fluid channel exit; and d) using the velocity of the analyte peak to determine a time at which the analyte peak reaches the fluid channel exit. In some embodiments, the fluid channel is a lumen of a capillary. In some embodiments, the fluid channel is part of a microfluidic device. In some embodiments, the separation is based on isoelectric focusing (IEF), capillary zone electrophoresis (CZE), capillary gel electrophoresis (CGE), capillary isotachophoresis (CITP), or micellar electrokinetic chromatography (MEKC). In some embodiments, the velocity of the analyte peak is calculated from a time interval required for the analyte peak to move from a first position to a second position. In some embodiments, the first position, second position, and time interval are determined from a series of two or more images of the fluid channel. In some embodiments, the series of two or more images comprise ultraviolet light absorbance images, visible light absorbance images, or fluorescence images. In some embodiments, the fluid channel exit comprises an electrospray interface with a mass spectrometer. In some embodiments, the time at which the analyte peak reaches the fluid channel exit is used to correlate mass spectrometer data with the analyte peak. In some embodiments, the mobilization of the fluid channel's contents comprises the use of an electroosmotic mobilization technique, a chemical mobilization technique, a hydrodynamic mobilization technique, or any combination thereof. In some embodiments, the two or more analytes comprise proteins, protein-drug conjugates, peptides, nucleic acid molecules, carbohydrate molecules, lipid molecules, metabolite molecules, small organic compounds, or any combination thereof. In some embodiments, a comparison of mass spectrometer data collected for samples of a biologic drug candidate and a reference drug is used to make a determination of biosimilarity. In some embodiments, the velocity of the analyte peak is used in a feedback loop to adjust a control parameter for the separation or mobilization of the analyte peaks. In some embodiments, the control parameter is a voltage. In some embodiments, the feedback loop operates at a frequency of at least 0.1 Hz.

Disclosed herein are methods comprising: a) providing a sample comprising a mixture of two or more analytes; b) performing a separation within a fluid channel containing the sample to resolve individual analyte peaks from the mixture of two or more analytes; and c) collecting mass spectrometer data for the two or more individual analyte peaks emitted from the fluid channel via an electrospray interface with a mass spectrometer; wherein a data collection mode for the mass spectrometer is alternated between a high mass scan and a low mass scan. In some embodiments, the mass spectrometer is switched between the high mass scan and low mass scan data collection modes at a frequency of at least 0.5 Hz. In some embodiments, the fluid channel is a lumen of a capillary. In some embodiments, the fluid channel is part of a microfluidic device. In some embodiments, the separation is based on isoelectric focusing (IEF), capillary zone electrophoresis (CZE), capillary gel electrophoresis (CGE), capillary isotachophoresis (CITP), or micellar electrokinetic chromatography (MEKC). In some embodiments, the high mass scan captures mass spectral data for biological macromolecules. In some embodiments, the biological macromolecules comprise proteins, protein-drug conjugates, nucleic acid molecules, reduced proteins, fusion proteins, protein complexes, or any combination thereof. In some embodiments, the m/z ratio for the high mass scan ranges from 1500 to 6000. In some embodiments, the low mass scan captures mass spectral data for solution-phase ampholytes used in performing an isoelectric focusing separation. In some embodiments, the m/z ratio for the low mass scan ranges from 150 to 1500. In some embodiments, the mass spectra of one or more solution-phase ampholytes are used to calibrate the isoelectric points (pIs) for biological macromolecules identified in the high mass scans.

Disclosed herein are methods comprising: a) performing a separation within a fluid channel containing a sample, wherein the sample comprises a mixture of two or more analytes, and wherein the separation resolves individual analyte peaks from the mixture of two or more analytes; b) mobilizing the fluid channel's contents towards a fluid channel exit, wherein the fluid channel exit comprises an electrospray interface with a mass spectrometer; and c) simultaneously or alternately imaging: (i) at least a portion of the fluid channel to monitor a position of an analyte peak during (a) and (b), and (ii) a Taylor cone existing between the fluid channel exit and an inlet to the mass spectrometer to monitor electrospray performance. In some embodiments, the positions of the analyte peak in two or more images of at least a portion of the fluid channel are used to calculate velocity for the analyte peak. In some embodiments, the velocity of the analyte peak is used to determine a time at which the analyte peak will reach the fluid channel exit. In some embodiments, the time at which the analyte peak reaches the fluid channel exit is used to correlate mass spectrometer data with the analyte peak. In some embodiments, data derived from the imaging of the Taylor cone is used in a feedback loop to adjust electrospray performance. In some embodiments, the feedback loop operates at a frequency of at least 0.1 Hz. In some embodiments, the fluid channel is a lumen of a capillary. In some embodiments, the fluid channel is part of a microfluidic device. In some embodiments, the separation is based on isoelectric focusing (IEF), capillary zone electrophoresis (CZE), capillary gel electrophoresis (CGE), capillary isotachophoresis (CITP), or micellar electrokinetic chromatography (MEKC). In some embodiments, the imaging comprises ultraviolet light absorbance imaging, visible light absorbance imaging, or fluorescence imaging. In some embodiments, the mobilization of the fluid channel's contents comprises the use of an electroosmotic mobilization technique, a chemical mobilization technique, a hydrodynamic mobilization technique, or any combination thereof. In some embodiments, the two or more analytes comprise proteins, protein-drug conjugates, peptides, nucleic acid molecules, carbohydrate molecules, lipid molecules, metabolite molecules, small organic compounds, or any combination thereof.

Disclosed herein are computer-implemented methods for maintaining an electrospray ionization (ESI) tip at a constant voltage relative to ground while performing a separation reaction, the method comprising: a) receiving, using a processor, a first measurement of a voltage at the ESI tip, wherein a distal end of the separation channel is in fluid and electrical communication with the ESI tip; b) receiving, using the processor, a second measurement of the voltage at the ESI tip; c) comparing the second measurement to the first measurement using the processor, wherein if the second measurement differs from the first measurement, the processor causes a voltage at a proximal end of the separation channel and a voltage at a proximal end of an auxiliary fluid channel comprising a distal end that is in fluid and electrical communication with the distal end of the separation channel, to be adjusted such that the voltage at the ESI tip is returned to the first measurement value; and d) repeating steps (a) through (c) at a specified frequency. In some embodiments, the separation channel comprises a lumen of a capillary or a fluid channel within a microfluidic device. In some embodiments, the separation reaction comprises an isoelectric focusing reaction. In some embodiments, the separation reaction comprises an electrophoretic separation reaction. In some embodiments, the voltage at the ESI tip is held at ground. In some embodiments, the specified frequency is at least 1 Hz. In some embodiments, the voltage at the ESI tip is maintained to within ±5% of a specified value.

Also disclosed herein are computer-implemented methods comprising: a) receiving, using a processor, image data comprising two or more images acquired using a detector configured to image all or a portion of a separation channel in a capillary or a microfluidic device; b) processing the image data using the same or a different processor to determine a position of an analyte peak within the separation channel in the two or more images; c) calculating, using the same or a different processor, a velocity of the analyte peak based on the position of the analyte peak in the two or more images and a known time interval between acquisition of the two or more images; and d) determining, using the same or a different processor, a time at which the analyte peak will reach a separation channel outlet. In some embodiments, a separation reaction performed within the separation channel comprises isoelectric focusing (IEF), capillary zone electrophoresis (CZE), capillary gel electrophoresis (CGE), capillary isotachophoresis (CITP), or micellar electrokinetic chromatography (MEKC). In some embodiments, the two or more images comprise ultraviolet light absorbance images, visible light absorbance images, or fluorescence images. In some embodiments, the separation channel outlet is in fluid communication with or comprises an electrospray interface with a mass spectrometer. In some embodiments, the time at which the analyte peak reaches the separation channel outlet is used to correlate mass spectrometer data with the analyte peak. In some embodiments, the analyte is separated from a mixture and comprises a protein, a protein-drug conjugate, a peptide, a nucleic acid molecule, a carbohydrate molecule, a lipid molecule, a metabolite molecule, or a small organic compound. In some embodiments, a comparison of mass spectrometer data collected for samples of a biologic drug candidate and a reference drug is used to make a determination of biosimilarity. In some embodiments, the velocity of the analyte peak is used in a feedback loop to adjust a control parameter for a separation reaction performed in the separation channel. In some embodiments, the control parameter is a voltage. In some embodiments, the feedback loop operates at a frequency of at least 0.1 Hz.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7A provides a schematic illustration of a fluid channel network of an exemplary microfluidic device. FIG. 7B provides a computer aided design (CAD) drawing of an assembled microfluidic device. The fluid channel layer shown in FIG. 7A is sandwiched between two clear layers to seal the fluid channels.

FIGS. 9A-F provide non-limiting examples of data for mobilization of a sample following separation of analytes in a mixture of analytes using isoelectric focusing. FIG. 9A shows an absorbance trace at t=0 minutes (completion of isoelectric focusing). FIG. 9B shows an absorbance trace at t=1 minute. FIG. 9C shows an absorbance trace at t=2 minutes. FIG. 9D shows an absorbance trace at t=3 minutes. FIG. 9E shows an absorbance trace at t=4 minutes. FIG. 9F shows an absorbance trace at t=5 minutes.

FIGS. 10A-B provide representative circuit diagrams for a microfluidic device designed to perform isoelectric focusing to separate analytes and subsequent mobilization of the separated analyte mixture. FIG. 10A provides a representative circuit diagram for the microfluidic device shown in FIG. 7A during isoelectric focusing, in the case where the ESI tip will be held at or close to ground. FIG. 10B shows a representative circuit diagram for the microfluidic device shown in FIG. 7A during chemical mobilization of a separated analyte mixture. The resistance of channel 114 (shown in FIG. 7A) is assumed to be negligible in this example.

FIG. 11A shows a plot of voltage as a function of time. FIG. 11B shows a plot of current as a function of time.

FIG. 13A provides a representative circuit diagram for the microfluidic device shown in FIG. 7A during chemical mobilization, where the ESI tip will be held at a positive voltage, using an additional resistor to sink current to ground. FIG. 13B shows a representative circuit diagram for the microfluidic device shown in FIG. 7A during chemical mobilization, where the ESI tip will be held at a positive voltage using an additional resistor to sink current to a third power supply. FIG. 13C shows a representative circuit diagram for the microfluidic device shown in FIG. 7A during chemical mobilization, where the ESI tip will be held at a positive voltage using a field-effect transistor (FET) to sink current. FIG. 13D shows a representative circuit diagram for the microfluidic device shown in FIG. 7A during chemical mobilization, where the ESI tip will be held at a positive voltage using a bipolar junction transistor (BJT) to sink current. FIG. 13E provides a representative circuit diagram for the microfluidic device shown in FIG. 7A during chemical mobilization of a separated analyte mixture, where the ESI tip will be held at or close to ground.

FIG. 16A shows an electropherogram of a separated analyte mixture. FIG. 16B shows a mass spectrum for an acidic peak of the separated species. FIG. 16C shows a mass spectrum of the main peak present in the electropherogram of FIG. 16A. FIG. 16D and FIG. 16E show mass spectra of two basic peaks from the electropherogram shown in FIG. 16A.

DETAILED DESCRIPTION

Figure 1:
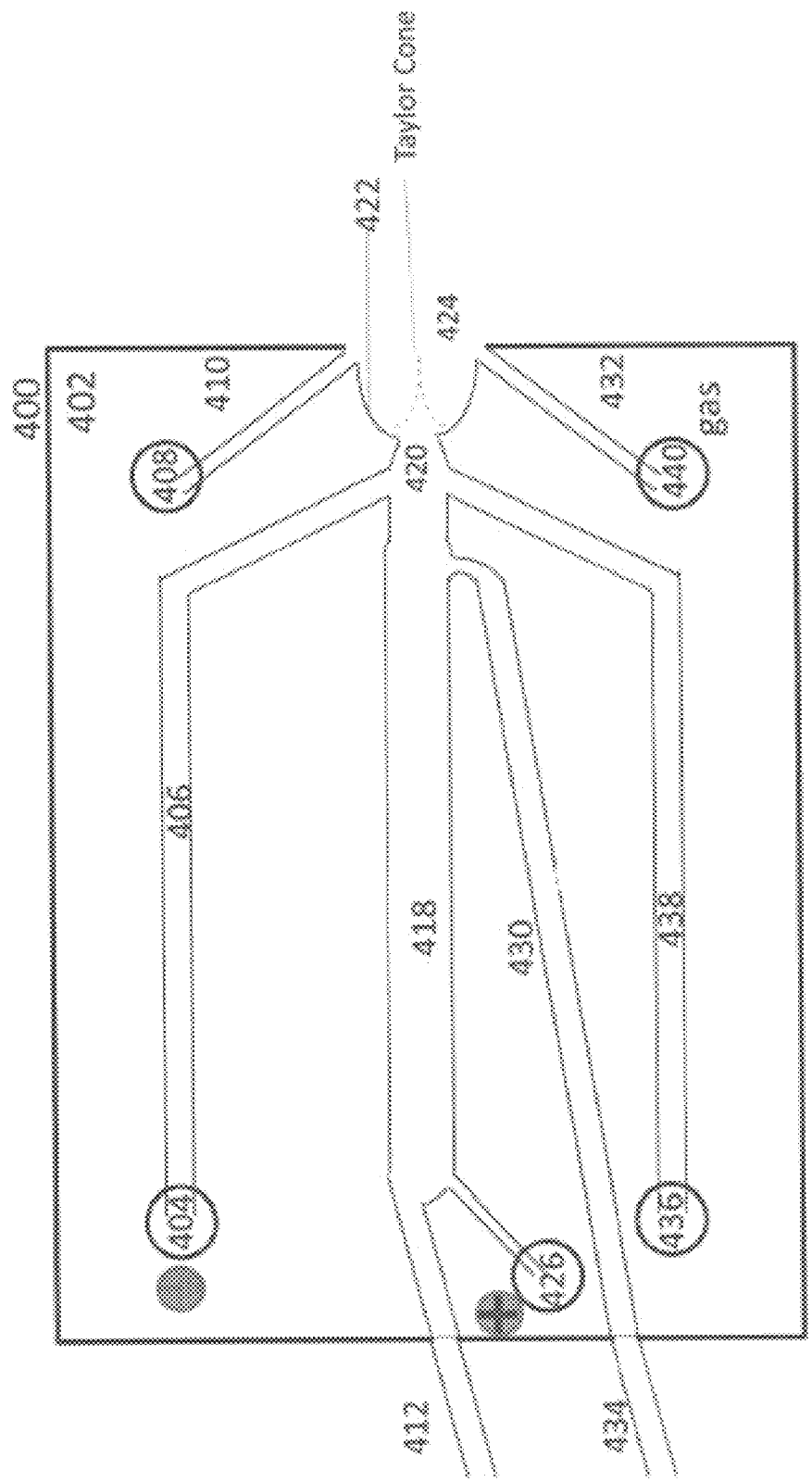
FIG. 1 provides a schematic illustration of a device for isoelectric focusing (IEF) and electrospray ionization (ESI) of an automatically loaded sample, according to one embodiment of the present disclosure.

Some embodiments described herein relate to innovative software and systems for analyzing data from and directing the operation of capillary- and microfluidic-based separation systems integrated with mass spectrometric detection. In some embodiments, analytes are imaged during separation in capillaries or on microfluidic devices, and molecular weight or mass-to-charge ratio is measured in a mass spectrometer post separation. The disclosed methods, devices, systems, and software provide for more accurate characterization of separated analyte peaks, and for achieving improved correlation between chemical separation data and mass spectrometry (MS) data. Also disclosed are methods, devices, systems, and software for improving the quality of electrospray ionization mass spectrometry (ESI-MS) data. The disclosed methods, devices, systems, and software have potential application in a variety of fields including, but not limited to, proteomics research, drug discovery and development, and clinical diagnostics. For example, in some embodiments, the disclosed methods, devices, systems, and software may be utilized for the characterization of biologic and biosimilar pharmaceuticals during development and/or manufacturing, as will be discussed in more detail below. Biologics and biosimilars are a class of drugs which include, for example, recombinant proteins, antibodies, live virus vaccines, human plasma-derived proteins, cell-based medicines, naturally-sourced proteins, antibody-drug conjugates, protein-drug conjugates and other protein drugs.

Microfluidic devices designed to perform any of a variety of chemical separation techniques and that also comprise an electrospray ionization interface for performing downstream mass spectrometry-based analysis are described. In a preferred embodiment, the disclosed devices are designed to perform isoelectric focusing of proteins or other biological macromolecules. In another preferred embodiment, the disclosed devices are designed to be used with imaging techniques. Devices and methods for integration of imaged microfluidic separations with mass spectrometry have been previously described in, for example, published PCT Patent Application Publication No. WO 2017/095813, and U.S. Patent Application Publication No. US 2017/0176386, which are hereby incorporated by reference for all purposes. These applications describe, among other things, systems for performing imaged separation in conjunction with MS analysis. Such microfluidic systems represent a significant advancement in biologics characterization. However, in order for such a system to provide maximal benefit it would be beneficial to have innovative software and systems to aid in the operation of these systems and downstream integration of imaged and MS data, as is disclosed herein.

Accordingly, in a preferred embodiment, the disclosed microfluidic devices may be used in combination with imaging techniques to, for example, make an accurate determination of the isoelectric point (pI) for one or more analytes that have been isoelectrically-separated from a mixture of analytes in a separation channel to form a series of enriched fractions comprising substantially pure individual analyte components (also referred to herein as "peaks" or "bands"). Imaging all or a portion of a separation channel allows one to determine the location of two or more pI standards (or pI markers) that have been injected along with the sample to be separated, and thus allows one to calculate a more accurate pI for each of the separated analyte peaks by extrapolation to determine the local pH. In some embodiments, the imaging of the analyte mixture within a separation channel is performed while the separation is being performed and, optionally, a determination of isoelectric points for one or more of the analytes that are being separated is performed and iteratively updated while the separation is being performed. In some embodiments, the imaging-based determination of isoelectric points for one or more analytes that have been isoelectrically-focused is performed after the separation is complete. In some embodiments, the imaging-based determination of isoelectric points for one or more analytes that have been isoelectrically-focused is performed after the separation is complete, and before the separated analyte mixture has been mobilized towards an electrospray tip. In some embodiments, the imaging-based methods disclosed herein may be used with capillary-based ESI-MS systems rather than microfluidic device-based ESI-MS systems. In some embodiments, the determination of isoelectric points for one or more analyte peaks may be performed by a computer-implemented method.

In another preferred embodiment, the disclosed microfluidic devices may be used in combination with imaging techniques to image separated analyte peaks after mobilization of the separated analyte mixture, i.e., as the peaks move out of the separation channel and towards an electrospray tip. In some embodiments, the imaged mobilization step is the same step as the imaged separation step, such as when implementing a separation step comprising capillary gel electrophoresis, capillary zone electrophoresis, isotachophoresis, capillary electrokinetic chromatography, micellar electrokinetic chromatography, flow counterbalanced capillary electrophoresis, or any other separation technique that separates components of an analyte mixture by differential velocity. In some embodiments, the imaged mobilization step will be analyzed to correlate enriched fractions in the imaged separation with mass spectrum. Imaging of the mobilized analyte peaks may be utilized to, for example, determine a velocity for one or more analyte peaks based on their positions in a series of mobilization images, which may then be used to determine the time point at which the analyte peak(s) will exit the separation channel, or be emitted by the electrospray tip, and may thus be used to correlate mass spectrometer data with specific analyte peaks. In some cases, the velocity of the analyte peak(s) is calculated from the time interval required for the analyte peak to move a certain displacement value (e.g., from a first position to a second position). In some embodiments, imaging of the mobilized analyte peaks may allow direct monitoring of the peak(s) as they travel through a fluid channel and are emitted by the electrospray tip, and may thus be used to directly correlate mass spectrometer data with specific analyte peaks. In some embodiments, the imaging-based methods disclosed herein may be used with capillary-based ESI-MS systems rather than microfluidic device-based ESI-MS systems. In some embodiments, the determination of velocities for one or more analyte peaks, their actual or predicted separation channel exit times, and/or their electrospray emission times, may be performed by a computer-implemented method.

In some embodiments, the mobilization of separated analyte peaks may be initiated by a change in electric field or flow parameters in a microfluidic device. In some embodiments, one or more electrodes connecting a power supply to the microfluidic device will be connected or disconnected to initiate mobilization through a computer-implemented method. In some embodiments, the Taylor cone formed at the electrospray tip may be imaged during the mobilization step. In some embodiments, computer implemented image analysis may be used to identify a stable electrospray operating condition. In some embodiments, the image analysis may be performed by an operator. In some embodiments, the image analysis may be performed using automated image processing software. In some embodiments, one or more of the operating parameters known to affect electrospray performance will be adjusted to regain a stable electrospray operating condition. Examples of operating parameters that may be adjusted include, but are not limited to, electrophoresis voltage, flow rate, distance from the electrospray tip to the MS inlet, MS voltage, and the like. In some embodiments, a computer-implemented method may be used to adjust the electrospray parameters.

In some embodiments, more than one power supply may be used to generate an electrophoresis electric field. In some embodiments, two power supplies having positive polarity may be used. In some embodiments, one or more power supplies may have negative polarity. In some embodiments, the voltage setting on the power supplies may be changed in unison to maintain the same voltage gradient in a separation channel for an electrophoretic separation. In some embodiments, the voltage settings on the power supplies may be changed in order to maintain a constant voltage at an electrospray tip. In some embodiments, the multiple power supplies may be different channels in a single multi-channel power supply. In some embodiments isoelectric focusing may be performed in the separation channel, and the resistance in the channel may increase over time. In some embodiments chemical mobilization may be performed in the separation channel, and the resistance in the channel may decrease over time. In some embodiments, pressure driven mobilization may be performed, and the resistance in the channel may change over time as new reagent is pushed into the channel. In some embodiments, the electrospray tip may be kept at ground. In some embodiments, the electrospray tip may be kept at a specific voltage relative to the mass spectrometer. In some embodiments, the electrospray tip may be kept at a specific voltage relative to ground. In some embodiments, a computer-implemented method may adjust voltages to maintain a constant electric field strength in the separation channel (or a constant voltage drop between anode and cathode), and a constant voltage at the electrospray tip. In some embodiments, the voltage at the tip may be measured using a volt-meter. In some embodiments, the voltage at the tip may be measured using an electrode positioned at or inside the tip. In some embodiments, an additional power supply may be set to 0 µA using current control and used as a volt-meter to read the tip voltage. In some embodiments, a computer implemented method will read the value of the voltage at the tip, and adjust voltages to maintain a constant electric field strength in the separation channel (or a constant voltage drop between anode and cathode), and maintain a constant voltage at the tip. In some embodiments, a computer implemented method will calculate the voltage at the ESI tip based on current flow through the separation electric field circuit. In some embodiments, the voltage drop across the separation channel will be adjusted such that a constant power or a maximum power is applied in the separation channel, where the power applied in the separation channel is calculated as:

$$\text{power} = \text{voltage across separation channel} \times \text{current in separation channel}$$

where the current can be measured constantly or periodically during separation and the current measurements can be used to adjust the voltage across the separation channel. This method of controlling the power in the separation channel may be useful for managing temperature effects in the separation channel.

Figure 14A:
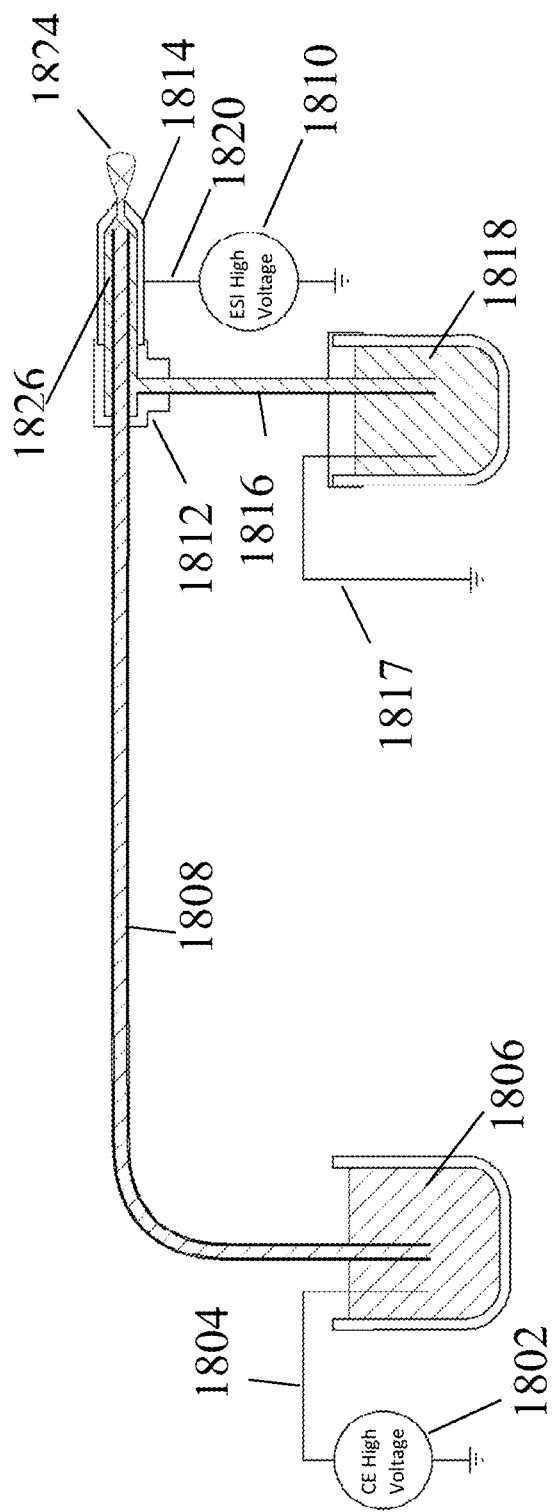
FIG. 14A provides a representative diagram of a capillary junction sprayer.

In some embodiments, the separation path will be a length of linear coated or uncoated capillary, tube or line with the inlet inserted in a vial containing an acidic anolyte and positive electrode or basic catholyte and negative electrode. In some embodiments, the outlet of the separation path will be inserted into junction sprayer. In some embodiments, the junction sprayer houses both a Tee for a secondary tube, line, or capillary that can introduce another conductive make-up solution to the capillary outlet providing for a liquid to liquid electrical contact and liquid flow to support electrospray and transport analytes emerging from the separation channel to the tip for introduction into a mass spectrometer by electrospray ionization. In some embodiments, the system may be configured with anolyte and positive electrode at the separation path inlet and the junction or distal portion of the separation path may be loaded with catholyte just prior to focusing. After focusing is completed, a mobilization agent with competing anion may be introduced into the junction by either hydrodynamic or electroosmotic force. In some embodiments, the separation path inlet may be immersed in a vial with catholyte and a negative electrode, and the junction or distal portion of the capillary may be loaded with anolyte just prior to focusing. After focusing is completed, a mobilization agent with competing cation may be introduced into the junction by either hydrodynamic or electroosmotic force. In some embodiments, the separation channel will be a length of a linear capillary, with one end inserted into an anolyte reservoir connecting the capillary to a positive electrode and the other end inserted into a catholyte reservoir connecting the capillary to a negative electrode for isoelectric focusing. In some embodiments, after focusing, the catholyte end of the capillary will be removed from the catholyte and inserted into a junction sprayer (e.g., a microvial sprayer) in proximity to a mass spectrometer, as shown in FIG. 14A. In some embodiments, the junction sprayer may provide a volume of mobilizer to charge analyte in ESI and mobilize focused analytes. In some embodiments, the junction sprayer may provide electrical connection to complete mobilization circuit. In some embodiments, the voltage at the anolyte and junction sprayer will be adjusted so that the change in voltage (ΔV) or electric field between the anolyte and junction sprayer remains constant, and the voltage at the ESI tip remains constant.

In some embodiments, the separation channel (e.g., capillary) comprises a microvial, which may facilitate the transfer of the mobilized effluent to the ESI. The microvial may be a part of the capillary or may be appended and/or fused to the separation channel. The microvial may be a part of the ESI tip. In some instances, the microvial may comprise or be a part of a junction sprayer. The microvial may provide a fluid flow path (e.g., for sheath fluid) in a portion of the channel or at the ESI tip.

In some embodiments, one power supply may be connected to a resistor to create a current sink. In some embodiments, the resistor may sink current by connecting the electrophoresis circuit to ground. In some embodiments, the resistor is a field effect transistor (FET) adjustable resistor. In some embodiments, the resistor may be a precision variable resistor, a relay resistor network, a resistor ladder, or any other resistive element capable of providing a path to sink current. In some embodiments the current sink can be a FET, where the FET is controlled such that it provides a constant current flow through the FET or can be controlled to function as an open or as a short circuit when required. In some embodiments, a bipolar junction transistor (BJT) can be used for the current sink function. In some embodiments, the resistor may sink current by connecting the electrophoresis circuit to a current sinking power supply. In some embodiments, the voltage setting of the current-sinking power supply will be adjusted as the resistance in the separation channel changes over time. In some embodiments, the voltage on the current-sinking power supply will be adjusted to maintain constant current across the resistor. In some embodiments, a resistor, or set of resistors, resistive circuit, or the like, may be used as a current sink In some embodiments, the mass-to-charge (m/z) range being scanned may be changed during the mobilization/ESI step. In some embodiments, a computer-implemented method may be used to switch between a high m/z range and low m/z range. In some embodiments, a mass spectrum in the one m/z range may be used as an internal standard for the separation of the analyte in a different mass range. This spectrum may comprise data for free solution isoelectric gradient ampholytes, which may be used as a standard for isoelectric point (pI), or this spectrum may comprise data for electrophoretic mobility standards which may be used as a standard in electrophoresis, e.g., capillary zone electrophoresis. In some instances, this spectrum may comprise data for any molecule which can be resolved in the separation step, for example, by pI, charge to mass ratio, reputation through gel, electrophoretic mobility, etc., which is in a different mass range than the analyte of interest.

A system of the present disclosure may comprise one or more of: (i) a capillary or microfluidic device designed to perform an analyte separation, e.g., an isoelectric focusing-based separation, that provides an electrospray interface with a mass spectrometer, (ii) a mass spectrometer, (iii) an imaging device or system, (iv) a processor or computer, (v) software for coordinating the operation of the capillary- or microfluidic device-based analyte separation with image acquisition, (vi) software for processing images and determining the position(s) of one or more pI standards or analyte peaks in a separation channel while the separation is being performed, after the separation is complete, or after mobilization of the pI standards and analyte peaks towards the electrospray tip; (vii) software for processing images and determining a velocity, an exit time, and/or an electrospray emission time for one or more pI standard or analyte peaks, (viii) software for simultaneously or alternately acquiring images of the separation channel to monitor a position of an analyte peak and the Taylor cone existing between the electrospray tip and the inlet to the mass spectrometer to monitor electrospray performance; (ix) software for processing images of a Taylor cone and adjusting one or more of the position of the electrospray tip relative to the mass spectrometer inlet, the fluid flow through the electrospray tip, the voltage between the electrospray tip and the mass spectrometer, or any combination thereof, to affect a change in a quality of the mass spectrometer data; (x) software for controlling the collection of mass spectrometer data for individual analyte peaks emitted from the electrospray interface, where the data collection mode for the mass spectrometer is alternated between a high mass scan and a low mass scan; (xi) software for reading the voltage at the electrospray tip and adjusting separation channel voltages to maintain constant field strength in the channel (or a constant voltage drop between anode and cathode), while maintaining a constant voltage on the tip; or any combination thereof. In some embodiments, the system may comprise an integrated system in which a selection of these functional components are packaged in a fixed configuration. In some embodiments, the system may comprise a modular system in which the selection of functional components may be changed in order to reconfigure the system for new applications. In some embodiments, some of these functional system components, e.g., capillaries or microfluidic devices, are replaceable or disposable components.

It is to be understood that both the foregoing general overview and the following description are exemplary and explanatory only, and are not restrictive of the methods and devices described herein.

Definitions

Unless otherwise defined, all technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated. Similarly, the phrases "comprise", "comprises", "comprising", "include", "includes", and "including" are not intended to be limiting.

As used herein, the term "about" a number refers to that number plus or minus 10% of that number. The term "about" when used in the context of a range refers to that range minus 10% of its lowest value and plus 10% of its greatest value.

Analytes: As noted above, the disclosed methods, devices, systems, and software enable more accurate characterization of separated analyte peaks, and improved correlation between chemical separation data and mass spectrometry data. In some instances, these analytes can be, for example, released glycans, carbohydrates, lipids or derivatives thereof (e.g., extracellular vesicles, liposomes, etc.), DNA, RNA, intact proteins, digested proteins, protein complexes, antibody-drug conjugates, protein-drug conjugates, peptides, metabolites, organic compounds, or other biologically relevant molecules, or any combination thereof. In some instances, these analytes can be small molecule drugs. In some instances, these analytes can be protein molecules in a protein mixture, such as a biologic protein pharmaceutical and/or a lysate collected from cells isolated from culture or in vivo.

Samples: The disclosed methods, devices, systems, and software may be used for separation and characterization of analytes obtained from any of a variety of biological or non-biological samples. Examples include, but are not limited to, tissue samples, cell culture samples, whole blood samples (e.g., venous blood, arterial blood, or capillary blood samples), plasma, serum, saliva, interstitial fluid, urine, sweat, tears, protein samples derived from industrial enzyme or biologic drug manufacturing processes, environmental samples (e.g., air samples, water samples, soil samples, surface swipe samples), and the like. In some embodiments, the samples may be processed using any of a variety of techniques known to those of skill in the art prior to analysis using the disclosed methods and devices for integrated chemical separation and mass spectrometric characterization. For example, in some embodiments the samples may be processed to extract proteins or nucleic acids. Samples may be collected from any of a variety of sources or subjects, e.g., bacteria, virus, plants, animals, or humans.

Sample volumes: In some embodiments of the disclosed methods and devices, the miniaturization that may be achieved through the use of microfabrication techniques enables the processing of very small sample volumes. In some embodiments, the sample volume used for analysis may range from about 0.1 µl to about 1 ml. In some embodiments, the sample volume used for analysis may be at least 0.1 µl, at least 1 µl, at least 2.5 µl, at least 5 µl, at least 7.5 µl, at least 10 µl, at least 25 µl, at least 50 µl, at least 75 µl, at least 100 µl, at least 250 µl, at least 500 µl, at least 750 µl, or at least 1 ml. In some embodiments, the sample volume used for analysis may be at most 1 ml, at most 750 µl, at most 500 µl, at most 250 µl, at most 100 id, at most 75 µl, at most 50 µl, at most 25 µl, at most 10 µl, at most 7.5 µl, at most 5 µl, at most 2.5 µl, at most 1 µl, or at most 0.1 µl. Any of the lower and upper values described in this paragraph may be combined to form a range included within the present disclosure, for example, in some embodiments the sample volume used for analysis may range from about 5 µl to about 500 µl. Those of skill in the art will recognize that sample volume used for analysis may have any value within this range, e.g., about 10 µl.

Separation techniques: The disclosed methods, devices, systems, and software may utilize any of a variety of analyte separation techniques known to those of skill in the art. For example, in some embodiments, the imaged separation may be an electrophoretic separation, such as, isoelectric focusing, capillary gel electrophoresis, capillary zone electrophoresis, isotachophoresis, capillary electrokinetic chromatography, micellar electrokinetic chromatography, flow counterbalanced capillary electrophoresis, electric field gradient focusing, dynamic field gradient focusing, and the like, that produces one or more separated analyte fractions from an analyte mixture.

Capillary isoelectric focusing (CIEF): In some embodiments, the separation technique may comprise isoelectric focusing (IEF), e.g., capillary isoelectric focusing (CIEF). Isoelectric focusing (or "electrofocusing") is a technique for separating molecules by differences in their isoelectric point (pI), i.e., the pH at which they have a net zero charge. CIEF involves adding ampholyte (amphoteric electrolyte) solutions to a sample channel between reagent reservoirs containing an anode or a cathode to generate a pH gradient within a separation channel (i.e., the fluid channel connecting the electrode-containing wells) across which a separation voltage is applied. The ampholytes can be solution phase or immobilized on the surface of the channel wall. Negatively charged molecules migrate through the pH gradient in the medium toward the positive electrode while positively charged molecules move toward the negative electrode. A protein (or other molecule) that is in a pH region below its isoelectric point (pI) will be positively charged and so will migrate towards the cathode (i.e., the negatively charged electrode). The protein's overall net charge will decrease as it migrates through a gradient of increasing pH (due, for example, to protonation of carboxyl groups or other negatively charged functional groups) until it reaches the pH region that corresponds to its pI, at which point it has no net charge and so migration ceases. As a result, a mixture of proteins separates based on their relative content of acidic and basic residues and becomes focused into sharp stationary bands with each protein positioned at a point in the pH gradient corresponding to its pI. The technique is capable of extremely high resolution with proteins differing by a single charge being fractionated into separate bands. In some embodiments, isoelectric focusing may be performed in a separation channel that has been permanently or dynamically coated, e.g., with a neutral and hydrophilic polymer coating, to eliminate electroosmotic flow (EOF). Examples of suitable coatings include, but are not limited to, amino modifiers, hydroxypropylcellulose (HPC) and polyvinylalcohol (PVA), Guarant® (Alcor Bioseparations), linear polyacrylamide, polyacrylamide, dimethyl acrylamide, polyvinylpyrrolidine (PVP), methylcellulose, hydroxyethylcellulose (HEC), hydroxyprpylmethylcellulose (HPMC), triethylamine, proylamine, morpholine, diethanolamine, triethanolamine, diaminopropane, ethylenediamine, chitosan, polyethyleneimine, cadaverine, putrescine, spermidine, diethylenetriamine, tetraethylenepentamine, cellulose, dextran, polyethylene oxide (PEO), cellulose acetate, amylopectin, ethylpyrrolidine methacrylate, dimethyl methacrylate, didodecyldimethylammonium bromide, Brij 35, sulfobetains, 1,2-dilauryloylsn-phosphatidylcholine, 1,4-didecyl-1,4-diazoniabicyclo[2,2,2]octane dibromide, agarose, poly(Nhydroxyethylacrylamide), pole-323, hyperbranched polyamino esters, pullalan, glycerol, adsorbed coatings, covalent coatings, dynamic coatings, etc. In some embodiments, isoelectric focusing may be performed (e.g., in uncoated separation channel) using additives such as methylcellulose, glycerol, urea, formamide, surfactants (e.g., Triton-X 100, CHAPS, digitonin) in the separation medium to significantly decrease the electroosmotic flow, allow better protein solubilization, and limit diffusion inside the capillary of fluid channel by increasing the viscosity of the electrolyte.

As noted above, the pH gradient used for capillary isoelectric focusing techniques is generated through the use of ampholytes, i.e., amphoteric molecules that contain both acidic and basic groups and that exist mostly as zwitterions within a certain range of pH. The portion of the electrolyte solution on the anode side of the separation channel is known as an "anolyte". That portion of the electrolyte solution on the cathode side of the separation channel is known as a "catholyte". A variety of electrolytes may be used in the disclosed methods and devices including, but not limited to, phosphoric acid, sodium hydroxide, ammonium hydroxide, glutamic acid, lysine, formic acid, dimethylamine, triethylamine, acetic acid, piperidine, diethylamine, and/or any combination thereof. The electrolytes may be used at any suitable concentration, such as 0.0001%, 0.001%, 0.01%, 0.1%, 1%, 10%, 20%, 30%, 40%, 50%, 60%, 70%, 80%, 90%, etc. The concentration of the electrolytes may be at least 0.0001%, 0.001%, 0.01%, 0.1%, 1%, 10%, 20%, 30%, 40%, 50%, 60%, 70%, 80%, 90%. The concentration of the electrolytes may be at most 90%, 80%, 70%, 60%, 50%, 40%, 30%, 20%, 10%, 1%, 0.1%, 0.01%, 0.001%, 0.0001%. A range of concentrations of the electrolytes may be used, e.g., 0.1%-2%. Ampholytes can be selected from any commercial or non-commercial carrier ampholytes mixtures (e.g., Servalyt pH 4-9 (Serva, Heildelberg, Germany), Beckman pH 3-10 (Beckman Instruments, Fullerton, Calif., USA), Ampholine 3.5-9.5 and Pharmalyte 3-10 (both from General Electric Healthcare, Orsay, France), AESlytes (AES), FLUKA ampholyte (Thomas Scientific, Swedesboro, N.J.), Biolyte (Bio-Rad, Hercules, Calif.)), and the like. Carrier ampholyte mixtures may comprise mixtures of small molecules (about 300-1,000 Da) containing multiple aliphatic amino and carboxylate groups that have closely spaced pI values and good buffering capacity. In the presence of an applied electric field, carrier ampholytes partition into smooth linear or non-linear pH gradients that increase progressively from the anode to the cathode.

Any of a variety of pI standards may be used in the disclosed methods and devices for calculating the isoelectric point for separated analyte peaks. For example, pI markers generally used in CIEF applications, e.g., protein pI markers and synthetic small molecule pI markers, may be used. In some instances, protein pI markers may be specific proteins with commonly accepted pI values. In some instances, the pI markers may be detectable, e.g., via imaging. A variety or combination of protein pI markers or synthetic small molecule pI markers that are commercially available, e.g., the small molecule pI markers available from Advanced Electrophoresis Solutions, Ltd. (Cambridge, Ontario, Canada), ProteinSimple, the peptide library designed by Shimura, and Slais dyes (Alcor Biosepartions), may be used.

Mobilization techniques: In some embodiments, e.g., in those instances where isoelectric focusing is employed, the separated analyte bands may be mobilized towards an end of the separation channel that interfaces with a downstream analytical device, e.g., an electrospray ionization interface with a mass spectrometer. In some embodiments, e.g., in those instances where capillary gel electrophoresis, capillary zone electrophoresis, isotachophoresis, capillary electrokinetic chromatography, micellar electrokinetic chromatography, flow counterbalanced capillary electrophoresis, or any other separation technique that separates components of an analyte mixture by differential velocity is employed, the separation step may be viewed as the mobilization step.

In some embodiments, mobilization of the analyte bands may be implemented by applying hydrodynamic pressure to one end of the separation channel. In some embodiments, mobilization of the analyte bands may be implemented by orienting the separation channel in a vertical position so that gravity may be employed. In some embodiments, mobilization of the analyte bands may be implemented using EOF-assisted mobilization. In some embodiments, mobilization of the analyte bands may be implemented using chemical mobilization. In some embodiments, any combination of these mobilization techniques may be employed.

In one embodiment, the mobilization step for isoelectrically-focused analyte bands comprises chemical mobilization. Compared with pressure-based mobilization, chemical mobilization has the advantage of exhibiting minimal band broadening by overcoming the hydrodynamic parabolic flow profile induced by the use of pressure. Chemical mobilization may be implemented by introducing either the inlet or outlet of a separation path containing a completely or partially focused pH gradient to a conductive solution with an ion that competes with either hydronium or hydroxyl for electrophoresis into the separation path. This results in the stepwise electrokinetic displacement of the pH gradient components by disrupting the approximate zero net charge state. In the case of cathodic chemical mobilization, the supply of hydroxyls, the catholyte solution, may be replaced with a mobilization solution containing a competing anion. The competing anion can cause a drop in pH in the separation path developing a positive charge on the pH gradient components allowing them to migrate towards the cathode. Correspondingly, in anodic mobilization the supply of hydroniums, the anolyte solution is replaced with a mobilization solution containing a competing cation which increases the pH in the separation developing a negative charge of the pH gradient components allowing them to migrate towards the anode. In some embodiments, cathodic mobilization may be initiated using acidic electrolytes such as formic acid, acetic acid, carbonic acid, phosphoric acid and the like, at any suitable concentration. In some embodiments, anodic mobilization may be initiated using basic electrolytes such as ammonium hydroxide, dimethylamine, diethylamine, piperidine, sodium hydroxide and the like. In some embodiments, chemical mobilization may be initiated by adding salt, such as sodium chloride, or any other salt to the anolyte or catholye solution.

In a preferred embodiment, a chemical mobilization step may be initiated within a microfluidic device designed to integrate CIEF with ESI-MS by changing an electric field within the device to electrophorese a mobilization electrolyte into the separation channel. In some embodiments, the change in electric field may be implemented by connecting or disconnecting one or more electrodes attached to one or more power supplies, wherein the one or more electrodes are positioned in reagent wells on the device or integrated with fluid channels of the device. In some embodiments, the connecting or disconnecting of one or more electrodes may be controlled using a computer-implemented method and programmable switches, such that the timing and duration of the mobilization step may be coordinated with the separation step, the electrospray ionization step, and/or mass spectrometry data collection. In some embodiments, the disconnecting of one or more electrodes from the separation circuit may be implemented by using current control and setting the current to 0 µA.

Capillary zone electrophoresis (CZE): In some embodiments, the separation technique may comprise capillary zone electrophoresis, a method for separation of charged analytes in solution in an applied electric field. The net velocity of charged analyte molecules is influenced both by the electroosmotic flow (EOF) mobility, $\mu_{EOF}$, exhibited by the separation system and the electrophoretic mobility, $\mu_{EP}$, for the individual analyte (dependent on the molecule's size, shape, and charge), such that analyte molecules exhibiting different size, shape, or charge exhibit differential migration velocities and separate into bands.

Capillary gel electrophoresis (CGE): In some embodiments, the separation technique may comprise capillary gel electrophoresis, a method for separation and analysis of macromolecules (e.g., DNA, RNA, and proteins) and their fragments based on their size and charge. The method comprises use of a gel-filled separation channel, where the gel acts as an anti-convective and/or sieving medium during electrophoretic movement of charged analyte molecules in an applied electric field. The gel functions to suppress thermal convection caused by application of the electric field, and also acts as a sieving medium that retards the passage of molecules, thereby resulting in a differential migration velocity for molecules of different size or charge.

Capillary isotachophoresis (CITP): In some embodiments, the separation technique may comprise capillary isotachophoresis, a method for separation of charged analytes that uses a discontinuous system of two electrolytes (known as the leading electrolyte and the terminating electrolyte) within a capillary or fluid channel of suitable dimensions. The leading electrolyte may contain ions with the highest electrophoretic mobility, while the terminating electrolyte may contain ions with the lowest electrophoretic mobility. The analyte mixture (i.e., the sample) to be separated can be sandwiched between these two electrolytes, and application of an electric field results in partitioning of the charged analyte molecules within the capillary or fluid channel into closely contiguous zones in order of decreasing electrophoretic mobility. The zones move with constant velocity in the applied electric field such that a detector, e.g., a conductivity detector, photodetector, or imaging device, may be utilized to record their passage along the separation channel. Unlike capillary zone electrophoresis, simultaneous determination or detection of anionic and cationic analytes is not feasible in a single analysis performed using capillary isotachophoresis.

Capillary electrokinetic chromatography (CEC): In some embodiments, the separation technique may comprise capillary electrokinetic chromatography, a method for separation of analyte mixtures based on a combination of liquid chromatographic and electrophoretic separation methods. CEC offers both the efficiency of capillary electrophoresis (CE) and the selectivity and sample capacity of packed capillary high performance liquid chromatography (HPLC). Because the capillaries used in CEC are packed with HPLC packing materials, the wide variety of analyte selectivities available in HPLC are also available in CEC. The high surface area of these packing materials enables CEC capillaries to accommodate relatively large amounts of sample, making detection of the subsequently eluted analytes a somewhat simpler task than it is in capillary zone electrophoresis (CZE).

Micellar electrokinetic chromatography (MEKC): In some embodiments, the separation technique may comprise micellar electrokinetic chromatography, a method for separation of analyte mixtures based on differential partitioning between surfactant micelles (a pseudo-stationary phase) and a surrounding aqueous buffer solution (a mobile phase). In MEKC, the buffer solution may contain a surfactant at a concentration that is greater than the critical micelle concentration (CMC), such that surfactant monomers are in equilibrium with micelles. MEKC may be performed in open capillaries or fluid channels using alkaline conditions to generate a strong electroosmotic flow. A variety of surfactants, e.g., sodium dodecyl sulfate (SDS) may be used in MEKC applications. For example, the anionic sulfate groups of SDS cause the surfactant and micelles to have electrophoretic mobility that is counter to the direction of the strong electroosmotic flow. As a result, the surfactant monomers and micelles migrate slowly, though their net movement is still in the direction of the electoosmotic flow, i.e., toward the cathode. During MEKC separations, analytes may distribute between the hydrophobic interior of the micelle and hydrophilic buffer solution. Hydrophilic analytes that are insoluble in the micelle interior migrate at the electroosmotic flow velocity, $u_o$, and will be detected at the retention time of the buffer, $t_M$. Hydrophobic analytes that solubilize completely within the micelles migrate at the micelle velocity, $u_c$, and elute at the final elution time, $t_c$.

Flow counterbalanced capillary electrophoresis (FCCE): In some embodiments, the separation technique may comprise flow counterbalanced capillary electrophoresis, a method for increasing the efficiency and resolving power of capillary electrophoresis that utilizes a pressure-induced counter-flow to actively retard, halt, or reverse the electrokinetic migration of an analyte through a capillary. By retarding, halting, or moving the analytes back and forth across a detection window, the analytes of interest may effectively be confined to the separation channel for much longer periods of time than under normal separation conditions, thereby increasing both the efficiency and the resolving power of the separation.

Separation times and separation resolution: In general, the separation time required to achieve complete separation will vary depending on the specific separation technique and operational parameters (e.g., separation channel length, microfluidic device design, buffer compositions, applied voltages, etc.) utilized. In some embodiments, the software will determine when separation is complete based on an imaging-based analysis of analyte peaks, as described in co-pending U.S. patent application Ser. No. 16/261,382. In some embodiments, the separation time may range from about 0.1 minutes to about 30 minutes. In some embodiments, the separation time may be at least 0.1 minutes, at least 0.5 minutes, at least 1 minute, at least 5 minutes, at least 10 minutes, at least 15 minutes, at least 20 minutes, at least 25 minutes, or at least 30 minutes. In some embodiments, the separation time may be at most 30 minutes, at most 25 minutes, at most 20 minutes, at most 15 minutes, at most 10 minutes, at most 5 minutes, at most 1 minute, at most 0.5 minutes, or at most 0.1 minutes. Any of the lower and upper values described in this paragraph may be combined to form a range included within the present disclosure, for example, in some embodiments the separation time may range from about 1 minute to about 20 minutes. The separation time may have any value within this range, e.g., about 7 minutes.

Similarly, the separation efficiency and resolution achieved using the disclosed methods and devices may vary depending on the specific separation technique and operational parameters (e.g., separation channel length, microfluidic device design, buffer compositions, applied voltages, etc.) utilized. In some embodiments, the separation efficiency (e.g., number of theoretical plates) achieved may range from about 1,000 to 1,000,000. In some instances, the separation efficiency may be at least 1,000, at least 5,000, at least 10,000, at least 20,000, at least 30,000, at least 40,000, at least 50,000, at least 60,000, at least 70,000, at least 80,000, at least 90,000, at least 100,000, at least 200,000, at least 300,000, at least 400,000, at least 500,000, at least 600,000, at least 700,000, at least 800,000, at least 900,000, or at least 1,000,000. The separation resolution of efficiency may vary, depending on one or more properties (e.g., molecular mass, diffusivity, electrophoretic or isoelectric mobility, etc.) of the analytes in the mixture.

Microfluidic device design and fabrication: In some embodiments of the disclosed methods, devices, and systems, the separation of analytes from a mixture and, optionally, their subsequent analysis using ESI-MS may be performed using a microfluidic device designed to integrate one or more sample preparation steps (e.g., filtration, pre-concentration, or extraction steps, and the like) and/or separation steps (e.g., as outlined above) with an electrospray ionization step.

In some embodiments, the disclosed microfluidic device may comprise one or more sample or reagent ports (also referred to as inlet ports, sample wells, or reagent wells), one or more waste ports (also referred to as outlet ports), one or more fluid channels connecting said inlet and outlet ports with each other or with intermediate fluid channels (e.g., separation channels), or any combination thereof. In some embodiments, the disclosed microfluidic devices may further comprise one or more reaction chambers or mixing chambers, one or more microfabricated valves, one or more microfabricated pumps, one or more vent structures, one or more membranes (e.g., filtration membranes), one or more micro-column structures (e.g., fluid channels or modified fluid channels that have been packed with a chromatographic separation medium), or any combination thereof.

In a preferred embodiment, the disclosed microfluidic devices incorporate an electrospray orifice or electrospray tip to provide an electrospray ionization interface with a mass spectrometer. One non-limiting example of such an interface is described in co-pending U.S. Patent Application Publication Nos. U.S. 2017/0176386 A1 and U.S. 2018/0003674 A1. FIG. 1 illustrates one non-limiting example of a microfluidic device designed to perform isoelectric focusing followed by ESI-MS characterization. The fluid channel network shown in FIG. 1 is fabricated from a plate of soda lime glass, which has very low transmission of 280 nm light using a standard photolithographic etching technique. The depth of the separation (or enrichment) channel 418 is the same as the thickness of the glass layer 402, i.e., the enrichment channel 418 passes all the way from the top to bottom of glass plate 402. The device 400 can be illuminated by a light source disposed on one side of device 400 and imaged by a detector disposed on an opposite side of device 400. Because substrate 402 is opaque, but enrichment channel 418 defines an optical slit, the substrate 402 can block light that does not pass through the enrichment channel 418, blocking stray light and improving resolution of the imaging process. The glass layer 402 is sandwiched between two fused silica plates, which are transmissive (e.g., transparent) to 280 nm light. The top plate contains through holes for the instrument and user to interface with the channel network, while the bottom plate is solid. The three plates are bonded together at 520° C. for 30 minutes. The inlet and outlet tubing is manufactured from cleaved capillaries (100 µm ID, Polymicro) bonded to the channel network. The operation of this device in performing isoelectric focusing of proteins and subsequent mass spectrometry characterization will be described in Example 1 below.

Any of a variety of fluid actuation mechanisms known to those of skill in the art may be used to control fluid flow of samples and reagents through the device. Examples of suitable fluid actuation mechanisms for use in the disclosed methods, devices, and systems include, but are not limited to, application of positive or negative pressure to one or more inlet ports or outlet ports, gravitational or centrifugal forces, electrokinetic forces, electrowetting forces, or any combination thereof. In some embodiments, positive or negative pressure may be applied directly, e.g., through the use of mechanical actuators or pistons that are coupled to the inlet and/or outlet ports to actuate flow of the sample or reagents through the fluidic channels. In some embodiments, the mechanical actuators or pistons may exert force on a flexible membrane or septum that is used to seal the inlet and/or outlet ports. In some embodiments, positive or negative pressure may be applied indirectly, e.g., through the use of pressurized gas lines or vacuum lines connected with one or more inlet and/or outlet ports. In some embodiment, pumps, e.g., programmable syringe pumps, HPLC pumps, or peristaltic pumps, connected with one or more inlet and/or outlet ports may be used to drive fluid flow. In some embodiments, electrokinetic forces and/or electrowetting forces may be applied through the use of electric field and control of surface properties within the device. Electric fields may be applied by means of electrodes inserted into one or more inlet and/or outlet ports, or by means of electrodes integrated into one or more fluid channels within the device. The electrodes may be connected with one or more DC or AC power supplies for controlling voltages and/or currents within the device.

In general, the inlet ports, outlet ports, fluid channels, or other components of the disclosed microfluidic devices, including the main body of the device, may be fabricated using any of a variety of materials, including, but not limited to glass, fused-silica, silicon, polycarbonate, polymethylmethacrylate, cyclic olefin copolymer (COC) or cyclic olefin polymer (COP), polydimethylsiloxane (PDMS), or other elastomeric materials. Suitable fabrication techniques will generally depend on the choice of material, and vice versa. Examples include, but are not limited to, CNC machining, photolithography and chemical etching, laser photo-ablation, injection molding, hot embossing, die cutting, 3D printing, and the like. In some embodiments, the microfluidic device may comprise a layered structure in which, for example, a fluidics layer comprising fluid channels is sandwiched between an upper layer and/or a lower layer to seal the channels. The upper layer and/or lower layer may comprise openings that align with fluid channels in the fluidics layer to create inlet and/or outlet ports, etc. Two or more device layers may be clamped together to form a device which may be disassembled, or may be permanently bonded. Suitable bonding techniques will generally depend on the choice of materials used to fabricate the layers. Examples include, but are not limited to, anodic bonding, thermal bonding, laser welding, or the use of curable adhesives (e.g., thermally- or photo-curable adhesives).

In some embodiments, all or a portion of the inlet ports, outlet ports, or fluid channels within the microfluidic device may comprise a surface coating used to modify the electroosmotic flow properties (e.g., HPC or PVA coatings) and/or hydrophobicity/hydrophilicity properties (e.g., polyethylene glycol (PEG) coatings) of the inlet port, outlet port, or fluid channel walls.

The inlet and/or outlet ports of the disclosed devices can be fabricated in a variety of shapes and sizes. Appropriate inlet and/or outlet port geometries include, but are not limited to, spherical, cylindrical, elliptical, cubic, conical, hemispherical, rectangular, or polyhedral (e.g., three dimensional geometries comprised of several planar faces, for example, rectangular cuboid, hexagonal columns, octagonal columns, inverted triangular pyramids, inverted square pyramids, inverted pentagonal pyramids, inverted hexagonal pyramids, or inverted truncated pyramids), or any combination thereof.

Inlet and/or outlet port dimensions may be characterized in terms of an average diameter and depth. As used herein, the average diameter of the inlet or outlet port refers to the largest circle that can be inscribed within the planar cross-section of the inlet and/or outlet port geometry. In some embodiments of the present disclosure, the average diameter of the inlet and/or outlet ports may range from about 0.1 mm to about 10 mm. In some embodiments, the average diameter of the inlet and/or outlet ports may be at least 0.5 mm, at least 1 mm, at least 2 mm, at least 4 mm, at least 8 mm, or at least 10 mm. In some embodiments, the average diameter may be at most 10 mm, at most 8 mm, at most 6 mm, at most 4 mm, at most 2 mm, at most 1 mm, or at most 0.5 mm. Any of the lower and upper values described in this paragraph may be combined to form a range included within the present disclosure, for example, in some embodiments, the average diameter may range from about 2 mm to about 8 mm. Those of skill in the art will recognize that the average diameter of the inlet and/or outlet ports have any value within this range, e.g., about 5.5 mm.

In some embodiments, the depth of the inlet and/or outlet ports (e.g., the sample or reagent wells) may range from about 5 µm to about 500 µm. In some embodiments, the depth may be at least 5 µm, at least 10 µm, at least 25 µm, at least 50 µm, at least 75 µm, at least 100 µm, at least 200 µm, at least 300 µm, at least 400 µm, or at least 500 µm. In some embodiments, the depth may be at most 500 µm, at most 400 µm, at most 300 µm, at most 200 µm, at most 100 µm, at most 50 µm, at most 25 µm, at most 10 µm, or at most 5 µm. Any of the lower and upper values described in this paragraph may be combined to form a range included within the present disclosure, for example, in some embodiments the depth of the inlet and/or outlet ports may range from about 50 µm to about 200 µm. Those of skill in the art will recognize that the depth may have any value within this range, e.g., about 130 µm. In some embodiments, the depth of the inlet and/or outlet ports (e.g., the sample or reagent wells) may range from about 500 µm to about 50 mm. In some embodiments, the depth may be at least 1 mm, at least 5 mm, at least 10 mm, at least 15 mm, at least 20 mm, or at least 50 mm. In some embodiments, the depth may be at most 50 mm, at most 20 mm, at most 15 mm, at most 10 mm, at most 5 mm, or at most 1 mm. Any of the lower and upper values described in this paragraph may be combined to form a range included within the present disclosure, for example, in some embodiments the depth of the inlet and/or outlet ports may range from about 50 µm to about 5 mm.

In some embodiments, the fluid channels of the disclosed devices may have any of a variety of cross-sectional geometries, such as square, rectangular, circular, and the like. In general, the cross-sectional geometry of the fluid channels will be dependent on the fabrication technique used to create them, and vice versa. In some embodiments, a cross-sectional dimension of the fluid channels (e.g., the height, the width, or an average diameter for a fluid channel of non-rectangular cross-section, where the average diameter is defined as the diameter of the largest circle that can be inscribed within the cross-sectional geometry of the fluid channel) may range from about 5 µm to about 500 µm. In some embodiments, a dimension the fluid channel may be at least 5 µm, at least 10 µm, at least 25 µm, at least 50 µm, at least 75 µm, at least 100 µm, at least 200 µm, at least 300 µm, at least 400 µm, at least 500 µm, or at least 1000 µm. In some embodiments, a dimension of the fluid channel may be at most 1000 µm, at most 500 µm, at most 400 µm, at most 300 µm, at most 200 µm, at most 100 µm, at most 50 µm, at most 25 µm, at most 10 µm, or at most 5 µm. Any of the lower and upper values described in this paragraph may be combined to form a range included within the present disclosure, for example, in some embodiments a dimension of the fluid channel may range from about 75 µm to about 300 µm. Those of skill in the art will recognize that the dimension may have any value within this range, e.g., about 95 µm. In some embodiments, a depth of the fluid channel may be equal to that for the inlet and/or outlet ports of the device, Imaging techniques: In some embodiments of the disclosed methods and devices, the imaging of an analyte separation step and/or mobilization step may be performed using an optical detection technique, such as ultraviolet (UV) light absorbance, visible light absorbance, fluorescence, Fourier transform infrared spectroscopy, Fourier transform near infrared spectroscopy, Raman spectroscopy, optical spectroscopy, and the like. In some embodiments, all or a portion of a separation (or enrichment) channel, a junction or connecting channel that connects an end of the separation channel and a downstream analytical instrument or an electrospray orifice or tip, the electrospray orifice or tip itself, or any combination thereof may be imaged. In some embodiments the separation (or enrichment) channel may be the lumen of a capillary. In some embodiments, the separation (or enrichment) channel may be a fluid channel within a microfluidic device.

The wavelength range(s) used for detection of separated analyte bands will typically depend on the choice of imaging technique and the material(s) out of which the device or portion thereof are fabricated. For example, in the case that UV light absorbance is used for imaging all or a portion of the separation channel or other part of the microfluidic device, detection at about 220 nm (due to a native absorbance of peptide bonds) and/or at about 280 nm (due to a native absorbance of aromatic amino acid residues) may allow one to visualize protein bands during separation and/or mobilization provided that at least a portion of the device, e.g., the separation channel, is transparent to light at these wavelengths. In some embodiments, the analytes to be separated and characterized via ESI-MS may be labeled prior to separation with, e.g., a fluorophore, chemiluminescent tag, or other suitable label, such that they may be imaged using fluorescence imaging or other suitable imaging techniques. In some embodiments, e.g., wherein the analytes comprise proteins produced by a commercial manufacturing process, the proteins may be genetically-engineered to incorporate a green fluorescence protein (GFP) domain or variant thereof, so that they may be imaged using fluorescence. In some embodiments, proteins may be tagged or labeled. The labeled proteins may be configured such that the label does not interfere with or perturb the analyte property on which the chosen separation technique is based.

Any of a variety of imaging system components may be utilized for the purpose of implementing the disclosed methods, devices, and systems. Examples include, but are not limited to, one or more light sources (e.g., light emitting diodes (LEDs), diode lasers, fiber lasers, gas lasers, halogen lamps, arc lamps, etc.), condenser lenses, objective lenses, mirrors, filters, beam splitters, prisms, image sensors (e.g., CCD image sensors or cameras, CMOS image sensors or cameras, Diode Arrays, thermal imaging sensors, FTIR, etc.), and the like, or any combination thereof. Depending on the imaging mode utilized, the light source and image sensor may be positioned on opposite sides of the microfluidic device, e.g., so that absorbance-based images may be acquired. In some embodiments, the light source and image sensor may be positioned on the same side of the microfluidic device, e.g., so that epifluorescence images may be acquired.

Images may be acquired continuously during the separation, mobilization, and/or electrospray steps, or may be acquired at random or specified time intervals. In some embodiments, a series of one or more images are acquired continuously, at random time intervals, or at specified time intervals. In some embodiments, the series of one or more images may comprise video images.

Imaging of pI markers for determination of protein isoelectric points prior to electrospray: In some embodiments, as noted above, the positions of two or more pI markers in images of a separation channel comprising a separated analyte mixture that has been subjected to CIEF may be used to determine an isoelectric point for one or more individual analyte peaks (e.g., protein analyte peaks). In some embodiments, the isoelectric point for one or more analyte peaks is calculated from the positions of two or more pI markers on the basis of an assumed linear relationship between local pH and position along the separation channel. In some embodiments, the isoelectric point for one or more analyte peaks is calculated from the positions of three or more pI markers on the basis of a nonlinear fitting function (e.g., a nonlinear polynomial) that describes the relationship between local pH and position along the separation channel. In some embodiments, the isolelectric point for one or more analytes is calculated on the basis of the positions of 2, 3, 4, 5, 6, 7, 8, 9, or 10 or more pI standards that are determined from images of the separation channel.

In some embodiments, the images used for determining the positions of the two or more pI markers are acquired as the analyte mixture is being separated, and the calculation of pI for each analyte band is iteratively updated as the separation continues. In some embodiments, the images used for determining the positions of the two or more pI markers are acquired after separation is complete and prior to initiation of a mobilization step. In some embodiments, the images used for determining the positions of the two or more pI markers are acquired as the separated mixture is mobilized and expelled through an electrospray tip or orifice. In some embodiments, the images used for determining the positions of the two or more pI markers are acquired as the separated mixture is mobilized and expelled through a fluid channel that connects the separation channel to a downstream analytical instrument.

In some embodiments, the images used to determine the positions of two or more pI markers and of analyte band(s) in a separated mixture are acquired using a computer-implemented method (e.g., a software package). In some embodiments, the positions of the two or more pI markers as well as of the analyte band(s) are determined using a computer-implemented method that comprises automated image processing. In some embodiments, the computer-implemented method further comprises performing a calculation of isoelectric point for one or more analyte bands based on the position data derived from the automated image processing.

Figure 2:
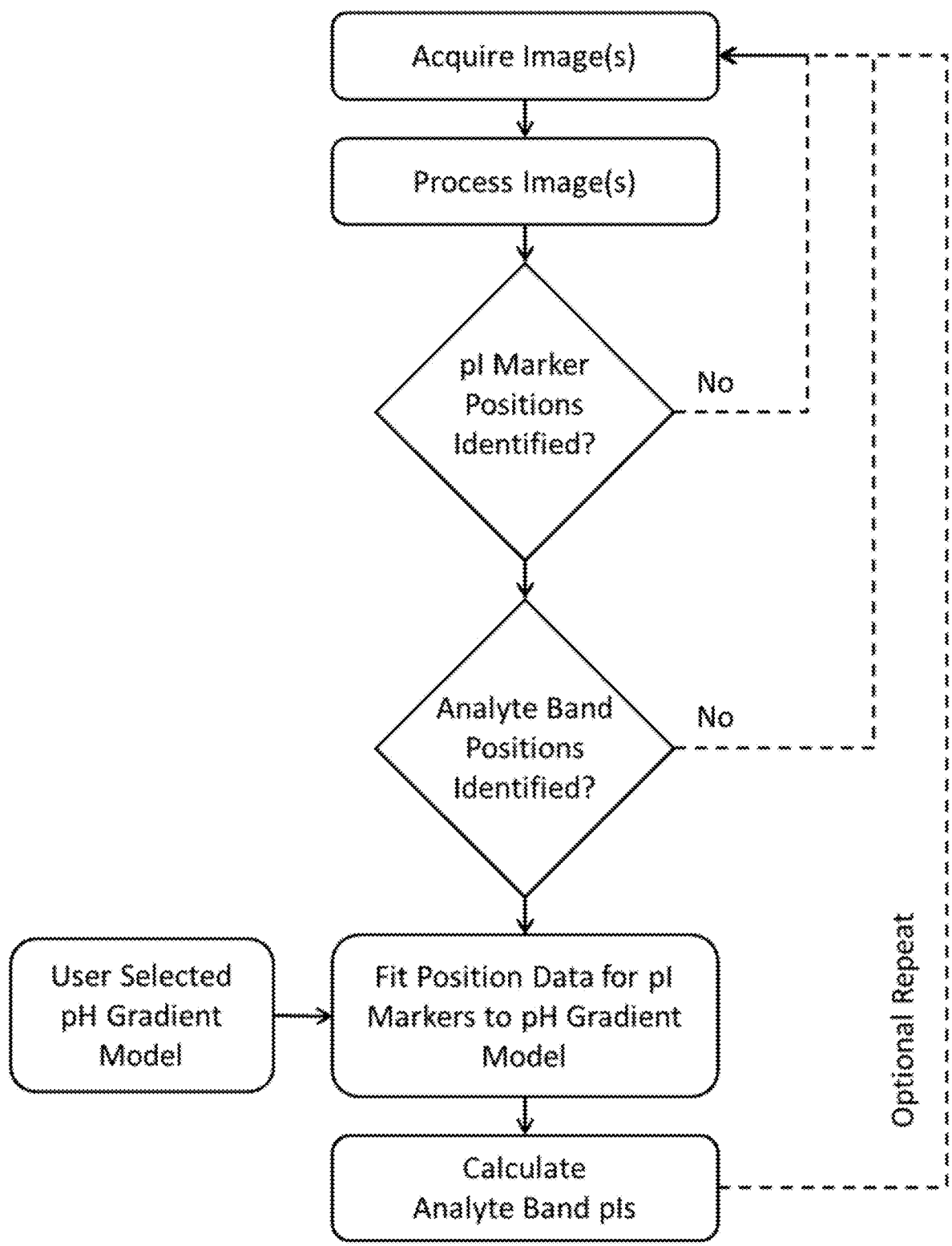
FIG. 2 provides an example flowchart of a computer-implemented method for calculating isoelectric points for separated analyte bands.

FIG. 2 provides an example process flow chart for a computer-implemented method to acquire image(s) of a separation channel (or other portion of a microfluidic device), determine the positions of pI markers and analyte bands in the image(s) (i.e., in the case where the separation step comprises CIEF), and calculate a pI for one or more analyte bands in the separated mixture of analytes. In some embodiments, the computer-implemented method may comprise controlling the acquisition of a series of one or more images which are then processed to identify the positions of pI markers and separated analyte bands. Examples of suitable automated image processing algorithms will be discussed in more detail below. In some embodiments, predetermined knowledge for the predicted position of the pI markers, e.g., the positions of pI markers as determined from images of a "control" sample comprising only the pI markers, may be used to discriminate between bands corresponding to pI markers and bands corresponding to separated analytes. In some embodiments, the images of pI markers may be acquired at a different wavelength or using a different imaging mode than that used to acquire the images of the separated analyte bands. As illustrated in FIG. 2, if the image processing step fails to determine the positions for the known number of pI markers and/or for the separated analyte bands, the system may be instructed to acquire new image(s) so that the image processing step may be repeated. Once the positions of the pI markers and separated analyte bands are determined, the data for the positions of the pI markers is fit to a user-selected model for the pH gradient (e.g., a linear or nonlinear model) and the resulting fitted relationship between local pH and position along the separation channel is then used to calculate the isoelectric point for one or more analyte bands.

In some embodiments, the computer-implemented method may be an iterative process, in which the steps of detection of pI marker and analyte band positions, fitting of the position data to a pH gradient model, and calculation of isoelectric points for one or more analyte bands is repeated so that the latter is continuously updated and refined (e.g., through averaging of several determinations). In some embodiments, a cycle comprising the steps of image acquisition and processing, detection of pI marker and analyte band positions, fitting of pI marker position data to a pH gradient model, and calculation of isoelectric points for one or more analyte bands may be completed in a sufficiently short time that the calculation of isoelectric points may be updated and refined at a rate of at least 0.01 Hz, 0.1 Hz, 0.2 Hz, 0.3 Hz, 0.4 Hz, 0.5 Hz, 0.6 Hz, 0.7 Hz, 0.8 Hz, 0.9 Hz, 1 Hz, 10 Hz, 100 Hz, or 1,000 Hz, or any other relevant rate, e.g., at a rate of at least the Nyquist rate.

Imaging of analyte bands to determine velocities: In some embodiments, as noted above, the position of one or more analyte bands may be determined from a series of two or more images of the separation channel (or other portion of a microfluidic device), such that a velocity for one or more analyte bands may be calculated from the difference in its relative position in the two or more images and the known time interval between the acquisition times for the two or more images. In some embodiments, the two or more images of at least a portion of the separation channel may be acquired while a separation step is being performed. In some embodiments, the two or more images may be acquired during a mobilization step. In some embodiments, the two or more images may be acquired while a separated sample is being expelled through a fluid channel that connects an end of the separation channel to a downstream analytical instrument. In some embodiments, the two or more images may be acquired while a separated sample is being expelled through an electrospray tip or orifice to form a Taylor cone. In some embodiments, the velocity determined for one or more analyte bands may be used to calculate the time at which a given analyte band exits the separation channel. In some embodiments, e.g., when there is one or more interconnecting fluid junctions or fluid channels that connect an end of the separation channel with an outlet port, e.g., an electrospray orifice or tip, the velocity determined for the one or more analyte bands may be used to calculate the time at which a given analyte band reaches the outlet port and exits the device. In some embodiments, the velocity determined for the one or more analyte bands may be used to calculate the time at which a given analyte band exits an electrospray tip or electrospray orifice and enters a Taylor cone formed between the electrospray tip or orifice and the inlet of a mass spectrometer.

In some embodiments, the sequence of images used to determine a velocity for one or more analyte bands may be acquired using a computer-implemented method (e.g., a software package). In some embodiments, the velocities of one or more analyte bands are determined using a computer-implemented method that comprises automated image processing. In some embodiments, the computer-implemented method further comprises performing a calculation of the time at which a given analyte band will exit the separation channel. In some embodiments, the computer-implemented method further comprises performing a calculation of the time at which a given analyte band will reach an outlet port and exit the device. In some embodiments, the computer-implemented method further comprises performing a calculation of the time at which a given analyte band will exit an electrospray tip or electrospray orifice and enter a Taylor cone formed between an electrospray tip or orifice and the inlet of a mass spectrometer. In some embodiments the exit time(s) determined for one or more analyte bands are used to correlate specific analyte bands with mass spectrometry data or data collected using other analytical instruments.

Figure 3:
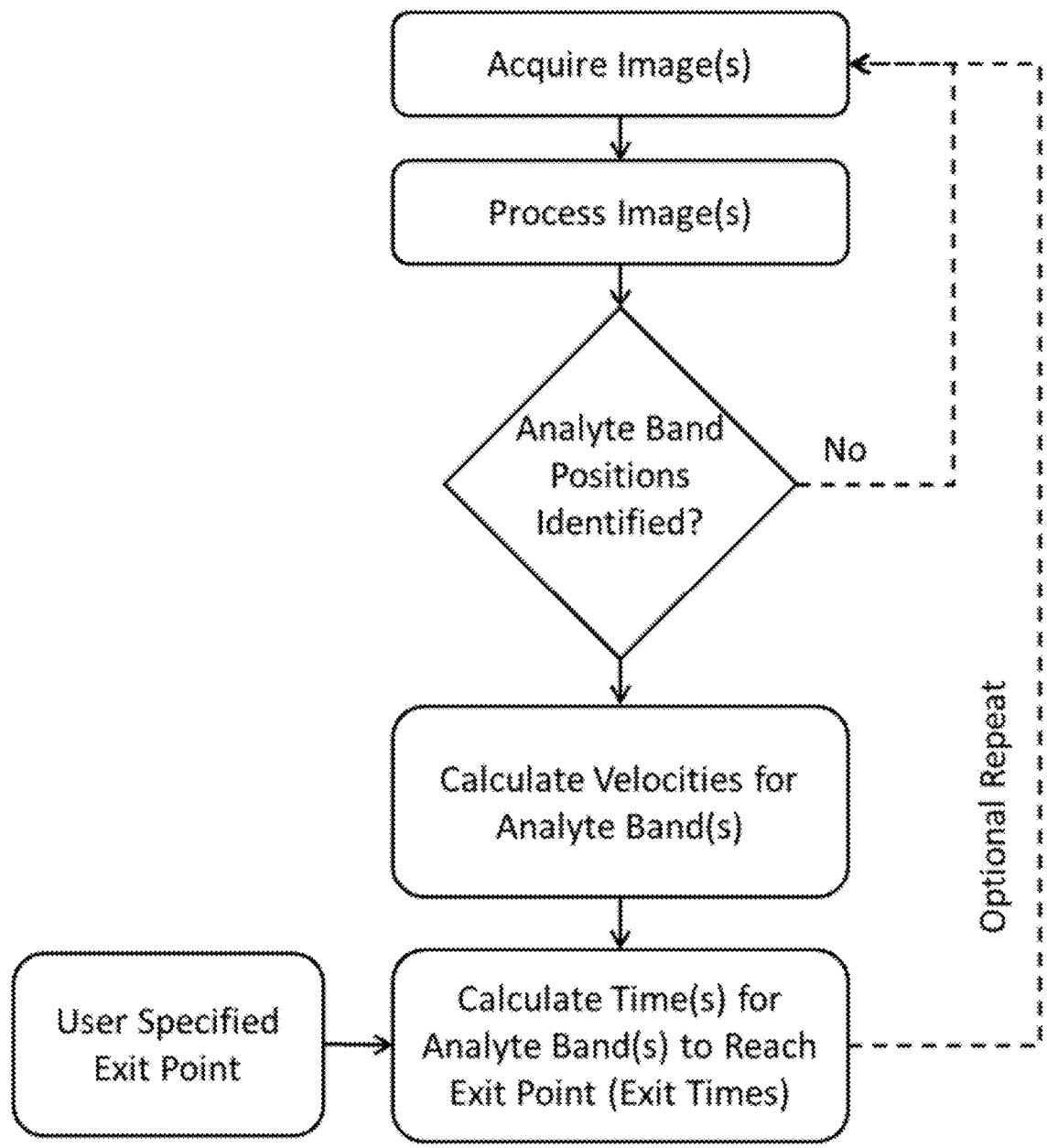
FIG. 3 provides another example flowchart for a computer-implemented method for determining a velocity for one or more separated analyte bands and calculating an exit time.

FIG. 3 provides another example process flow chart for a computer-implemented method to acquire image(s) of a separation channel (or other portion of a microfluidic device), determine the velocity of one or more analyte bands, and calculate at time at which a given analyte band will reach a specified point in the device, e.g., the end of the separation channel, a junction point between the separation channel and a secondary fluid channel, an outlet port of the device, or the outlet of an electrospray tip or orifice. In some embodiments, the computer-implemented method may comprise controlling the acquisition of a series of one or more images which are then processed to identify the positions of separated analyte bands. Examples of suitable automated image processing algorithms will be discussed in more detail below. As illustrated in FIG. 3, if the image processing step fails to determine the positions for the separated analyte bands, the system may be instructed to acquire new image(s) so that the image processing step may be repeated. Once the positions of the separated analyte bands are determined for a series of two or more images, a velocity is calculated for one or more of the analyte peaks based on their relative positions in the two or more images and the known time interval(s) between the acquisition times of the two or more images. In some embodiments, the tracking of one or more analyte bands from one image to the next in a series of images may be used to distinguish between several separated analyte bands, and to refine the velocity calculation (e.g., through averaging the velocity values calculated from several pairs of images in the series). In some embodiments, pI markers or other internal standards that may be detected using the selected imaging mode may be used as "velocity standards". The analyte band velocities thus determined may be used to calculate the time at which a given band will reach a user-specified point in the device, e.g., the outlet end of the separation channel, a particular fluid junction within the device, an outlet port of the device, an electrospray ionization tip or orifice where the analyte enters a Taylor cone, and the like.

In some embodiments, the computer-implemented method may be an iterative process, in which the steps of detection of analyte band positions, determination of analyte band velocities, and calculation of exit times is repeated so that the exit time prediction is continuously updated and the correlation of chemical separation data with mass spectrometry data (or other types of downstream analytical data) is further improved. In some embodiments, a cycle comprising the steps of image acquisition and processing, velocity calculation, and exit time prediction(s) may be completed in a sufficiently short time that the exit time prediction(s) may be updated at a rate of at least 0.01 Hz, 0.1 Hz, 0.2 Hz, 0.3 Hz, 0.4 Hz, 0.5 Hz, 0.6 Hz, 0.7 Hz, 0.8 Hz, 0.9 Hz, 1 Hz, 10 Hz, 100 Hz, or 1,000 Hz, or any other relevant rate, e.g., at a rate of at least the Nyquist rate.

Correlation of separation data with mass spectrometry data: In some embodiments, the computer-implemented methods described above for performing imaging-based determination of accurate isoelectric points for isoelectrically-focused analyte bands enables one to correlate isoelectric point data with specific m/z peaks in mass spectrometry data (or other analytical data), thereby improving the information content of the data set (even for single run experiments) and allowing more quantitative characterization of an analyte sample.

In some embodiments, the computer-implemented methods described above for using image-derived data to calculate velocities and predict exit times for separated analyte bands (using any of a variety of different separation techniques) enables one to improve the time correlation between chemical separation data (e.g., retention times, electrophoretic mobilities, isoelectric points, etc.) and specific m/z peaks in mass spectrometry data (or other analytical data), thereby improving both the information content of the data set (even for single run experiments) and allowing more quantitative comparisons of data collected for different sample runs, different samples, or data collected on different instruments due to the ability to correct for experiment-to-experiment or instrument-to-instrument variations in separation times. The disclosed methods, devices, and systems may thus be particularly advantageous for a variety of metabolomics, proteomics, and drug development or manufacturing applications.

In some embodiments (e.g., those comprising a CIEF step), the computer-implemented methods of the present disclosure may perform both imaging-based determination of precise isoelectric points and imaging-based determination of the velocities of the separated analyte bands.

Mass spectrometry and electrospray ionization: In some embodiments, the methods, devices, and systems of the present disclosure may be configured for performing electrospray ionization of a separated analyte mixture and its injection into a mass spectrometer. Mass spectrometry (MS) is an analytical technique that measures the "mass" of analyte molecules in a sample by ionizing them and sorting the resultant ions based on their mass-to-charge (m/z) ratio. Combined with an upfront liquid- or gas-phase sample separation system, mass spectrometry provides one of the most effective means available for analyzing complex samples comprising a plurality of low abundance analytes, as is common, for example, in biological samples.

All mass spectrometers share the requirement that the ions be in the gas phase prior to introduction into a mass analyzer. A variety of sample ionization modes have been developed including, but not limited to, matrix-assisted laser desorption and ionization (MALDI) and electrospray ionization (ESI). In the MALDI technique, the sample (e.g., a biological sample comprising a mixture of proteins) is mixed with an energy absorbing matrix (EAM) such as sinapinic acid or α-cyano-4-hydroxycinnamic acid and crystallized onto a metal plate. Surface enhanced laser desorption and ionization (SELDI) is a common variant of the technique that incorporates additional surface chemistry on the metal plate to promote specific binding of certain classes of proteins. The plate is inserted into a vacuum chamber, and the matrix crystals are struck with light pulses from a nitrogen laser. The energy absorbed by the matrix molecules is transferred to the proteins, causing them to desorb, ionize, and produce a plume of ions in the gas phase that are accelerated in the presence of an electric field and drawn into a flight tube where they drift until they strike a detector that records the time of flight. The time of flight may in turn be used to calculate the m/z ratio for the ionized species. In some embodiments of the disclosed devices, an outlet port of the device may comprise a capillary or other feature used to deposit separated analyte bands (or fractions thereof) onto a MALDI plate in preparation for mass spectrometric analysis, e.g., to correlate isoelectric points for specific analyte bands with MALDI mass spectrometer data.

Electrospray ionization (ESI; also referred to herein simply as "electrospray") is another widely used technique due to its inherent compatibility for interfacing liquid chromatographic or electrokinetic chromatographic separation techniques with a mass spectrometer. As noted above, in electrospray ionization, small droplets of sample and solution are emitted from a distal end of a capillary or microfluidic device comprising an electrospray feature (e.g., an emitter tip or orifice) by the application of an electric field between the tip or orifice and the mass spectrometer source plate. The droplet then stretches and expands in this induced electric field to form a cone shaped emission (i.e., a "Taylor cone"), which comprises increasingly small droplets that evaporate and produce the gas phase ions that are introduced into the mass spectrometer for further separation and detection. Emitter tips may be formed from a capillary or a corner or ESI tip built into microfluidic chip design, which provides a convenient droplet volume for ESI. Emitter tips may be sharpened to provide a small surface and drop volume using a lapping wheel, file, machining tools, CNC machining tools, water jet cutting, or other tools or process to shape the ESI tip to provide a small surface volume, and the like. In some embodiments, the tip may be drawn by heating and stretching the tip portion of the chip. In some embodiments, the tip may then be cut to a desired length or diameter. In some embodiments, the electrospray tip may be coated with a hydrophobic coating which may minimize the size of droplets formed on the tip. In some embodiments, the system may electrospray mobilizer, catholyte, or any other liquid during a separation step, when no analyte is being eluted from the device.

In some embodiments of the disclosed methods, devices, and systems, other ionization methods are used, such as inductive coupled laser ionization, fast atom bombardment, soft laser desorption, atmospheric pressure chemical ionization, secondary ion mass spectrometry, spark ionization, thermal ionization, and the like.

With respect to electrospray ionization, in some embodiments the disclosed microfluidic devices comprise features designed to promote efficient electrospray ionization and convenient interfacing with downstream mass spectrometric analysis, as illustrated in FIG. 1. The mass-to-charge ratio (or "mass") for analytes expelled from the microfluidic device (e.g., a biologic or biosimilar) and introduced into a mass spectrometer can be measured using any of a variety of different mass spectrometer designs. Examples include, but are not limited to, time-of-flight mass spectrometry, quadrupole mass spectrometry, ion trap or orbitrap mass spectrometry, distance-of-flight mass spectrometry, Fourier transform ion cyclotron resonance, resonance mass measurement, and nanomechanical mass spectrometry.

In some embodiments, the electrospray feature of a microfluidic device may be in-line with a separation channel. In some embodiments, the electrospray feature of a microfluidic device may be oriented at a right angle or at an intermediate angle relative to a separation channel. In some embodiments of the disclosed methods, substantially all of the separated and/or enriched analyte fractions from a final separation or enrichment step performed in a capillary or microfluidic device are expelled from the electrospray tip or feature in a continuous stream. In some embodiments, a portion of the analyte mixture (e.g., a fraction of interest) may be expelled from a microfluidic device via an outlet configured to interface with an analytical instrument, such as a mass spectrometer or another device configured to fractionate and/or enrich at least a portion of the sample. Another portion of the analyte mixture (e.g., containing fractions other than the fraction of interest) can be expelled via a waste channel.

In some embodiments, the expulsion from the capillary or microfluidic device is performed using pressure, electric force, ionization, or any combination of these. In some embodiments, the expulsion coincides with a mobilization step as described above. In some embodiments a sheath liquid used for electrospray ionization is used as an electrolyte for an electrophoretic separation. In some embodiments, a nebulizing gas is provided to reduce the analyte fraction to a fine spray.

Imaging-based feedback of electrospray ionization performance: Conventional ESI-MS systems using capillaries or microfluidic devices generally provide no tools for calibrating the system to reestablish a Taylor cone during operation. Maintaining a stable Taylor cone can be complicated by the electrophoresis electric field applied across the separation channel in the microfluidic device or capillary. Changes in the conductivity of reagents between runs, or during a run, can change the voltage potential at the interface with the mass spectrometer. Changes in potential at the interface may adversely affect the Taylor cone and can lead to loss of electrospray ionization efficiency. Disclosed herein are methods and systems for improving the electrospray ionization performance and thus the quality of mass spectrometry data collected for capillary-based or microfluidic device-based ESI-MS systems. In some embodiments, for example, imaging of the Taylor cone in an electrospray ionization setup may be used in a computer implemented method to provide feedback control of one or more operating parameters such that the shape, density, or other characteristic of the Taylor cone is maintained within a specified range. In some embodiments, the operating parameters that may be controlled through such a feedback process include, but are not limited to, the alignment of the electrospray tip or orifice with the mass spectrometer inlet, the distance between the electrospray tip and the mass spectrometer inlet (e.g., by mounting the capillary tip or microfluidic device comprising an integrated electrospray feature on a programmable precision X-Y-Z translation stage), the flow rate of analyte sample through the electrospray tip (e.g., by adjusting the pressure, electric field strength, or combination thereof that are used to drive the expulsion of analyte sample), the voltage applied, e.g., at a proximal end of the channel, e.g., between the electrospray tip or orifice and the mass spectrometer inlet, the volumetric flowrate of a sheath liquid or sheath gas surrounding the expulsed analyte sample, or any combination thereof.

Figure 4:
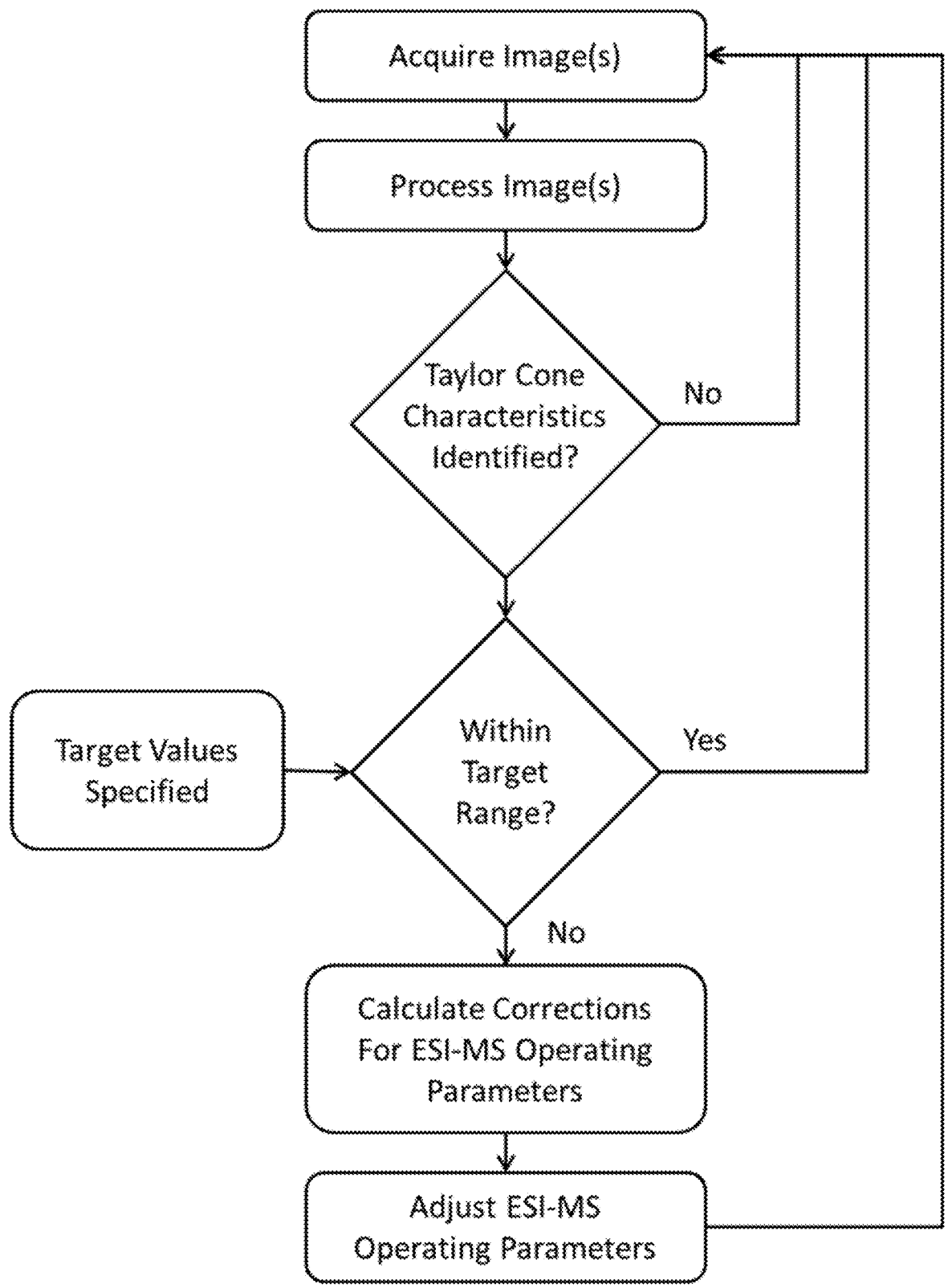
FIG. 4 provides another example flowchart for a computer-implemented method for implementing imaging-based feedback and control of one or more operating parameters for an ESI-MS analysis system.

FIG. 4 provides an example process flow chart for a computer-implemented method used to: (i) acquire images of the Taylor cone (using any of a variety of image sensors, e.g., CCD image sensors or CMOS image sensors), (ii) process the images to determine a shape, density, or other characteristic of the Taylor cone, (iii) compare the shape, density, or other characteristic of the Taylor cone with a set of specified or target values, and (iv) based on said comparison, use a mathematical algorithm that relates the shape, density, or other characteristic of the Taylor cone to one or more operating parameters to determine an appropriate adjustment to the one or more operating parameters to restore the Taylor cone to the specified or target values. In some embodiments, data acquired from the mass spectrometer (e.g., total ion current data) may be used in addition to data derived from images of the Taylor cone to monitor system performance and make adjustments to one or more operational parameters.

In some embodiments, the cyclical process illustrated in FIG. 4, comprising the steps of image acquisition and processing, identification of Taylor cone characteristics, comparison of the said Taylor cone characteristics with a set of target values, and calculation of the adjustments needed to one or more ESI-MS systems operating parameters, may be completed in a sufficiently short time that the one or more operating parameters may be updated at a rate of at least 0.01 Hz, 0.1 Hz, 0.2 Hz, 0.3 Hz, 0.4 Hz, 0.5 Hz, 0.6 Hz, 0.7 Hz, 0.8 Hz, 0.9 Hz, 1 Hz, 10 Hz, 100 Hz, or 1,000 Hz, or any other relevant rate, e.g., at a rate of at least the Nyquist rate.

Alternating high mass/low mass scanning: In some embodiments of the disclosed methods, devices, and systems, the mass spectrometer may be set to alternate between a high mass scan range (e.g., an m/z range of about 1500-6000), or "high mass scan", and a low mass scan range (e.g., an m/z range of about 150-1500), or "low mass scan", such that the low mass scan may be used to identify low mass markers, e.g., free solution ampholytes in the instance that an isoelectric focusing separation step was performed, that can be identified in the mass spectrometry data and used to calibrate it with respect to a property indicated by the low mass marker (e.g., a specific range of isoelectric point in the case that free solution ampholytes are detected, peptides, small molecule markers). The switching between high mass scans and low mass scans and the scan rates should be fast relative to the efflux of analyte sample from the electrospray interface. In some instances, the switching rate between high mass scans and low mass scans may range from about 0.5 Hz to about 50 Hz. In some instances, the switching rate may be at least 0.5 Hz, at least 1 Hz, at least 5 Hz, at least 10 Hz, at least 20 Hz, at least 30 Hz, at least 40 Hz, or at least 50 Hz.

Altering high and low separation/mobilization voltage to keep ESI tip voltage constant: In some embodiments, the ESI ion source on the mass spectrometer will have an adjustable power supply capable of setting a negative voltage on the mass spectrometer. In some embodiments, the ESI ion source on the mass spectrometer will have an adjustable power supply capable of setting a positive voltage on the mass spectrometer. In some embodiments, the ESI ion source on the mass spectrometer will be held at ground. In some embodiments, the ESI tip on the capillary or microfluidic device will be held at or close to ground to generate an electric field between the ESI tip and the charged ESI ion source on the mass spectrometer. In some embodiments, the ESI tip on the capillary or microfluidic device will be held at a positive or negative voltage to generate an electric field between the ESI tip and the grounded ESI ion source on the mass spectrometer.

Figure 15:
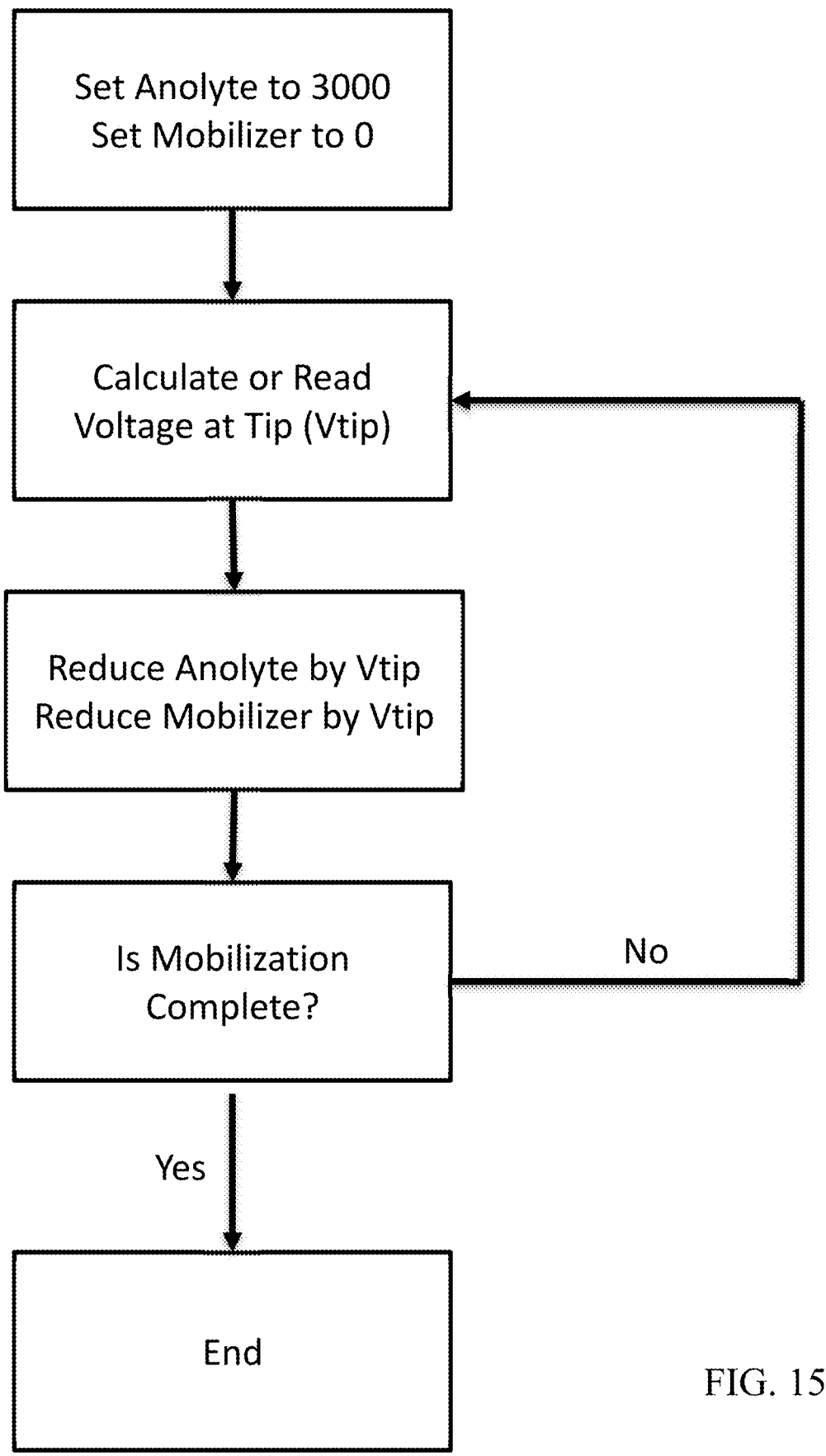
FIG. 15 provides an exemplary flowchart of a computer-controlled voltage feedback loop where the ESI tip is held at 0V.

FIG. 15 provides an exemplary flowchart of a computer-controlled feedback loop to maintain a constant voltage drop of 3000V between the anode and cathode while keeping the ESI tip voltage at 0V during mobilization. In some embodiments, this feedback loop may be implemented when the mass spectrometer ESI ion source is set at a positive or negative voltage relative to ground (for example, −3500V). In this example, ΔV between anolyte port 110 and mobilizer port 104 is kept at 3000V by initially setting anolyte port 110 at +3000V and mobilizer port 104 at 0V in FIG. 7A. In some embodiments, a different ΔV may be set by setting anolyte port 110 to a different value. In some embodiments, anodic mobilization may be used, and port 110 would be a catholyte port, set to, for example, −3000V. In the example outlined in FIG. 15, during mobilization, the resistance in separation channel 112 is dropping due to analyte and ampholytes in the separation regaining charge. This causes the voltage drop across channel 112 to drop, leading to an increase in voltage at ESI tip 116, according to equation 1:

$$V_{116} = (\Delta V_{110\text{-}104}) \ast (R_{105})/(R_{109}+R_{112}+R_{105})$$

However, by measuring or calculating ESI tip voltage 116, the voltage settings at anolyte port 110 and mobilizer port 104 can be adjusted. By subtracting ESI tip voltage 116 from both anolyte port 110 and mobilizer port 104 settings, $\Delta V_{110\text{-}104}$ remains 3000V so the mobilization is unaffected, but ESI tip 116 voltage is set to 0 according to equation 2:

$$V_{116} = (\Delta V_{110\text{-}104}) \ast (R_{105})/(R_{109}+R_{112}+R_{105}) + V_{104}$$

This feedback loop continues to operate until the mobilization is complete, adjusting ESI tip 116 voltage to 0 at a regular frequency, e.g., the Nyquist rate, or about 0.2 Hz. In some instances, the voltage at ESI tip 116 may be adjusted to 0 at a rate of at least 0.01 Hz, 0.1 Hz, 0.2 Hz, 0.3 Hz, 0.4 Hz, 0.5 Hz, 0.6 Hz, 0.7 Hz, 0.8 Hz, 0.9 Hz, 1 Hz, 10 Hz, 100 Hz, or 1,000 Hz. Maintaining a constant stable voltage at ESI tip 116 can be critical to maintaining stable electrospray during the mobilization process.

In some instances, the feedback loop operates to maintain the voltage at the ESI tip to within a specified percentage of a pre-set value. For example, in some instances, the feedback loop operates to maintain the voltage at the ESI tip to within 10%, 9%, 8%, 7%, 6%, 5%, 4%, 3%, 2%, 1%, 0.5%, or 0.1% of a pre-set value. In some instances, the feedback loop operates to maintain the ESI tip voltage to within 1000V, 500V, 100V, 75V, 50V, 25V, 10V, 5V, or 1V of a pre-set value.

Figure 12:
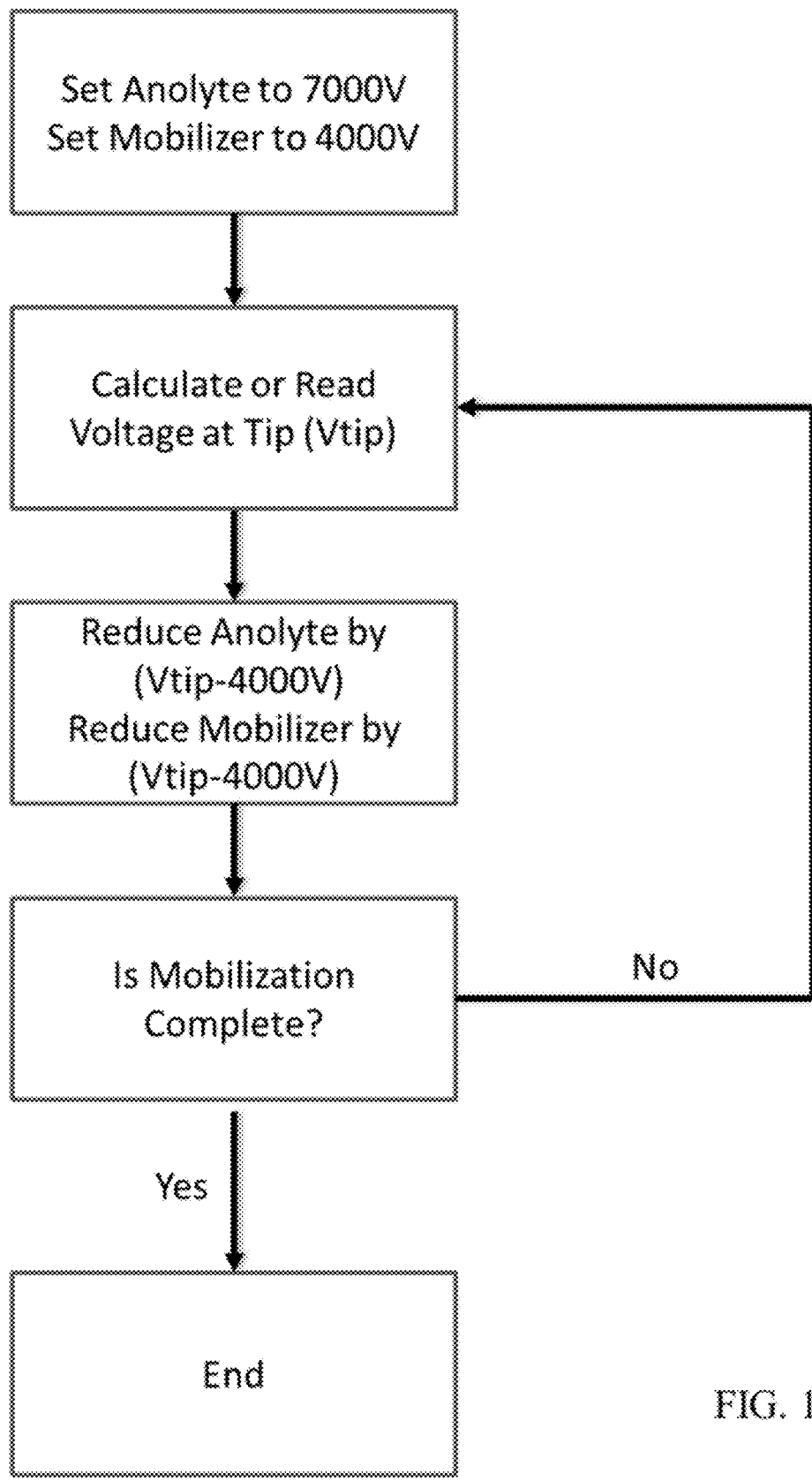
FIG. 12 provides an example flowchart of voltage feedback loop where the ESI tip is held at +3000V.

In some embodiments, the mass spectrometer ESI ion source is held at ground, and ESI tip 116 will need to be kept at a constant positive or negative voltage in order to create an electric field between ESI tip 116 and the mass spectrometer. In some embodiments, ESI tip voltage (e.g., the pre-set value) may be around +5000V, around +4000V, around +3500V, around +3000V, around +2500V, around +2000V, around +1500V around +1000V, around +500V, or around −5000V, around −4000V, around −3500V, around −3000V, around −2500V, around −2000V, around −1500V, around −1000V, or around −500V. FIG. 12 provides an example flowchart of a computer-controlled feedback loop to maintain a constant voltage drop of 3000V between the anode and cathode while keeping the ESI tip voltage at 3000V during mobilization. Operation of the computer-controlled feedback loop is the same as in FIG. 15, except voltages at anolyte port 110 and mobilizer port 104 are offset by +3000V, which offsets the voltage at ESI tip 116 to +3000V, still obeying equation 2. In some embodiments control of the electric field strength can be accomplished using analog circuitry. In some embodiments, the control of voltages at one or more electrodes in contact with the capillary-based or microfluidic device-based separation system may be provided by using one, two, three, or four or more independent high-voltage power supplies. In some instance, the control of voltages at one or more electrodes in contact with the capillary-based or microfluidic device-based separation system may be provided, e.g., by using a single, multiplexed high-voltage power supply.

In some instances, the feedback loop operates to maintain the electric field strength within the separation channel, or the voltage drop between the anode and cathode, to within a specified percentage of a pre-set value. For example, in some instances, the feedback loop operates to maintain the electric field strength within the separation channel, or the voltage drop between the anode and cathode, to within 10%, 9%, 8%, 7%, 6%, 5%, 4%, 3%, 2%, 1%, 0.5%, 0.1%, or 0.01% of a pre-set value. In some instances, the feedback loop operates to maintain the electric field strength within the separation channel, or the voltage drop between the anode and cathode, to within 1000V, 500V, 100V, 75V, 50V, 25V, 10V, 5V, or 1V of a pre-set value.

Figure 5:
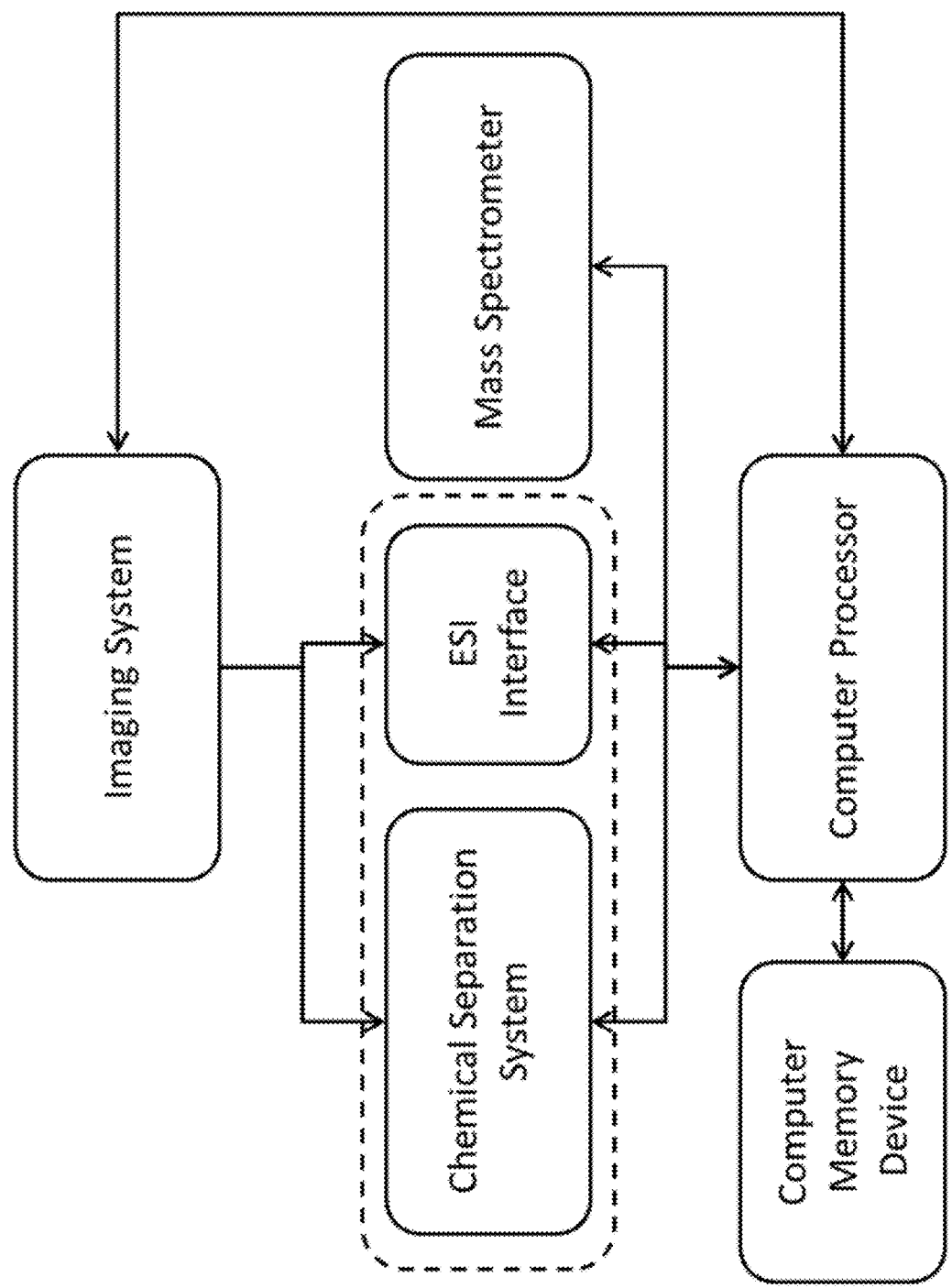
FIG. 5 provides a schematic block diagram of the hardware components for one embodiment of the disclosed systems.

System hardware: FIG. 5 provides a schematic illustration of a system hardware block diagram for one embodiment of the disclosed methods, devices, and systems. As illustrated, a system of the present disclosure may comprise one or more of the following hardware components: (i) a chemical separation system (e.g., a capillary or microfluidic device designed to perform an analyte separation, e.g., an isoelectric focusing-based separation, and one or more high-voltage power supplies), (ii) an electrospray interface for a mass spectrometer that, in some cases, may be directly integrated with the separation system (as indicated by the dashed line), (iii) a mass spectrometer, (iv) an imaging device or system, (v) a processor or computer, and (vi) a computer memory device, or any combination thereof. In some embodiments, the system may further comprise one or more capillary or microfluidic device flow controllers (e.g., programmable syringe pumps, peristaltic pumps, HPLC pumps, etc.), temperature controllers configured to maintain a specified temperature for all or a portion of a capillary or microfluidic device, additional photo sensors or image sensors (e.g., photodiodes, avalanche photodiodes, CMOS image sensors and cameras, CCD image sensors and cameras, etc.), light sources (e.g., light emitting diodes (LEDs), diode lasers, fiber lasers, gas lasers, halogen lamps, arc lamps, etc.), other types of sensors (e.g., temperature sensors, flow sensors, pH sensors, conductivity sensors, etc.), computer memory devices, computer display devices (e.g., comprising a graphical user interface), digital communication devices (e.g., intranet, internet, WiFi, Bluetooth®, or other hard-wired or wireless communication hardware), and the like.

In some embodiments, the system may comprise an integrated system in which a selection of functional hardware components are packaged in a fixed configuration. In some embodiments, the system may comprise a modular system in which the selection of functional hardware components may be changed in order to reconfigure the system for new applications. In some embodiments, some of these functional system components, e.g., capillaries or microfluidic devices, are replaceable or disposable components.

As noted above, any of a variety of different mass spectrometers may be utilized in different embodiments of the disclosed systems including, but not limited to, time-of-flight mass spectrometers, quadrupole mass spectrometers, ion trap or orbitrap mass spectrometers, distance-of-flight mass spectrometers, Fourier transform ion cyclotron resonance spectrometers, resonance mass measurement spectrometers, and nanomechanical mass spectrometers.

Figure 6:
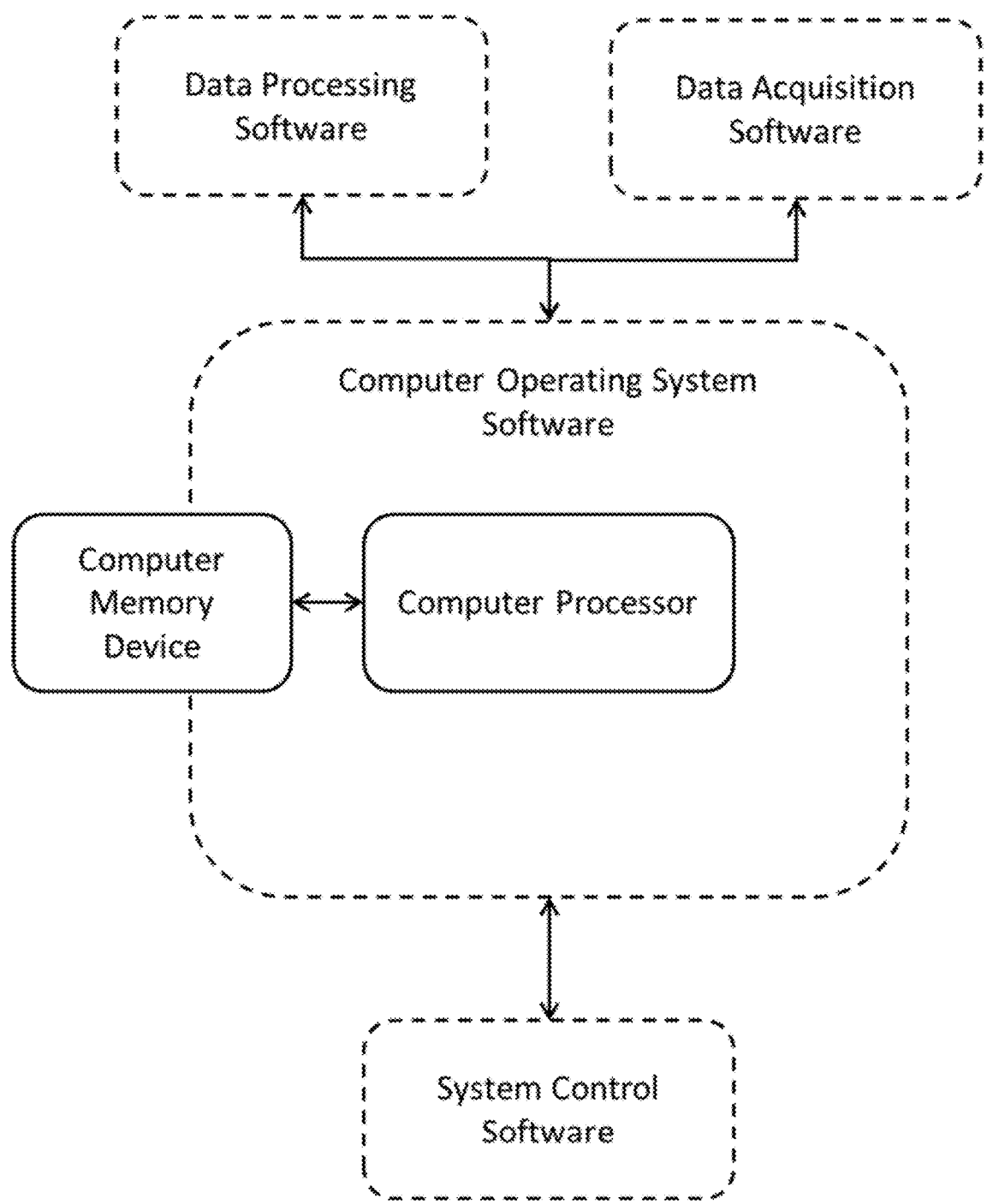
FIG. 6 provides a schematic block diagram of the software components for one embodiment of the disclosed systems.

System & application software: As illustrated in FIG. 6, a system of the present disclosure may comprise a plurality of software modules. For example, a system may comprise a system control software module, a data acquisition software module, a data processing software module, or any combination thereof. In general, these software modules will be configured to operate within an operating system or environment hosted by a computer processor, and may communicate and share data with each other and/or the operating system.

In some embodiments, a system control software module may comprise software for: (i) coordinating the operation of the capillary- or microfluidic device-based analyte separation system with image acquisition by an imaging system, (ii) coordinating the operation of capillary- or microfluidic device-based analyte separation system with data acquisition by the mass spectrometer system, (iii) coordinating image acquisition by an imaging system with operation of the capillary- or microfluidic device-based analyte separation system and/or mass spectrometer system, (iv) providing feedback control of one or more operating parameters of an electrospray ionization setup and/or mass spectrometer based on data derived from imaging of a separation channel and/or a Taylor cone, (v) controlling data acquisition by the mass spectrometer while switching between high mass and low mass scan ranges in an alternating fashion, (vi) monitoring voltage at ESI tip and adjusting separation circuit voltages to maintain a constant separation electric field strength (or voltage drop between the anode and cathode) and constant voltage at ESI tip, or any combination thereof.

In some embodiments, a data acquisition module may comprise software for: (i) controlling image acquisition by one or more image sensors or imaging systems, storing said image data, and providing a software interface with system control and/or data processing software modules, and (ii) controlling data acquisition by one or more mass spectrometer systems, storing said mass spectrometer data (or other downstream analytical instrument), and providing a software interface with system control and/or data processing software, or any combination thereof.

In some embodiments, a data processing module may comprise software for: (i) processing images and determining the position(s) of one or more pI standards or analyte peaks in a separation channel while the separation is being performed, after the separation is complete, or after mobilization of the pI standards and analyte peaks towards a separation channel outlet or electrospray tip, (ii) processing images and determining a velocity, an exit time, and/or an electrospray emission time for one or more pI standard or analyte peaks, (iii) processing of images of a separation channel to monitor a position of an analyte peak and images of a Taylor cone to monitor electrospray performance, where the images of the separation channel and Taylor cone are acquired either simultaneously or alternately, (iv) processing images of a Taylor cone, determining a shape, density, or other characteristic of the Taylor cone, and calculating an adjustment to be made to one or more operating parameters comprising the position (i.e., alignment and/or separation distance) of the electrospray tip or orifice relative to the mass spectrometer inlet, the fluid flow rate through the electrospray tip or orifice, the voltage between the electrospray tip or orifice and the mass spectrometer, etc., or any combination thereof, to affect a change in a quality of the mass spectrometer data; or any combination thereof.

The disclosed system and application software may be implemented using any of a variety or programming languages and environments known to those of skill in the art. Examples include, but are not limited to, C, C++, C#, PL/I, PL/S, PL/8, PL-6, SYMPL, Python, Java, LabView, Visual Basic, .NET and the like.

Image processing software: In some embodiments, as noted above, the data processing module may comprise image processing software for determining the positions of pI markers or separated analyte bands, for characterizing the shape, density, or other visual indicator of Taylor cone function, etc. Any of a variety of image processing algorithms known to those of skill in the art may be utilized for image pre-processing or image processing in implementing the disclosed methods and systems. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), and mathematical analysis algorithms (e.g., Fourier transform, fast Fourier transform, wavelet analysis, auto-correlation, Savitzky-Golay smoothing, Eigen analysis, etc.), or any combination thereof.

Processors and computer systems: One or more processors or computers may be employed to implement the methods disclosed herein. The one or more processors may comprise a hardware processor such as a central processing unit (CPU), a graphic processing unit (GPU), a general-purpose processing unit, or computing platform. The one or more processors may be comprised of any of a variety of suitable integrated circuits (e.g., application specific integrated circuits (ASICs) designed specifically for implementing deep learning network architectures, or field-programmable gate arrays (FPGAs) to accelerate compute time, etc., and/or to facilitate deployment), microprocessors, emerging next-generation microprocessor designs (e.g., memristor-based processors), logic devices and the like. Although the disclosure is described with reference to a processor, other types of integrated circuits and logic devices may also be applicable. The processor may have any suitable data operation capability. For example, the processor may perform 512 bit, 256 bit, 128 bit, 64 bit, 32 bit, or 16 bit data operations. The one or more processors may be single core or multi core processors, or a plurality of processors configured for parallel processing.

The one or more processors or computers used to implement the disclosed methods may be part of a larger computer system and/or may be operatively coupled to a computer network (a "network") with the aid of a communication interface to facilitate transmission of and sharing of data. The network may be a local area network, an intranet and/or extranet, an intranet and/or extranet that is in communication with the Internet, or the Internet. The network in some cases is a telecommunication and/or data network. The network may include one or more computer servers, which in some cases enables distributed computing, such as cloud computing. The network, in some cases with the aid of the computer system, may implement a peer-to-peer network, which may enable devices coupled to the computer system to behave as a client or a server.

The computer system may also include memory or memory locations (e.g., random-access memory, read-only memory, flash memory, Intel® Optane™ technology), electronic storage units (e.g., hard disks), communication interfaces (e.g., network adapters), for communicating with one or more other systems, and peripheral devices, such as cache, other memory, data storage and/or electronic display adapters. The memory, storage units, interfaces and peripheral devices may be in communication with the one or more processors, e.g., a CPU, through a communication bus, e.g., as is found on a motherboard. The storage unit(s) may be data storage unit(s) (or data repositories) for storing data.

The one or more processors, e.g., a CPU, execute a sequence of machine-readable instructions, which are embodied in a program (or software). The instructions are stored in a memory location. The instructions are directed to the CPU, which subsequently program or otherwise configure the CPU to implement the methods of the present disclosure. Examples of operations performed by the CPU include fetch, decode, execute, and write back. The CPU may be part of a circuit, such as an integrated circuit. One or more other components of the system may be included in the circuit. In some cases, the circuit is an application specific integrated circuit (ASIC).

The storage unit stores files, such as drivers, libraries and saved programs. The storage unit stores user data, e.g., user-specified preferences and user-specified programs. The computer system in some cases may include one or more additional data storage units that are external to the computer system, such as located on a remote server that is in communication with the computer system through an intranet or the Internet.

Some aspects of the methods and systems provided herein are implemented by way of machine (e.g., processor) executable code stored in an electronic storage location of the computer system, such as, for example, in the memory or electronic storage unit. The machine executable or machine readable code is provided in the form of software. During use, the code is executed by the one or more processors. In some cases, the code is retrieved from the storage unit and stored in the memory for ready access by the one or more processors. In some situations, the electronic storage unit is precluded, and machine-executable instructions are stored in memory. The code may be pre-compiled and configured for use with a machine having one or more processors adapted to execute the code, or may be compiled at run time. The code may be supplied in a programming language that is selected to enable the code to execute in a pre-compiled or as-compiled fashion.

Various aspects of the disclosed methods and devices may be thought of as "products" or "articles of manufacture", e.g., "computer program or software products", typically in the form of machine (or processor) executable code and/or associated data that is stored in a type of machine readable medium, where the executable code comprises a plurality of instructions for controlling a computer or computer system in performing one or more of the methods disclosed herein. Machine-executable code may be stored in an optical storage unit comprising an optically readable medium such as an optical disc, CD-ROM, DVD, or Blu-Ray disc. Machine-executable code may be stored in an electronic storage unit, such as memory (e.g., read-only memory, random-access memory, flash memory) or on a hard disk. "Storage" type media include any or all of the tangible memory of the computers, processors or the like, or associated modules thereof, such as various semiconductor memory chips, optical drives, tape drives, disk drives and the like, which may provide non-transitory storage at any time for the software that encodes the methods and algorithms disclosed herein.

All or a portion of the software code may at times be communicated via the Internet or various other telecommunication networks. Such communications, for example, enable loading of the software from one computer or processor into another, for example, from a management server or host computer into the computer platform of an application server. Thus, other types of media that are used to convey the software encoded instructions include optical, electrical and electromagnetic waves, such as those used across physical interfaces between local devices, through wired and optical landline networks, and over various atmospheric links. The physical elements that carry such waves, such as wired or wireless links, optical links, or the like, are also considered media that convey the software encoded instructions for performing the methods disclosed herein. As used herein, unless restricted to non-transitory, tangible "storage" media, terms such as computer or machine "readable medium" refer to any medium that participates in providing instructions to a processor for execution.

The computer system typically includes, or may be in communication with, an electronic display for providing, for example, images captured by a machine vision system. The display is typically also capable of providing a user interface (UI). Examples of UI's include but are not limited to graphical user interfaces (GUIs), web-based user interfaces, and the like.

Applications: As noted above, the disclosed methods, devices, systems, and software have potential application in a variety of fields including, but not limited to, proteomics research, drug discovery and development, and clinical diagnostics. For example, the improved information content and data quality that may be achieved for separation-based ESI-MS analysis of analyte samples using the disclosed methods may be of great benefit for the characterization of biologic and biosimilar pharmaceuticals during development and/or manufacturing. Other applications may include, but are not limited to, analysis of environmental pollutants, pesticides, small molecules, metabolites, peptides, post-translational modifications, glycoforms, antibody-drug conjugates, fusion proteins, viruses, allergans, single cell organisms, and other applications.

Biologics and biosimilars are a class of drugs which include, for example, recombinant proteins, antibodies, live virus vaccines, human plasma-derived proteins, cell-based medicines, naturally-sourced proteins, antibody-drug conjugates, protein-drug conjugates and other protein drugs. The FDA and other regulatory agencies require the use of a stepwise approach to demonstrating biosimilarity, which may include a comparison of the proposed product and a reference product with respect to structure, function, animal toxicity, human pharmacokinetics (PK) and pharmacodynamics (PD), clinical immunogenicity, and clinical safety and effectiveness (see "Scientific Considerations in Demonstrating Biosimilarity to a Reference Product: Guidance for Industry", U.S. Department of Health and Human Services, Food and Drug Administration, April 2015). Examples of the structural characterization data that may be required for protein products include primary structure (i.e., amino acid sequence), secondary structure (i.e., the degree of folding to form alpha helix or beta sheet structures), tertiary structure (i.e., the three dimensional shape of the protein produced by folding of the polypetide backbone and secondary structural domains), and quaternary structure (e.g., the number of subunits required to form an active protein complex, or the protein's aggregation state)). In many cases, this information may not be available without employing laborious, time-intensive, and costly techniques such as x-ray crystallography. Thus there is a need for experimental techniques that allow for convenient, real-time, and relatively high-throughput characterization of protein structure for the purposes of establishing biosimilarity between candidate biological drugs and reference drugs.

In some embodiments, the disclosed methods, devices, and systems may be used to provide structural comparison data for biological drug candidates (e.g., monoclonal antibodies (mAb)) and reference biological drugs for the purpose of establishing biosimilarity. For example, in some instances, isoelectric point data and/or mass spectrometry data for a drug candidate and a reference drug may provide important evidence in support of a demonstration of biosimilarity. In some embodiments, isoelectric point data and/or mass spectrometry data for a drug candidate and a reference drug that have both been treated with a site-specific protease under identical reaction conditions may provide important evidence in support of a demonstration of biosimilarity. In some embodiments, the disclosed methods, devices, and systems may be used to monitor a biologic drug manufacturing process to ensure the quality and consistency of the product by analyzing samples drawn at different points in the production process, or samples drawn from different production runs. In some embodiments, the disclosed methods, devices, and systems may be used to evaluate stability of formulation buffers. In some embodiments, the disclosed methods, devices, and systems may be used to evaluate cloned cell lines for production and quality of biological drug candidates.

EXAMPLES

These examples are provided for illustrative purposes only and not to limit the scope of the claims provided herein.

Example 1—Characterization of Protein Charge on Chip Before Performing Mass Spectrometry The fabrication of the microfluidic device illustrated in FIG. 1 has been described above. To operate, the device is mounted on an instrument containing a nitrogen gas source, heater, positive pressure pump (e.g., Parker, T5-1IC-03-1EEP), electrophoresis power supply (Gamm High Voltage, MC30) terminating in two platinum-iridium electrodes (e.g., Sigma-Aldrich, 357383), UV light source (e.g., LED, qphotonics, UVTOP280), CCD camera (e.g., ThorLabs, 340UV-GE) and an autosampler for loading samples onto the device. The power supply shares a common earth ground with the mass spectrometer. The instrument is controlled through software (e.g., Lab View).

Protein samples are pre-mixed with ampholyte pH gradient and pI markers before placing into vials and loading onto the autosampler. They are serially loaded from an autosampler via the inlet 412 onto the microfluidic device 400 through the enrichment channel 418 and out of the device to waste 430 through the outlet 434.

The sheath/catholyte fluid (50% MeOH, $N_4OH/H_2O$) is loaded onto the two catholyte wells 404, 436, anolyte (10 mM $H_3PO_4$) onto the anolyte well 426, and the source of heated nitrogen gas is attached to the two gas wells 408, 440.

After all reagents are loaded, an electric field of +600V/cm is applied from anolyte well 426 to catholyte wells 404, 436 by connecting the electrodes to the anolyte well 426 and catholyte wells 404, 436 to initiate isoelectric focusing. The UV light source is aligned under the enrichment channel 418, and the camera is placed above the enrichment channel 418 to measure the light that passes through the enrichment channel 418, thereby detecting the focusing proteins by means of their absorbance. The glass plate 402, being constructed of soda-lime glass, acts to block any stray light from the camera, so light not passing through the enrichment channel 418 is inhibited from reaching the camera, increasing sensitivity of the measurement.

Images of the focusing proteins can be captured continuously and/or periodically during IEF. When focusing is complete, low pressure will be applied from the inlet 412, mobilizing the pH gradient toward the orifice 424. The electric field can be maintained at this time to maintain the high resolution IEF separation. Continuing to image the enrichment channel 418 during the ESI process can be used to determine the pI of each protein as it is expelled from the orifice 424.

As the enriched protein fraction moves from the enrichment channel 418 into the confluence 420, it will mix with the sheath fluid, which can flow from the catholyte wells 404, 436 to the confluence 420 via sheath/catholyte fluid channels 406, 438. Mixing enriched protein fractions with the sheath fluid can put the protein fraction in a mass spectrometry compatible solution, and restore charge to the focused protein (IEF drives proteins to an uncharged state), improving the ionization.

The enriched protein fraction then continues on to the orifice 424, which can be defined by a countersunk surface 422 of the glass plate 402. The enriched protein fraction can create a Taylor cone once caught in the electric field between the sheath fluid well ground and mass spectrometer negative pole.

As solution continues to push at the Taylor cone from the enrichment channel 418, small droplets of fluid will be expelled from the Taylor cone and fly towards the mass spectrometer inlet. Nitrogen gas (e.g., at 150° C.) can flow from the gas wells 408, 440, down gas channels 410, 432 and form nitrogen gas jets which flank the Taylor cone which can convert droplets emanating from the Taylor cone to a fine mist before leaving the microfluidic device, which can aid detection in the mass spectrometer. Adjusting pressure from the inlet 412 can adapt Taylor cone size as needed to improve detection in mass spectrometer.

Figure 7A:
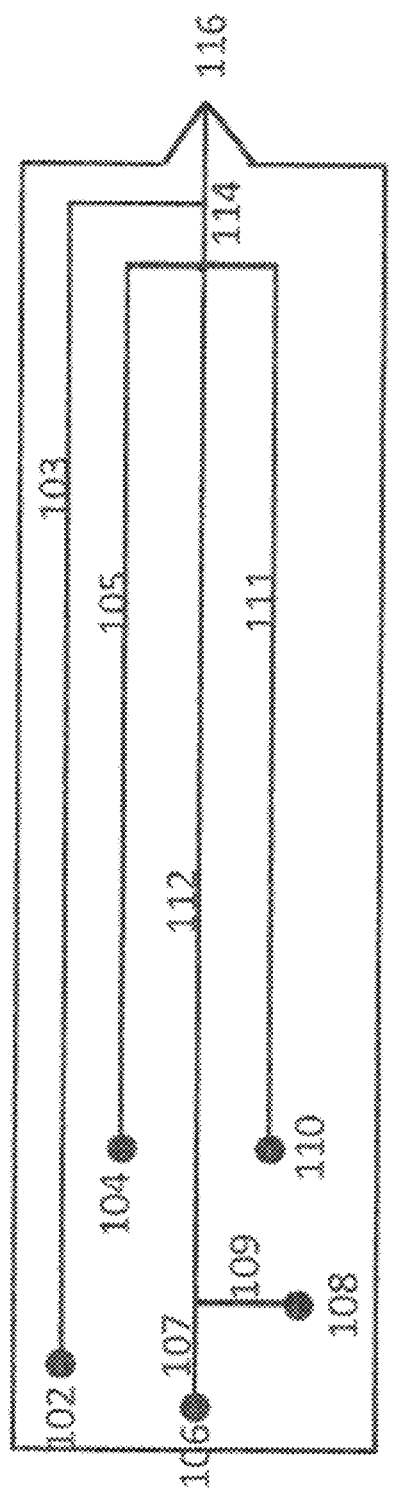
FIGS. 7A-B illustrate a microfluidic device for use in some embodiments of the invention.
Figure 7B:
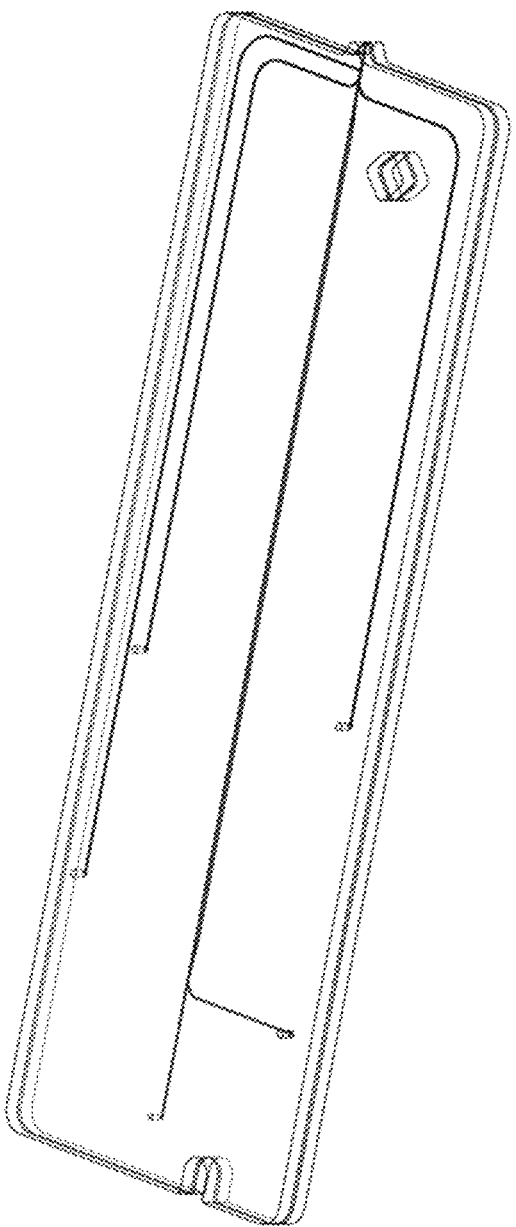

Example 2—Tracking Velocity of Analyte Peaks as they Leave the Microfluidic Chip and Enter the Mass Spectrometer For this example, microfluidic channel network 100 in FIG. 7A is fabricated in a 250-micron thick layer of opaque cyclic olefin polymer. Channel 112 is 250 microns deep, so it cuts all the way through the 250-micron layer. All other channels are 50 microns deep. The channel layer is sandwiched between two transparent layers of cyclic olefin polymer as in FIG. 7B to fabricate a planar microfluidic device. Ports 102, 104, 106, 108 and 110 provide access to the channel network for reagent introduction from external reservoirs and electrical contact. Port 102 is connected to a vacuum source, allowing channel 103 to act as a waste channel, enabling the priming of the other reagents through the channel network to "waste". Acid (1% formic acid) is primed through port 108 to channels 109, 112, 114, and 103, and out to port 102. Sample (4% Pharmalyte 3-10, 12.5 mM pI standard 3.38 (purified peptide, sequence: Trp-Asp-Asp-Asp), 12.5 mM pI standard 10.17 (purified peptide, sequence: Trp-Tyr-Lys-Arg), NIST monoclonal antibody standard (part number 8671, NIST)) is primed through port 106 into channels 107, 112, 114, and 103 and out to port 102. This leaves channel 112 containing the sample analyte. Base (1% dimethylamine) is primed through port 104 into channels 105, 114, and 103 and out to port 102. Mobilizer (1% formic acid, 49% methanol) is primed through port 110 into channels 111, 114, and 103, and out channel 103 to port 102.

Electrophoresis of the analyte sample in channel 112 is performed by applying 4000V to port 108 and connecting port 110 to ground. The ampholytes in the analyte sample establish a pH gradient spanning channel 112. Absorbance imaging of the separation is performed using a 280 nm light source aligned to channel 112 and measuring the transmission of 280 light through the channel 112 with a CCD camera. Software calculates the absorbance by comparing light transmission during separation or mobilization compared to a "blank" reference measurement taken in the absence of focused analyte before the analyte is run, then displays the absorbance per pixel over the length of channel 112. Locations where standards or analyte has focused are displayed as peaks, as indicated in FIGS. 9A-9F.

Once the analyte has completed focusing, a final focused absorbance image is captured. Software will identify the spatial position of the pI markers and interpolate in between the markers to calculate the pI of the focused analyte fraction peaks. At this point, the control software will trigger a relay disconnecting the ground at port 110, and connecting port 104 to ground, as well as setting pressure on the mobilizer reservoir connected to port 104 to establish flow of 100 nL/min of mobilizer solution through port 104 into channels 105 and 114, and out of the chip at orifice 116. Orifice 116 is positioned 2 mm away from a mass spectrometer ESI inlet, with an inlet voltage of −3500V to −4500V.

While the pressure driven flow directs mobilizer from port 104 to orifice 116, some of the formic acid in the mobilizer reagent will electrophorese in the form of formate from channel 105, through channel 112 to the anode at port 108. As the formate travels through channel 112 it will disrupt the isoelectric pH gradient, causing the ampholytes, standards and analyte sample to increase charge and migrate electrophoretically out of channel 112 into channel 114, where pressure driven flow from port 110 will carry them into the ESI spray out of orifice 116.

While mobilization occurs, the software continues to capture absorbance images, and identifies peaks, tracking their migration out of the imaging channel 112 into channel 114. By tracking the time each peak leaves imaging channel 112, its velocity, and the flow rate in channel 114 the software can calculate the time the peak traverses channel 114 is introduced to the mass spectrometer via orifice 116, allowing direct correlation between the original focused peak and the resulting mass spectrum.

Figure 9D:
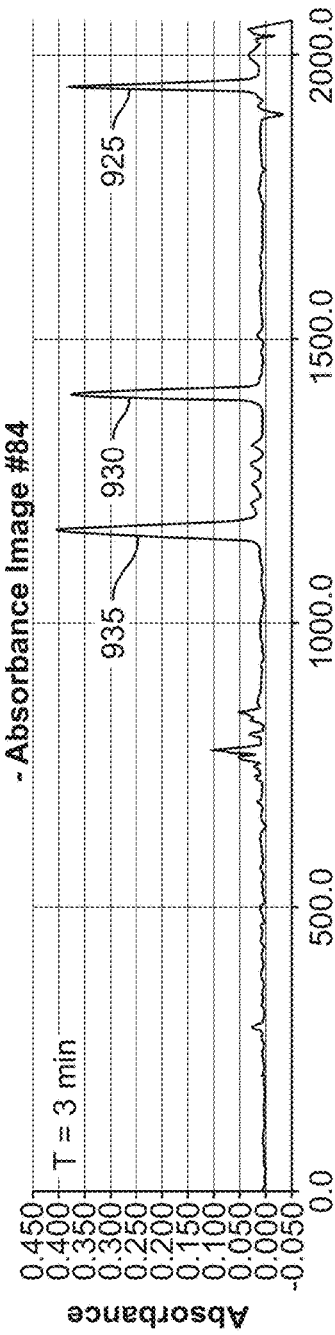
Figure 9E:
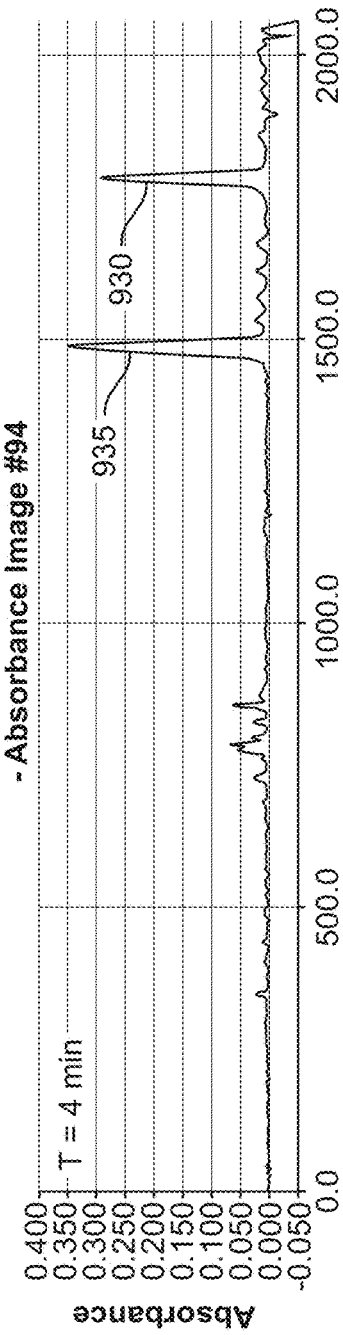
Figure 9F:
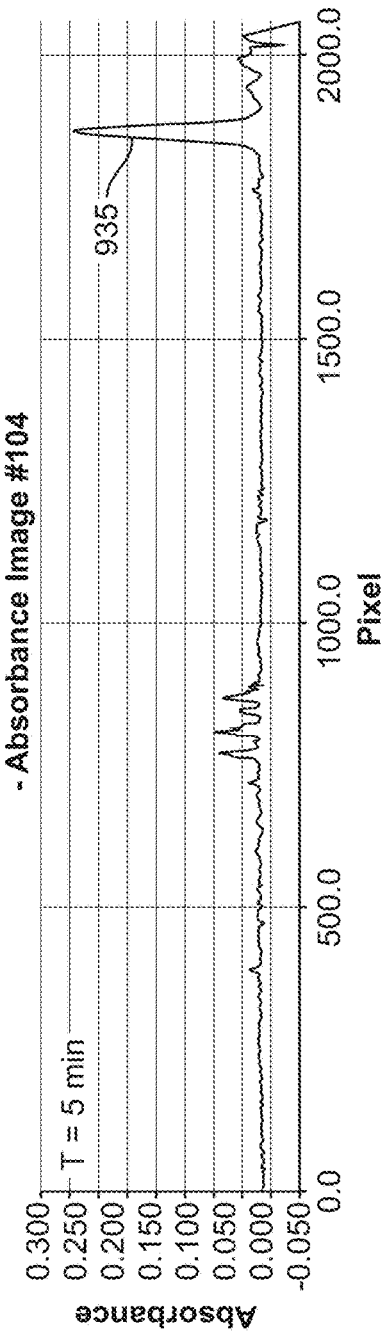

FIGS. 9A-F provide examples of a series of absorbance traces, taken 1 minute apart, showing the mobilization of isoelectric point (pI) standards as determined from images of a separation channel. FIG. 9A shows a plot of absorbance 910 as a function of channel distance 905 after isoelectric focusing of five pI standards (peaks 915, 920, 925, 930, 935) has been completed, prior to mobilization. As shown in FIG. 9B, after 1 min of mobilization, peak 915, corresponding to the pI=9.99 standard, is at the edge of the field-of-view of the imaging system. As shown in FIG. 9C, after 2 min of mobilization, the peak 915 (pI=9.99 standard) has exited the portion of the channel being imaged. As shown in FIG. 9D, after 3 min. of mobilization, peak 920 (pI=8.40 standard) has exited the portion of the channel being imaged. As shown in FIG. 9E, after 4 min. of mobilization, peak 925 (pI=7.00 standard) has exited the portion of the channel being imaged. As shown in FIG. 9F, after 5 min. of mobilization, peak 930 (pI=4.05 standard) has left the portion of the channel being imaged.

Example 3—Using Feedback to Adjust MS and ESI Parameters

Figure 8:
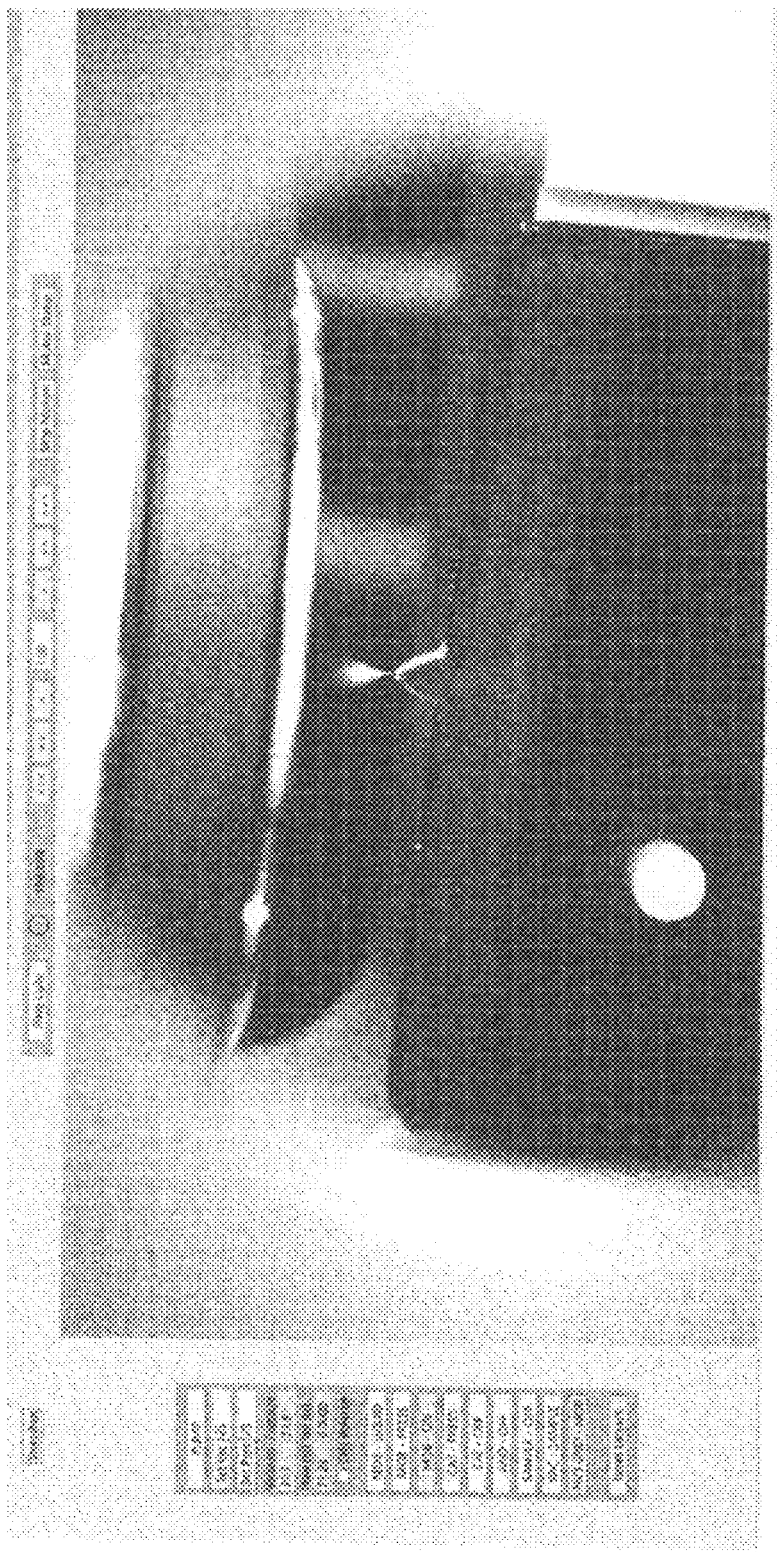
FIG. 8 provides an image of the Taylor cone and electrospray ionization (ESI) plume during mobilization of a separated sample.

In example 3, the chip, instrument and software perform all the same procedures as in example 2. In addition, a second CCD camera is used to image the Taylor cone during ESI, as illustrated in FIG. 8. These images are used to evaluate the quality and consistency of the Taylor cone. Evaluating the image and/or total in count on the mass spectrometer allows for identification of ESI Taylor cone failure and diagnosis of cause.

Taylor cone formation in ESI is dependent on maintaining an input flow into the cone that matches the rate of fluid being lost to evaporation and ESI. The size of the Taylor cone is dependent on flowrate, voltage gradient between microfluidic device and MS, distance between microfluidic device and MS, as well as subtle variation in the ESI tip of the microfluidic device and local environment.

Imaging of the Taylor cone allows diagnosis of the cause of ESI failure. For example, loss of Taylor cone is indicative of not enough flow, and software can increase flow of mobilizer into microfluidic device. Likewise, coronal discharge indicates the voltage is too high, and software can reduce voltage. Expansion of ESI cloud indicates too high a voltage, while forming a droplet rather than a Taylor cone indicates voltage is too low. These differences, and any other visual differences, can be identified in images and the software can automatically compensate to reestablish the Taylor cone.

Example 4—Low Mass Scan as Marker for Separation

In example 4, the chip, instrument and software perform all the same procedures as in example 2. In addition, once mobilization occurs and analyte peaks begin to migrate to the MS, the MS is set to alternate between m/z ranges of 1500-6000 and 150-1500. The 1500-6000 range is used to identify NIST Antibody analyte fraction peaks as they are introduced to the MS. The 150-1500 m/z range scan is used to identify the free solution ampholytes (Pharmalytes) as they are introduced to the MS. The ampholytes can be identified in the mass scan and used to calibrate the total ion chromatograph from the MS, because the presence of particular ampholytes defines portion of the isoelectric pH gradient being analyzed in the MS at any timepoint.

Example 5—Altering High and Low Voltage to Maintain Electric Field Strength and Constant Voltage at Tip For this example, microfluidic channel network 100 in FIG. 7A is fabricated in a 250-micron thick layer of opaque cyclic olefin polymer. Channel 112 is 250 microns deep, so it cuts all the way through the 250-micron layer. All other channels are 50 microns deep. The channel layer is sandwiched between two transparent layers of cyclic olefin polymer as in FIG. 7B to fabricate a planar microfluidic device. Ports 102, 104, 106, 108 and 110 provide access to the channel network for reagent introduction from external reservoirs and electrical contact. Port 102 is connected to a vacuum source, allowing channel 103 to act as a waste channel, enabling the priming of the other reagents through the channel network to "waste". Acid (1% formic acid) is primed through port 108 to channels 109, 112, 114, and 103, and out to port 102. Sample (4% Pharmalyte 3-10, 12.5 mM pI standard 3.38 (purified peptide, sequence: Trp-Asp-Asp-Asp), 12.5 mM pI standard 10.17 (purified peptide, sequence: Trp-Tyr-Lys-Arg), NIST monoclonal antibody standard (part number 8671, NIST)) is primed through port 106 into channels 107, 112, and 114 and out to port 102. This leaves channel 112 containing the sample analyte. Base (1% dimethylamine) is primed through port 104 into channels 105, 114, and 103 and out to port 102. Mobilizer (1% formic acid, 49% methanol) is primed through port 110 into channels 110, 114, and 103 and out channel 102 to port 102. Pressure is applied to the base reservoir to produce a flow of 100 nL/minute through port 104 into channels 105 and 114 and out the orifice 116.

Isoelectric focusing of the analyte sample in channel 112 is initiated by applying 2000V to port 108 using power supply 1005, and connecting port 110 to high-voltage power supply 1010 and applying −2000V. This establishes the circuit represented in FIG. 10A, which includes high-voltage power supply 1005 and high voltage power supply 1010 (in some instances, supply 1005 and supply 1010 may comprise two channels of a single, multiplexed high-voltage power supply), to generate a voltage drop between the anode and cathode of 4000V. The electrical resistances of the channels are dependent of the dimensions of the channels and the conductivity of the reagents. In this example, the electrical resistance of the acid channel, R109, corresponding to channel 109 (see FIG. 7A) is 10 megaohm, the electrical resistance of the sample channel, R112, corresponding to channel 112 (see FIG. 7A) starts at 40 megaohm, and the resistance of the base in channel, R111, corresponding to channel 111 (see FIG. 7A) is 50 megaohm. The resistance of the electrospray ionization (ESI) interface, R113, between orifice 116 (see FIG. 7A) and mass spectrometer 1015 is 2 gigaohm. The total voltage drop across channels 109, 112 and 111 (see FIG. 7A) is 4000V, and since these channels represent three resistors in series, the voltage at the tip ($V_{116}$) is calculated according to equation 1:

$$V_{116} = \Delta V_{108\text{-}110} * (R_{111})/(R_{109}+R_{112}+R_{111}) + (\text{high voltage-power supply 1010 voltage setting}).$$

At the initiation of isoelectric focusing, $V_{116}$=0 volts. Orifice 116 (see FIG. 7A) is positioned 2 mm away from a mass spectrometer ESI inlet, with an inlet voltage of −3500V to −4500V to form the Taylor cone. FIG. 10B shows another embodiment of the circuit represented in FIG. 10A, comprising the resistance R105 of channel 105.

The ampholytes in the analyte sample establish a pH gradient spanning channel 112. Absorbance imaging of the separation is performed using a 280 nm light source aligned to channel 112 and measuring the transmission of 280 nm light through the channel 112 with a CCD camera. Software calculates the absorbance by comparing light transmission during separation or mobilization compared to a "blank" reference measurement taken in the absence of focused analyte before the analyte is run, then displays the absorbance per pixel over the length of channel 112. Locations where standards or analyte has focused are displayed as peaks, as illustrated in FIG. 9A-9F.

As the sample is focusing, the resistance of the sample channel 112 increases, as the ampholytes, antibody isoforms and standards reach their isoelectric points and lose their charge, while resistance in channels 109 and 111 and at the ESI interface remain unchanged. The computer implemented method monitors the current at power supply 1005, and can calculate the resistance at any point in time in channel 112. The computer implemented method uses this information to adjust power supplies 1005 and 1010. For example, when the resistance in channel 112 has climbed to 140 megaohm, if the power supplies were not adjusted, the voltage at orifice 116 would be −1000V, which would disrupt the Taylor cone. But, by adjusting power supply 1005 to +3000V, and power supply 1010 to −1000V, the tip would remain at 0V and the total voltage drop across channels 109, 112 and 111 would remain at 4000V. These adjustments are made on the fly as the resistance in channel 112 changes.

Once the analyte has completed focusing, a final focused absorbance image is captured. Software will identify the spatial position of the pI markers and interpolate in between the markers to calculate the pI of the focused analyte fraction peaks. At this point, the control software will trigger a relay disconnecting power supply 1010 at port 110, and connecting port 104 to power supply 1010, as well as setting pressure on the mobilizer reservoir connected to port 104 to establish flow of 100 nL/min of mobilizer solution through port 104 into channels 105 and 114, and out of the chip at orifice 116 (see chip schematic in FIG. 7A and the electrical circuit illustrated in FIG. 10B). Orifice 116 is positioned 2 mm away from a mass spectrometer ESI inlet, with an inlet voltage of −3500V to −4500V.

While the pressure driven flow directs mobilizer from port 104 to orifice 116, some of the formic acid in the mobilizer reagent will electrophorese in the form of formate from channel 105, through channel 112 to the anode at port 108. As the formate travels through channel 112 it will disrupt the isoelectric pH gradient, causing the ampholytes, standards and analyte sample to increase charge and migrate electrophoretically out of channel 112 into channel 114, where pressure driven flow from port 110 will carry them into the ESI spray out of orifice 116.

Figure 11A:
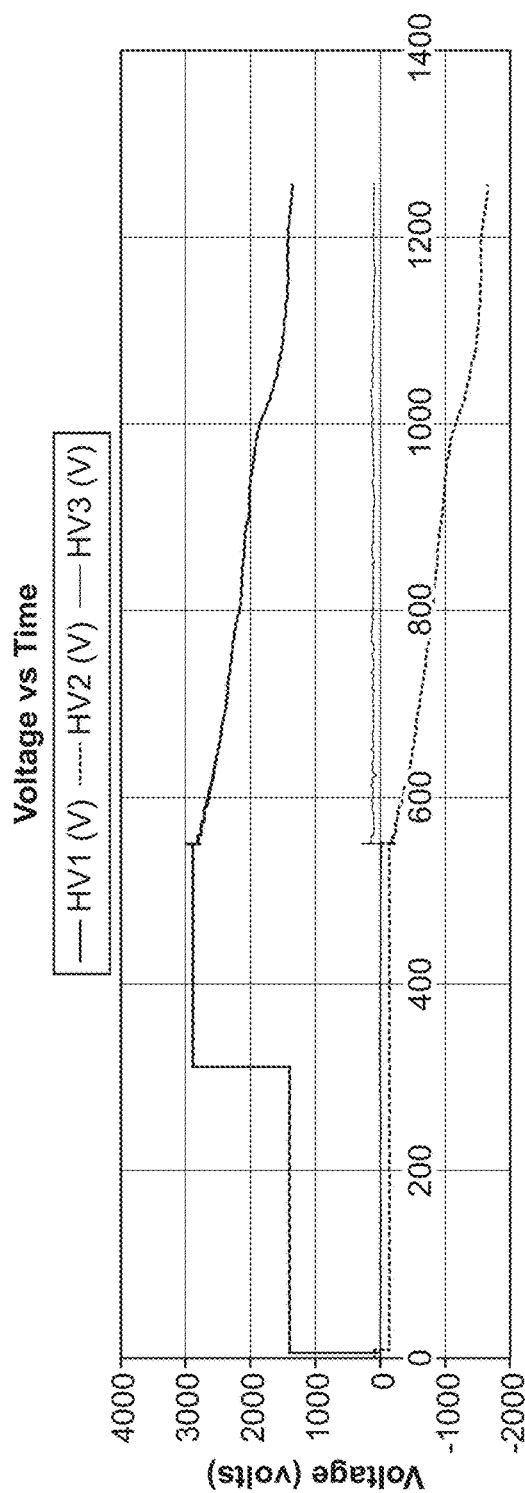
FIGS. 11A-B provide representative data for mobilization while keeping the ESI tip at 0V.
Figure 11B:
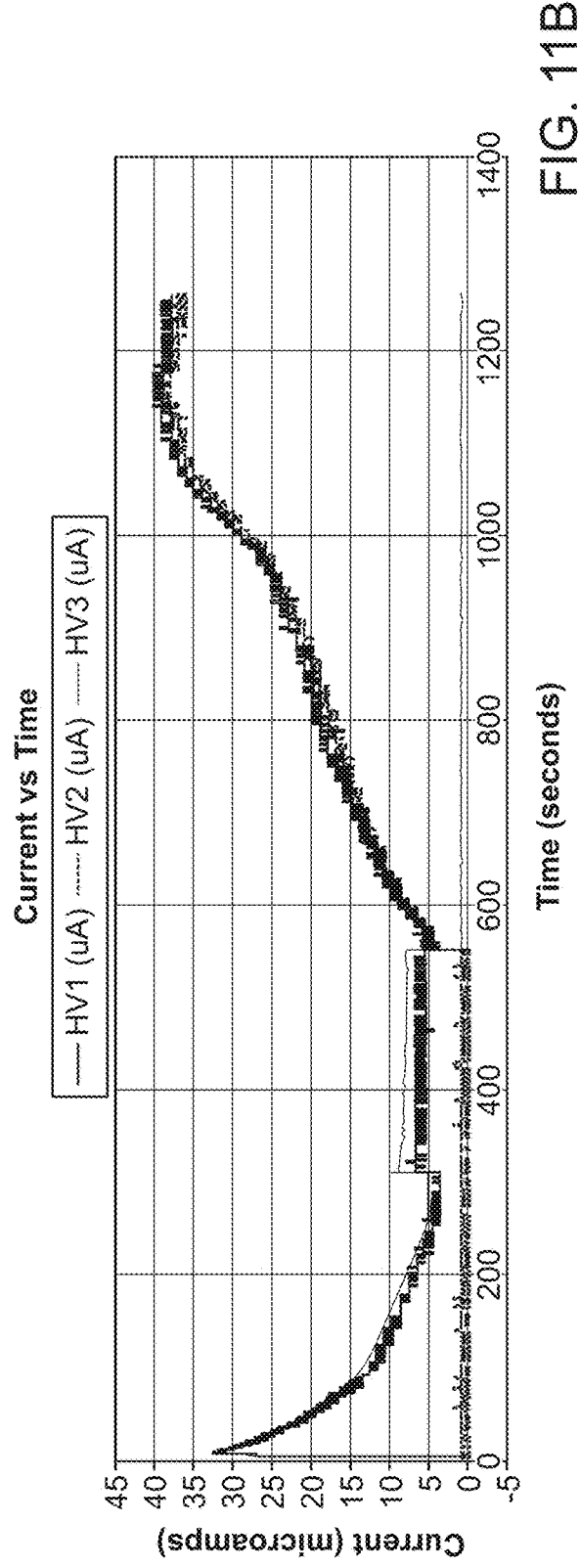

While mobilization occurs, the resistance of channel 112 will drop. FIGS. 11 A-B show examples of voltage and current data for channel 112, which may be used to derive the resistance of the channel. FIG. 11A shows a plot of the voltage as a function of time. FIG. 11B shows a plot of the current as a function of time. Software monitors the change of current, and adjusts the power supplies to maintain a voltage drop between the anode and cathode of 3000V and 0V at tip 116, as described in FIG. 15. The voltage change may be transient or stable.

While mobilization occurs, the software continues to capture absorbance images, and identifies peaks, tracking their migration out of the imaging channel 112 into channel 114. By tracking the time each peak leaves imaging channel 112, its velocity, and the flow rate in channel 114 the software can calculate the time the peak traverses channel 114 is introduced to the mass spectrometer via orifice 116, allowing direct correlation between the original focused peak and the resulting mass spectrum.

Figure 13A:
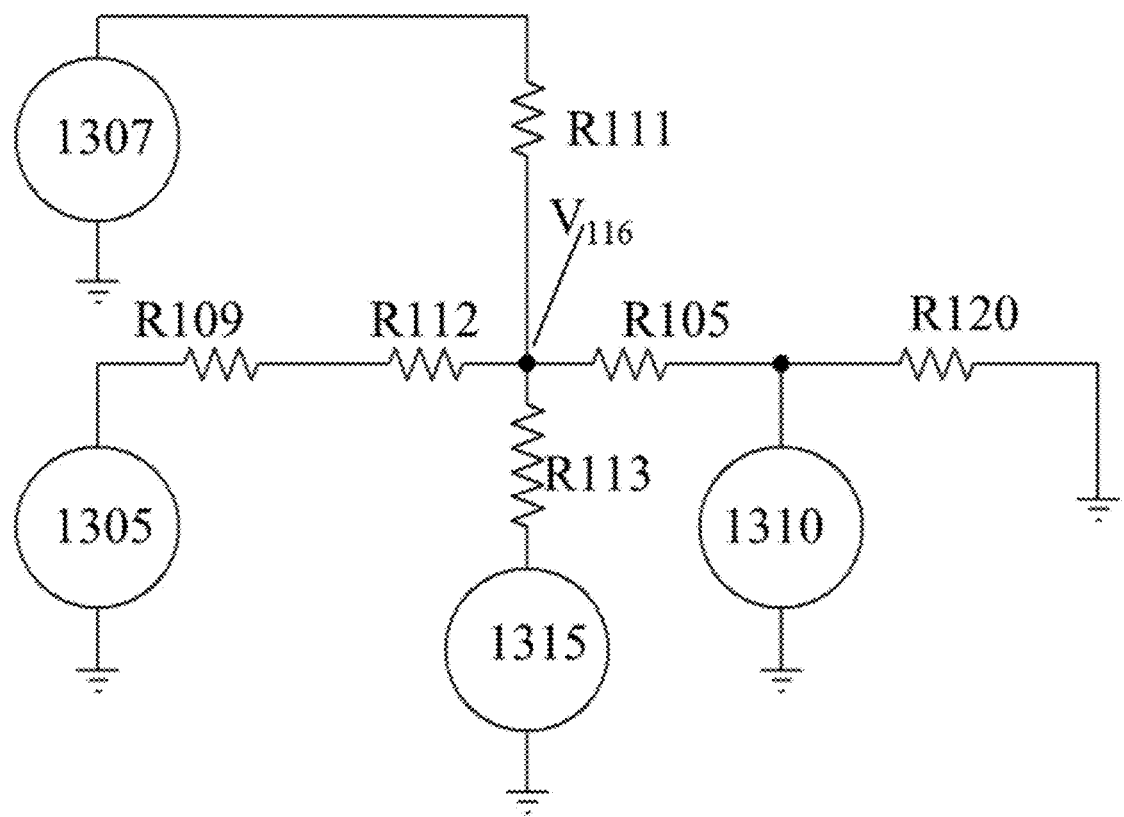
FIGS. 13A-E provide examples of representative circuit diagrams for microfluidic devices of the present disclosure.

FIG. 13A provides a representative circuit diagram for the microfluidic device shown in FIG. 7A during chemical mobilization, where the ESI tip will be held at a positive voltage using an additional resistor R120 to sink current to ground. The circuit may comprise high-voltage power supply 1305, which may be substantially similar to 1005, and high-voltage power supply 1310, which may be substantially similar to 1010, to generate a specified voltage drop between the anode and cathod (e.g., 4000V). The circuit may additionally comprise a third high-voltage power supply 1307. The electrical resistances of the channel are dependent of the dimensions of the channels and the conductivity of the reagents. Also integrated in the circuit is the electrical resistance of the acid channel R109, corresponding to channel 109 (see FIG. 7A), the electrical resistance of the sample channel R112, corresponding to channel 112 (see FIG. 7A), and the resistance of the base in channel R111, corresponding to channel 111 (see FIG. 7A), and the resistance of the electrospray ionization (ESI) R113 interface between orifice 116 (see FIG. 7A) and the voltage supply of the mass spectrometer 1315, which may be substantially similar to 1015. The circuit may also comprise the electrical resistance R105 of channel 105. Power supply 1307 can be connected to channel 111 (see FIG. 7A) and use current control set to 0 µA during mobilization. This power supply may read voltage at the tip and used for implementing a computer-controlled feedback loop to maintain a constant voltage at the tip.

Figure 13B:
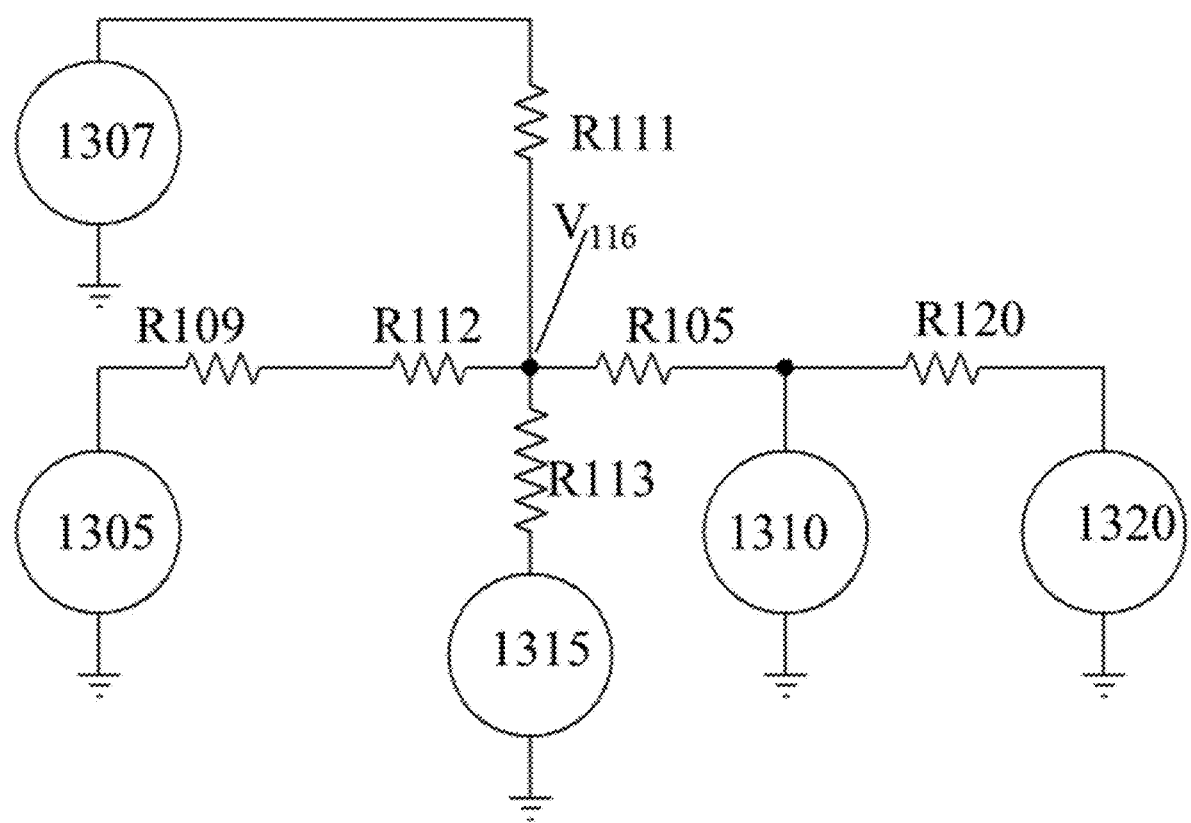
Figure 13C:
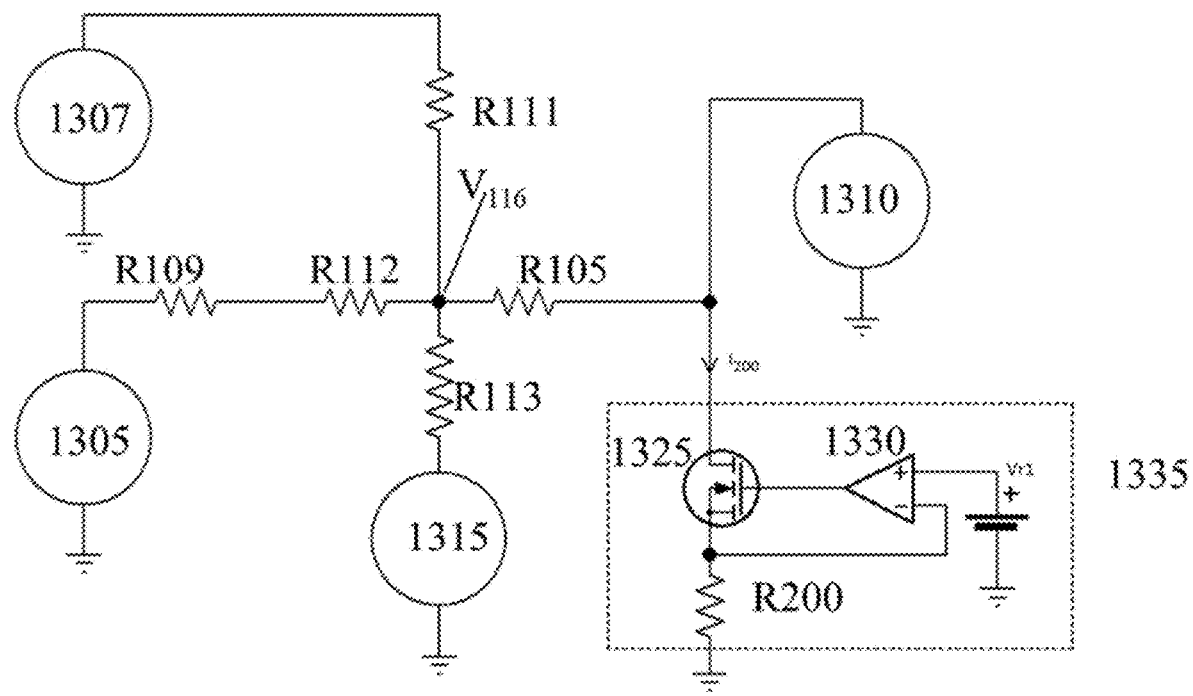
Figure 13D:
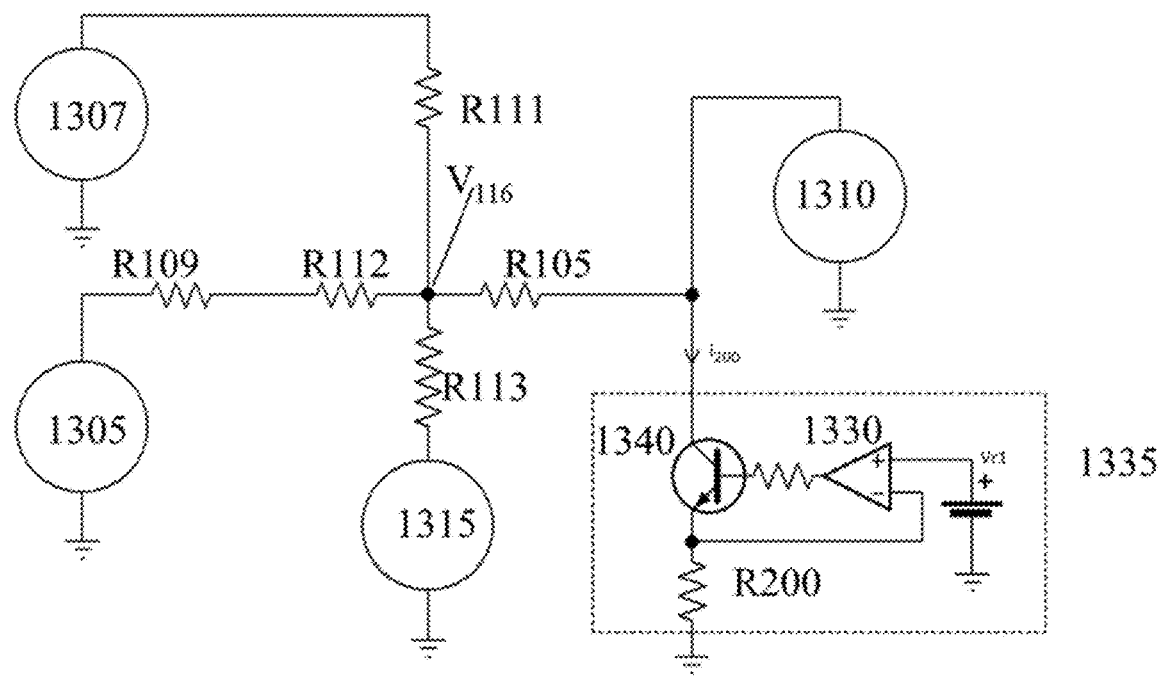

FIG. 13B shows a representative circuit diagram for the microfluidic device shown in FIG. 7A during chemical mobilization, where the ESI tip will be held at a positive voltage using a resistor R120 to sink current to power supply 1320. FIG. 13C shows a representative circuit diagram for the microfluidic device shown in FIG. 7A during chemical mobilization, where the ESI tip will be held at a positive voltage using a field-effect transistor (FET) 1325 to sink current. The electrical circuit may additionally comprise an amplifier 1330, a voltage reference 1335, and an additional resistor R200. FIG. 13D shows a representative circuit diagram for the microfluidic device shown in FIG. 7A during chemical mobilization, where the ESI tip will be held at a positive voltage using a bipolar junction transistor (BJT) 1340 to sink current. Power supply 1307 can be connected to channel 111 (see FIG. 7A) and use current control set to 0 µA. This power supply may read voltage at the tip and used for implementing a computer-controlled feedback loop to maintain a constant voltage at the tip.

Figure 13E:
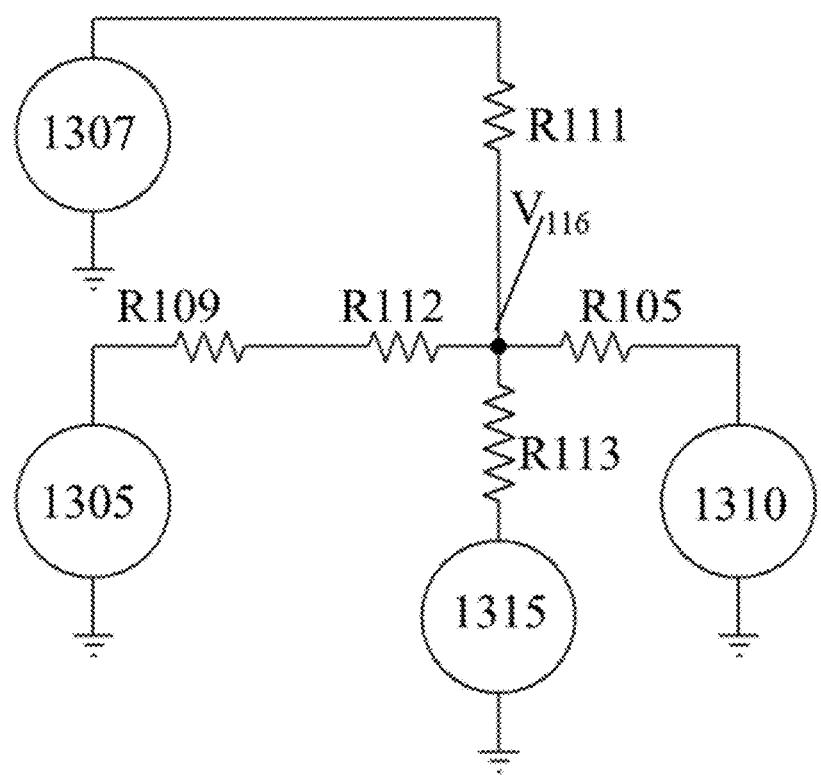

FIG. 13E provides a representative circuit diagram for the microfluidic device shown in FIG. 7A during chemical mobilization of a separated analyte mixture, where ESI tip will be held at or close to ground. Power supply 1307 can be connected to channel 111 (see FIG. 7A) and use current control set to 0 µA. This power supply may read voltage at the tip and used for implementing a computer-controlled feedback loop to maintain a constant voltage at the tip.

Example 6—Altering High and Low Voltage to Maintain Electric Field Strength and Constant Voltage at Tip Based on Measuring Tip Voltage For this example, microfluidic channel network 100 in FIG. 7A is fabricated in a 250-micron thick layer of opaque cyclic olefin polymer. Channel 112 is 250 microns deep, so it cuts all the way through the 250-micron layer. All other channels are 50 microns deep. The channel layer is sandwiched between two transparent layers of cyclic olefin polymer as in FIG. 7B to fabricate a planar microfluidic device. Ports 102, 104, 106, 108, and 110 provide access to the channel network for reagent introduction from external reservoirs and electrical contact. Port 102 is connected to a vacuum source, allowing channel 103 to act as a waste channel, enabling the priming of the other reagents through the channel network to "waste". Acid (1% formic acid) is primed through port 108 to channels 109, 112, 114, and 103, and out to port 102. Sample (4% Pharmalyte 3-10, 12.5 mM pI standard 3.38 (purified peptide, sequence: Trp-Asp-Asp-Asp), 12.5 mM pI standard 10.17 (purified peptide, sequence: Trp-Tyr-Lys-Arg), NIST monoclonal antibody standard (part number 8671, NIST)) is primed through port 106 into channels 107, 112, and 114, and out to port 102. This leaves channel 112 containing the sample analyte. Base (1% dimethylamine) is primed through port 104 into channels 105, 114, and 103, and out to port 102. Mobilizer (1% formic acid, 49% methanol) is primed through port 110 into channels 110, 114, and 103, and out channel 102 to port 102 (see chip schematic of FIG. 7A and the electrical circuit illustrated in FIG. 13E).

Electrophoresis of the analyte sample in channel 112 is initiated by applying 1500V to port 108 using power supply 1305, and connecting port 110 to power supply 1307, set to 0V. After 5 minutes, power supply 1305 is increased to 3000V for 3 minutes to complete focusing.

The ampholytes in the analyte sample establish a pH gradient spanning channel 112. Absorbance imaging of the separation is performed using a 280 nm light source aligned to channel 112 and measuring the transmission of 280 light through the channel 112 with a CCD camera.

Software calculates the absorbance by comparing light transmission during separation or mobilization compared to a "blank" reference measurement taken in the absence of focused analyte before the analyte is run, then displays the absorbance per pixel over the length of channel 112. Locations where standards or analyte has focused are displayed as peaks, as illustrated in FIG. 9A-9F.

Once the analyte has completed focusing, a final focused absorbance image is captured. Software will identify the spatial position of the pI markers and interpolate in between the markers to calculate the pI of the focused analyte fraction peaks. At this point, the control software will trigger a relay connecting port 104 to power supply 1310, as well as setting pressure on the mobilizer reservoir connected to port 104 to establish flow of 100 nL/min of mobilizer solution through port 104 into channels 105 and 114, and out of the chip at orifice 116. Orifice 116 is positioned 2 mm away from a mass spectrometer ESI inlet 1315, with an inlet voltage of −3500V to −4500V. Power supply 1307 is set to 0 μA using current control, power supply 1305 to 3000V and power supply 1310 to 0V, and the MS ESI ion source is set between −3500V and −4500V.

While the pressure driven flow directs mobilizer from port 104 to orifice 116, some of the formic acid in the mobilizer reagent will electrophorese in the form of formate from channel 105, through channel 112 to the anode at port 108. As the formate travels through channel 112, it will disrupt the isoelectric pH gradient, causing the ampholytes, standards and analyte sample to increase charge and migrate electrophoretically out of channel 112 into channel 114, where pressure driven flow from port 110 will carry them into the ESI spray out of orifice 116.

While mobilization occurs, the resistance of channel 112 will drop. Power supply 1307, which is set to 0 μA, will equal the voltage at V116 in FIG. 13E, because the voltage drop across channel 111 is now 0 ($\Delta V = IR = 0 * R111 = 0V$). As shown in the data in FIGS. 11A-B, at 8 minutes (480 seconds) after the focusing is complete, the software monitors change of current, and adjusts the power supplies to maintain a constant voltage drop between the anode and cathode of 3000V and 0 volt at tip 116, as described in FIG. 15. The voltage at the tip (V116) is described by equation 2:

$$V_{116} = \Delta V_{108-110} * (R_{111})/(R_{109} + R_{112} + R_{105}) + (\text{power supply 1310 voltage setting}).$$

While mobilization occurs, the software continues to capture absorbance images, and identifies peaks, tracking their migration out of the imaging channel 112 into channel 114. By tracking the time each peak leaves imaging channel 112, its velocity, and the flow rate in channel 114 the software can calculate the time the peak traverses channel 114 is introduced to the mass spectrometer via orifice 116, allowing direct correlation between the original focused peak and the resulting mass spectrum.

Example 7—Altering High and Low Voltage to Maintain Electric Field Strength and Constant Voltage at Tip Based on Measuring Tip Voltage, and Resistor For this example, microfluidic channel network 100 in FIG. 7A is fabricated in a 250-micron thick layer of opaque cyclic olefin polymer. Channel 112 is 250 microns deep, so it cuts all the way through the 250-micron layer. All other channels are 50 microns deep. The channel layer is sandwiched between two transparent layers of cyclic olefin polymer as in FIG. 7B to fabricate a planar microfluidic device. Ports 102, 104, 106, 108 and 110 provide access to the channel network for reagent introduction from external reservoirs and electrical contact. Port 102 is connected to a vacuum source, allowing channel 103 to act as a waste channel, enabling the priming of the other reagents through the channel network to "waste". Acid (1% formic acid) is primed through port 108 to channels 109, 112, 114, and 103, and out to port 102. Sample (4% Pharmalyte 3-10, 12.5 mM pI standard 5.52 (purified peptide, sequence: Trp-Glu-His), 12.5 mM pI standard 8.4 (purified peptide, sequence: Trp-Tyr-Lys), Infliximab biosimilar monoclonal antibody standard (part number MCA6090, Bio-rad)) is primed through port 106 into channels 107, 112, and 114, and out to port 102. This leaves channel 112 containing the sample analyte. Base (1% dimethylamine) is primed through port 104 into channel 105, 114, 103 and out to port 102. Mobilizer (1% Formic acid, 49% Methanol) is primed through port 110 into channels 110, 114, and 103, and out channel 102 to port 102 (see chip schematic of FIG. 7A and the electrical circuit illustrated in FIG. 13B).

Electrophoresis of the analyte sample in channel 112 is initiated by applying 1500V to port 108 using power supply 1305, and connecting port 110 to power supply 1307, set to 0V. After 5 minutes, power supply 1305 is increased to 3000V.

The ampholytes in the analyte sample establish a pH gradient spanning channel 112. Absorbance imaging of the separation is performed using a 280 nm light source aligned to channel 112 and measuring the transmission of 280 nm light through the channel 112 with a CCD camera. Software calculates the absorbance by comparing light transmission during separation or mobilization compared to a "blank" reference measurement taken in the absence of focused analyte before the analyte is run, then displays the absorbance per pixel over the length of channel 112. Locations where standards or analyte has focused are displayed as peaks, as illustrated in FIG. 9A-9F.

Figure 16D:
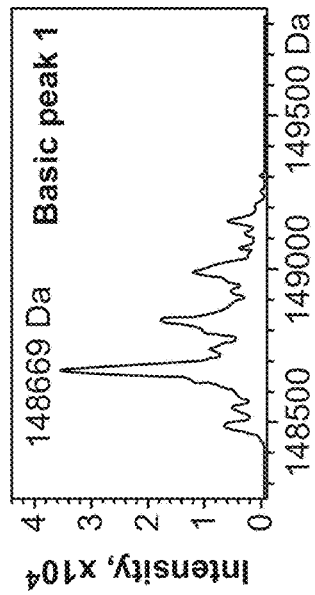
FIGS. 16A-E provide examples of analyte separation data and the corresponding mass spectrometry data for separated analyte species.
Figure 16E:
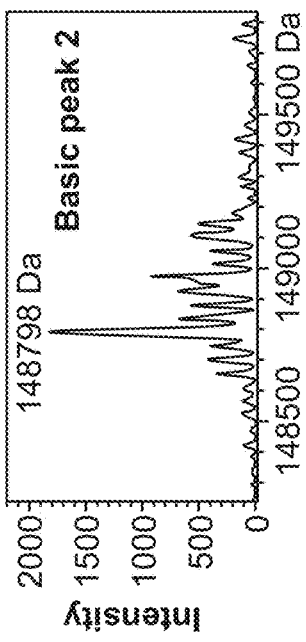
Figure 16C:
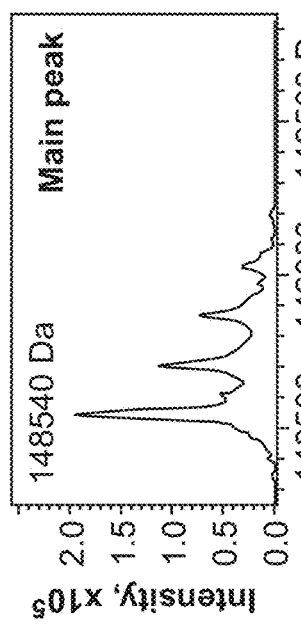
Figure 16A:
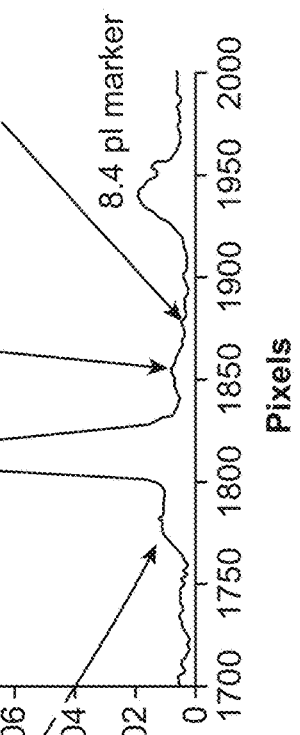

Once the analyte has completed focusing, the charge variants of infliximab are separated as shown in FIG. 16A, and a final focused absorbance image is captured. Software will identify the spatial position of the pI markers and interpolate in between the markers to calculate the pI of the focused analyte fraction peaks. At this point, the control software will trigger a relay connecting port 104 to power supply 1310, as well as setting pressure on the mobilizer reservoir connected to port 104 to establish flow of 100 nL/min of mobilizer solution through port 104 into channels 105 and 114, and out of the chip at orifice 116. Orifice 116 is positioned 2 mm away from a mass spectrometer ESI inlet, 1315. Power supply 1307 is set to 0 μA using current control, power supply 1305 is set to 7000V, power supply 1310 is set to 4000V, and the MS ESI ion source 1315 is held at ground. An additional resistor R120 is connected to the system between power supply 1310 and channel 105 (R current sink), and the other side of resistor R120 is connected to power supply 1320 as shown in FIG. 13B. Power supply 1320 will be set at a minimum of 4000V less than power supply 1310 in order to act as current sink. Resistor R120 could instead connect the electrical circuit to ground, as in FIG. 13A, could be a field-effect transistor (FET) as shown in FIG. 13C, could be a bipolar-junction transistor (BJT) as shown in FIG. 13D, or any other resistive element which could sink current from power supply 1310 to create a functioning electrophoresis circuit.

While the pressure driven flow directs mobilizer from port 104 to orifice 116, some of the formic acid in the mobilizer reagent will electrophorese in the form of formate from channel 105, through channel 112 to the anode at port 108. As the formate travels through channel 112 it will disrupt the isoelectric pH gradient, causing the ampholytes, standards and analyte sample to increase charge and migrate electrophoretically out of channel 112 into channel 114, where pressure driven flow from port 110 will carry them into the ESI spray out of orifice 116.

While mobilization occurs, the resistance of channel 112 will drop. Power supply 1307, which is set to 0 µA, will equal the voltage at V116, because the voltage drop across channel 111 is now 0 ($\Delta V=IR=0*R111=0V$). As shown in data in FIGS. 11A and 11B, the software monitors change of current, and adjusts the power supplies to maintain a constant voltage drop between the anode and cathode of 3000V, and 3000 volt at tip 116, as described in FIG. 12. The voltage at the tip (V116) is described by equation 2:

$$V_{116}=\Delta V_{108\text{-}110}*(R_{111})/(R_{109}+R_{112}+R_{105})+(\text{power supply 1310 voltage setting}).$$

Figure 16B:
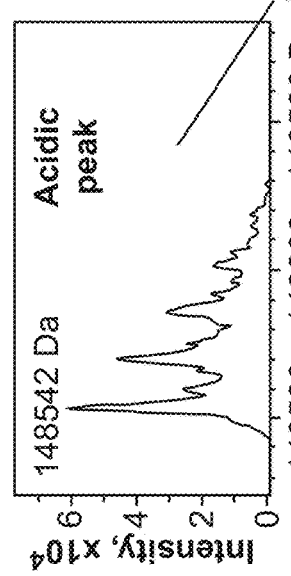

While mobilization occurs, the software continues to capture absorbance images, and identifies peaks, tracking their migration out of the imaging channel 112 into channel 114. By tracking the time each peak leaves imaging channel 112, its velocity, and the flow rate in channel 114 the software can calculate the time the peak traverses channel 114 is introduced to the mass spectrometer via orifice 116, allowing direct correlation between the original focused peak and the resulting mass spectra. For example, FIG. 16B shows the mass of the glycoforms electrosprayed into the mass spectrometer that were contained in the acidic peak of the electropherogram shown in FIG. 16A. FIG. 16C shows the mass of glycoforms in the main infliximab peak from FIG. 16A. FIG. 16D and FIG. 16E show the masses of the basic peaks from the electropherogram shown in FIG. 16A.

Example 8—Altering High and Low Voltage to Maintain Electric Field Strength and Constant Voltage in 2-Step Capillary IEF In Example 8, 2-step IEF (isoelectric focusing followed by mobilization) is performed in a 60 cm capillary, and mobilized into ESI-MS through a junction sprayer, as outlined in FIG. 14A. Separation capillary 1808 is immersed in anolyte vial 1806. High voltage power supply 1802 is connected to anolyte vial 1806 through electrode 1804. The other end of capillary 1808 is connected through tee union 1812 to junction sprayer 1814. Capillary 1808 is inserted into junction sprayer 1814 so the capillary outlet is in close proximity to ESI tip 1824. The third arm of tee union 1812 is connected to mobilizer capillary 1816 which is immersed in pressurized mobilizer vial 1818. Pressurized mobilizer vial 1818 is also grounded via electrode 1817 so it may act as a current sink. In addition, junction sprayer 1814 is connected to power supply 1810 through wire 1820 which connects to the outside of sprayer 1814. In this example, the mass spectrometer ion source is held at ground.

Reagents are prepared as follows. Anolyte vial 1806 is filled with 1% formic acid in water, separation capillary 1808 is filled with aqueous sample (250 µg/mL NIST mAb, 1.5% Pharmalyte 5-8 ampholyte, 1.5% Pharmalyte 8-10.5, 5 mg/mL pI standard 7.00 and 10.17), junction sprayer chamber 1826 and mobilizer capillary 1816 are filled with 1% diethylamine in water, and pressurized mobilizer vial 1818 is filled with 1% formic acid, 50% acetonitrile, and 49% water.

In this example, the mass spectrometer ion source is held at ground. To initiate focusing, power supply 1802 is set to +30 kV, power supply 1810 is set to 4 kV. And pressure driven flow from mobilizer vial 1818 is initiated at 100 nL/min. In this way, ESI is initiated using the diethylamine in the junction sprayer cavity 1826, and the diethylamine also acts as catholyte for the isoelectric focusing step.

Figure 14B:
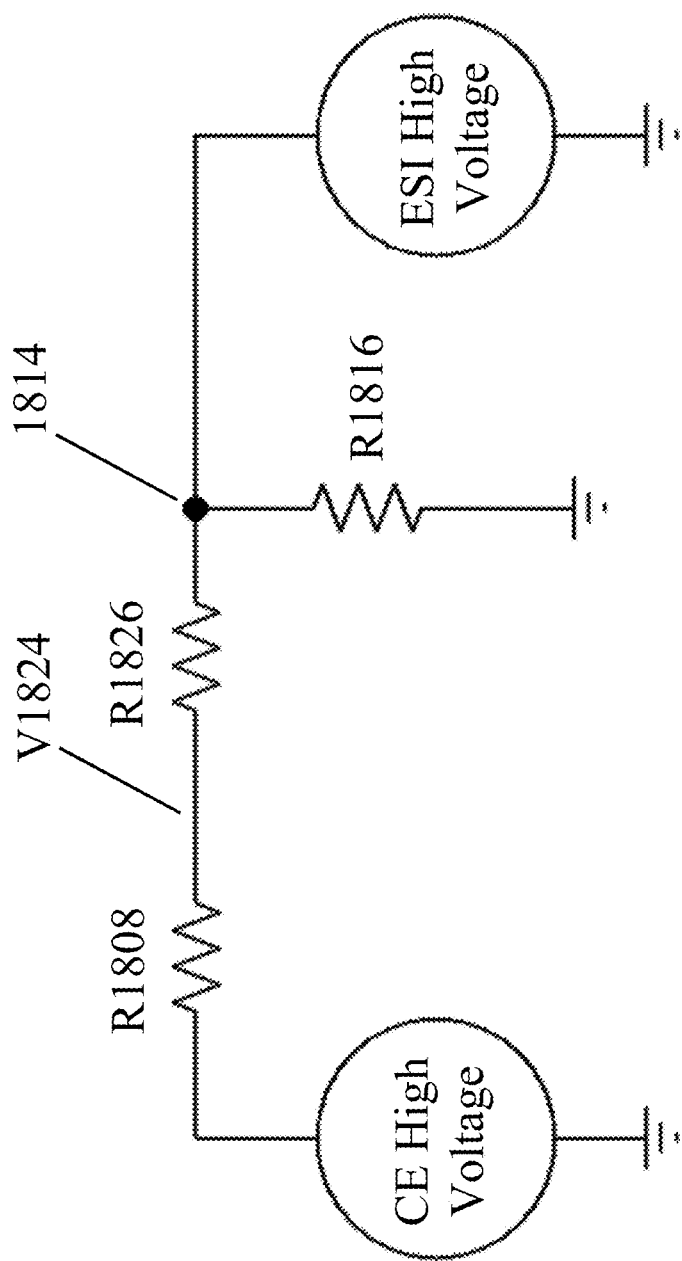
FIG. 14B shows the representative resistor circuit diagram for the capillary junction sprayer diagram in FIG. 14A.

As focusing proceeds in capillary 1808, the sample loses charge carrying capacity and resistance increases in capillary 1808. As the ESI tip is positioned electrically between capillary 1808 and diethylamine in chamber 1826 (See FIG. 14B), the ESI tip voltage ($V_{1824}$) will drop in accordance with equation 3:

$$V_{1824}=\Delta V_{1806\text{-}1814}*R_{1826}/(R_{1808}+R_{1826})+V_{1814}$$

In addition, as the resistance in capillary 1808 increases, the current passing through the capillary will decrease, which can be measured at power supply 1802. The increased current will be directly related to resistance change in capillary 1808 by equation 4:

$$I_{1806}=\Delta V_{1806\text{-}1814}/(R_{1808}+R_{1826})$$

Using a computer-controlled feedback loop as described in FIG. 12, the system can calculate the change in resistance in capillary 1808 (and therefore the change in voltage drop across capillary 1808, which defines voltage at ESI tip 1824), the system can adjust power supplies 1802 and 1810 to retain the ΔV of 26 kV, and maintain a ESI tip voltage of 4000 kV.

After focusing is complete (~30 minutes), the mobilizer solution in pressurized mobilizer vial 1818 will have replaced the diethylamine injunction sprayer chamber 1826, initiating mobilization of the NIST mAb protein isoforms in capillary 1808. In similar fashion but opposite to isoelectric focusing, as mobilization proceeds, resistance in capillary 1808 will drop, affecting the voltage at ESI tip 1824. Once again, the computer-controlled feedback loop will use equations 3 and 4 to calculate the necessary change to power supplies 1802 and 1810 to maintain a 26 kV electric field while keeping ESI tip 1824 voltage at 4 kV.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A method for maintaining an electrospray ionization (ESI) tip at a constant voltage relative to ground while performing a separation reaction, the method comprising:

a) applying a first voltage to a proximal end of a separation channel, wherein a distal end of the separation channel is in fluid and electrical communication with the ESI tip;
b) applying a second voltage to a proximal end of an auxiliary fluid channel, wherein a distal end of the auxiliary fluid channel is in fluid and electrical communication with the distal end of the separation channel;
c) performing the separation reaction to separate a mixture of analytes, wherein the separation reaction takes place within the separation channel; and
d) monitoring a change in resistance of the separation channel or a change in voltage at the ESI tip in a feedback loop that adjusts the first and second voltages to maintain a constant voltage drop across the separation channel and a constant voltage at the ESI tip.

2. The method of claim 1, wherein the separation channel is a lumen of a capillary.

3. The method of claim 2, wherein the capillary comprises a microvial spray tip.

4. The method of claim 1, wherein the separation channel is a fluid channel within a microfluidic device.

5. The method of claim 1, wherein the separation reaction comprises an isoelectric focusing reaction.

6. The method of claim 1, wherein the separation reaction comprises an electrophoretic separation reaction.

7. The method of claim 1, wherein the first voltage is applied at a cathode and the second voltage is applied at an anode.

8. The method of claim 1, wherein the voltage at the ESI tip is held at ground.

9. The method of claim 1, wherein the voltage at the ESI tip is held at the second voltage.

10. The method of claim 1, wherein the adjustment to the first and second voltages comprises subtracting a transient voltage change measured at the ESI tip from the first voltage and second voltage.

11. The method of claim 1, wherein the voltage at the ESI tip is measured using a power supply that provides the first or second voltage.

12. The method of claim 1, wherein the feedback loop operates at a frequency of at least 0.1 Hz.

13. The method of claim 1, wherein the feedback loop operates at a frequency of at least 10 Hz.

14. The method of claim 1, wherein the feedback loop maintains the voltage at the ESI tip to within ±10% of a pre-set value.

15. The method of claim 1, wherein the feedback loop maintains the voltage at the ESI tip to within ±1% of a pre-set value.

16. The method of claim 1, wherein the feedback loop maintains the voltage drop across the separation channel to within ±10% of a pre-set value.

17. The method of claim 1, wherein the feedback loop maintains the voltage drop across the separation channel to within ±1% of a pre-set value.

18. A computer-implemented method for maintaining an electrospray ionization (ESI) tip at a constant voltage relative to ground while performing a separation reaction, the method comprising:
a) receiving, using a processor, a first measurement of a voltage at the ESI tip, wherein a distal end of the separation channel is in fluid and electrical communication with the ESI tip;
b) receiving, using the processor, a second measurement of the voltage at the ESI tip;
c) comparing the second measurement to the first measurement using the processor, wherein if the second measurement differs from the first measurement, the processor causes a voltage at a proximal end of the separation channel and a voltage at a proximal end of an auxiliary fluid channel comprising a distal end that is in fluid and electrical communication with the distal end of the separation channel, to be adjusted such that the voltage at the ESI tip is returned to the first measurement value; and
d) repeating steps (a) through (c) at a specified frequency.

19. The computer-implemented method of claim 18, wherein the separation channel comprises a lumen of a capillary or a fluid channel within a microfluidic device.

20. The computer-implemented method of claim 18, wherein the separation reaction comprises an isoelectric focusing reaction.

21. The computer-implemented method of claim 18, wherein the separation reaction comprises an electrophoretic separation reaction.

22. The computer-implemented method of claim 18, wherein the voltage at the ESI tip is held at ground.

23. The computer-implemented method of claim 18, wherein the specified frequency is at least 1 Hz.

24. The computer-implemented method of claim 18, wherein the voltage at the ESI tip is maintained to within ±5% of a specified value.

* * * * *